United States Patent [19]

Ibuki et al.

[11] Patent Number: 4,751,302

[45] Date of Patent: Jun. 14, 1988

[54] INDAZOLE DERIVATIVES

[75] Inventors: Tadayuki Ibuki; Taisuke Sugihara; Hiromu Kawakubo; Takanori Sone, all of Nobeoka, Japan

[73] Assignee: Asahi Kasei Kogyo Kabushiki Kaisha, Japan

[21] Appl. No.: 739,061

[22] Filed: May 29, 1985

Related U.S. Application Data

[62] Division of Ser. No. 475,945, Mar. 16, 1983, Pat. No. 4,533,731.

[30] Foreign Application Priority Data

| Mar. 17, 1982 | [JP] | Japan | 57-40686 |
| Mar. 17, 1982 | [JP] | Japan | 57-40687 |
| Mar. 17, 1982 | [JP] | Japan | 57-40688 |
| Mar. 17, 1982 | [JP] | Japan | 57-40689 |
| Mar. 17, 1982 | [JP] | Japan | 57-40690 |
| Mar. 17, 1982 | [JP] | Japan | 57-40691 |
| Mar. 17, 1982 | [JP] | Japan | 57-40192 |

[51] Int. Cl.$^4$ .................. C07D 231/5; C07D 401/07; A61K 31/415; C07C 87/00

[52] U.S. Cl. .................. 544/140; 544/360; 544/371; 546/199; 548/357; 548/359; 548/372

[58] Field of Search .................. 544/140, 360, 371; 546/190; 548/357, 359, 377; 514/403

[56] References Cited

U.S. PATENT DOCUMENTS

| 4,474,964 | 10/1984 | Ibuki et al. | 548/372 |
| 4,533,731 | 8/1985 | Ibuki et al. | 544/140 |
| 4,549,023 | 10/1985 | Ibuki et al. | 548/372 |
| 4,585,869 | 4/1986 | Ibuki et al. | 548/372 |

*Primary Examiner*—Richard L. Raymond
*Assistant Examiner*—Raymond Covington
*Attorney, Agent, or Firm*—Finnegan, Henderson, Farabow, Garrett & Dunner

[57] ABSTRACT

A compound of the formula (I):

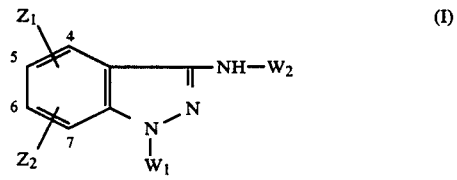

wherein $W_1$ and $W_2$ each independently is a hydrogen atom or a

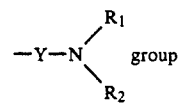

wherein Y is a n-$C_{1-6}$ alkylene group or a n-$C_{1-6}$ alkylene group having a $C_{1-6}$ alkyl group substituent; and $R_1$ and $R_2$ each independently is a hydrogen atom or a $C_{1-6}$ alkyl group, and

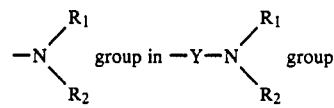

may form a saturated heterocyclic ring selected from the group consisting of morpholino, pyrrolidino, piperidino, homopiperidino and piperazino groups, and the saturated heterocyclic ring except the morpholino group may have at least one $C_{1-4}$ alkyl group, hydroxyl group or halogen atom as a substituent;

$Z_1$ is a hydrogen atom, a chlorine atom, a bromine atom, an iodine atom, a hydroxyl group, an amino group, a $C_{1-3}$ alkyl group or a methoxy group;

$Z_2$ is a hydrogen atom or an amino group;

when $W_1$ and $W_2$ are both hydrogen atoms, $Z_1$ is a hydroxyl group or an iodine atom and $Z_2$ is hydrogen atom, or $Z_1$ and $Z_2$ are both amino groups;

when $Z_1$ and $Z_2$ are both hydrogen atoms, the

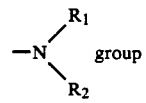

in either $W_1$ or $W_2$ is a morpholino group;

when $Z_1$ is a chlorine atom, a hydroxyl group, an iodine atom, a methyl group or a methoxy group, $Z_2$ is a hydrogen atom;

when $Z_1$ is an amino group, $Z_2$ is a hydrogen atom or an amino group;

when $Z_1$ is a methyl group, a methoxy group or an amino group, $Z_1$ is in the 5-position; when $Z_1$ is an iodine atom, $Z_1$ is in the 5- or 7-position; and when $Z_1$ and $Z_2$ are both amino groups, $Z_1$ and $Z_2$ are in the 5- and 7-positions;

and the physiologically acceptable acid addition salt thereof.

42 Claims, No Drawings

INDAZOLE DERIVATIVES

This is a division of application Ser. No. 475,945, filed 3/16/83 now U.S. Pat. No. 4,533,731.

BACKGROUND OF THE INVENTION

1. Field of the Invention

This invention relates to novel indazole derivatives which are useful in therapeutics. More specifically, this invention relates to novel indazole derivatives having valuable effects for relief of inflammation, analgesic activity and for suppressing digestive tract ulcers, a side effect caused by using acidic non-steroidal anti-inflammatory drugs.

2. Description of the Prior Art

Various experiments to obtain novel and useful anti-inflammatory drugs have been done by many researchers in the field of synthetic organic chemistry. Most of the experiments relate to the synthesis or testing of steroidal hormone compounds such as corticosteriods, and acidic non-steroidal substances such as phenylbutazon and indomethacin. However, both of the steroidal hormone compounds and the acidic non-steroidal substances have undesirable side effects. On the other hand, basic non-steroidal agents show almost no side effects such as digestive tract ulcers cause by the acidic non-steroidal compounds, in addition to the fact that they have the same anti-inflammatory effect and analgesic activity as the usual acidic non-steroidal compounds. As the basic non-steroidal compounds, 3-aminoindazole was first reported in Bamberger, Liebigs Ann., 305, 339(1899).

A 3-aminoindazole derivative whose condensed phenyl ring has a halogen group or a trifluoromethyl group as a substituent and whose nitrogen atom at the 1-position has a hydrogen atom, a methyl group or a phenyl group is described in U.S. Pat. No. 3,133,081. This patent discloses usage of these compounds as drugs having central nervous system activity, and as muscle relaxants, analgesics and tranquilizers. However, pharmacological data of the derivatives are not disclosed. Moreover, the compounds of U.S. Pat. No. 3,133,081 have never been actually used as medicines.

Silvest et. al., Arzneim-Forsch, 16, 59 (1966) report that 1-benzyl-3-(3-dimethylaminopropoxy)indazole hydrochloride is effective against primary inflammation. For example, benzydamine hydrochloride is actually used as a medicine.

U.S. Pat. No. 3,681,382 discloses other 3-aminoindazole derivatives wherein the hydrogen atom linked with the 1-position nitrogen atom is substituted by an aryl group and the 3-position is a substituted ω-aminoalkyl group or an ω-heterocyclic aminoalkyl group having 1 to 5 carbon atoms together with the nitrogen atom; or a substituted ω-aminoalkylamido group or an ω-heterocyclic aminoalkylamido group having 1 to 5 carbon atoms together with the nitrogen atom. The patent also discloses usage of antidepressants and anti-inflammatory drugs. However, pharmacological data are not disclosed in the U.S. patent. Moreover, these compounds have never been actually used as medicines.

Though some indazole derivatives are known as described above, the prior art fails to teach or suggests the indazole derivatives of this invention.

SUMMARY OF THE INVENTION

According to the present invention there is provided an indazole derivative of the formula (I):

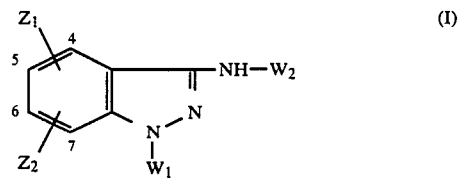

wherein
$W_1$ and $W_2$ each independently is a hydrogen atom or a

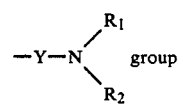

group wherein Y is a n-$C_{1-6}$ alkylene group or a n-$C_{1-6}$ alkylene group having a $C_{1-6}$ alkyl group substituent; and $R_1$ and $R_2$ each independently is a hydrogen atom or a $C_{1-6}$ alkyl group, and

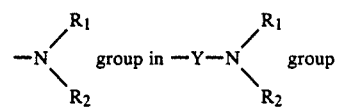

may form a saturated heterocyclic ring selected from the group consisting of morpholino, pyrrolidino, piperidino, homopiperidino and piperazino groups, and the saturated heterocyclic ring except the morpholino group may have at least one $C_{1-4}$ alkyl group, hydroxyl group or halogen atom as a substituent;

$Z_1$ is a hydrogen atom, a chlorine atom, a bromine atom, an iodine atom, a hydroxyl group, an amino group, a $C_{1-3}$ alkyl group or a methoxy group;

$Z_2$ is a hydrogen atom or an amino group;

when $W_1$ and $W_2$ are both hydrogen atoms, $Z_1$ is a hydroxyl group or an iodine atom and $Z_2$ is a hydrogen atom, or $Z_1$ and $Z_2$ are both amino groups;

when $Z_1$ and $Z_2$ are both hydrogen atoms, the

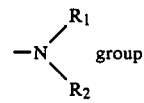

group in either $W_1$ or $W_2$ is a morpholino group;

when $Z_1$ is a chlorine atom, a hydroxyl group, an iodine atom, a methyl group or a methoxy group, $Z_2$ is a hydrogen atom;

when $Z_1$ is an amino group, $Z_2$ is a hydrogen atom or an amino group;

when $Z_1$ is a methyl group, a methoxy group or an amino group, $Z_1$ is in the 5-position; when $Z_1$ is an iodine atom, $Z_1$ is in the 5- or 7-position; and when $Z_1$ and $Z_2$ are both amino groups, $Z_1$ and $Z_2$ are in the 5- and 7-positions;

and the physiologically acceptable acid addition salt thereof.

DETAILED DESCRIPTION OF THE INVENTION

The indazole derivatives of the formula (I) of this invention are also represented by the following seven formulae (II), (III), (IV), (V), (VI), (VII) and (VIII):

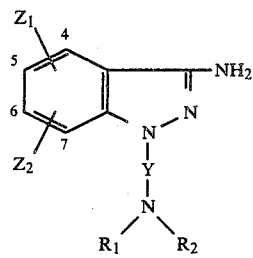
(II)

wherein
Y is a n-$C_{1-6}$ alkylene group or a propylene group having a $C_{1-4}$ alkyl group as a substituent; and $R_1$ and $R_2$ each independently is a $C_{1-6}$ alkyl group, and the

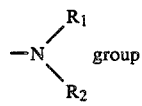
group may form a saturated heterocyclic ring selected from the group consisting of morpholino, pyrrolidino, piperidino, homopiperidino and piperazino groups, and the saturated heterocyclic ring except the morpholino group may have at least one $C_{1-4}$ alkyl group, hydroxyl group or chlorine atom as a substituent;

$Z_1$ is a chlorine atom, a bromine atom, an iodine atom, a hydroxyl group, an amino group, a $C_{1-3}$ alkyl group or a methoxy group;

$Z_2$ is a hydrogen atom or an amino group;

when $Z_1$ is a chlorine atom, a hydroxyl group, an iodine atom, a methyl group or a methoxy group, $Z_2$ is a hydrogen atom;

when $Z_1$ is an amino group, $Z_2$ is a hydrogen atom or an amino group;

when $Z_1$ is a methyl group, a methoxy group or an amino group, $Z_1$ is in the 5-position; when $Z_1$ is an iodine atom, $Z_1$ is in the 5- or 7-position; and when both $Z_1$ and $Z_2$ are amino groups, $Z_1$ and $Z_2$ are in the 5- and 7-position;

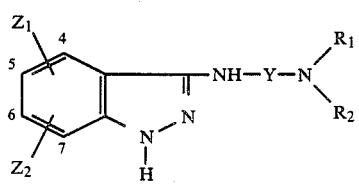
(III)

wherein Y, $R_1$, $R_2$, $Z_1$ and $Z_2$ are the same as defined in the formula (II);

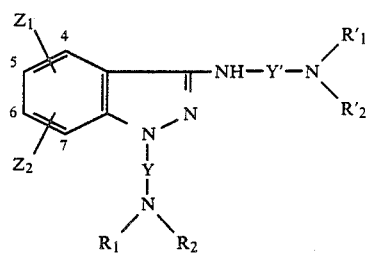
(IV)

wherein Y, $R_1$, $R_2$, $Z_1$ and $Z_2$ are the same as defined in the formula (II), and Y', $R'_1$ and $R'_2$ represent the same meaning as Y, $R_1$ and $R_2$, respectively;

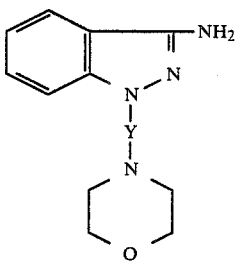
(V)

wherein Y is a n-$C_{1-6}$ alkylene group or a propylene group having a $C_{1-4}$ alkyl group as a substituent;

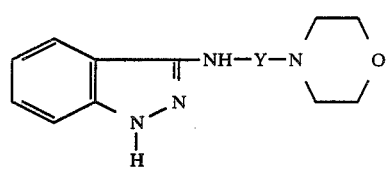
(VI)

wherein Y is the same as defined in the formula (V);

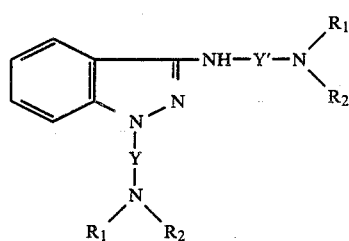
(VII)

wherein Y and Y' each independently is a n-$C_{1-6}$ alkylene group or a n-propylene group having a $C_{1-4}$ alkyl group as a substituent; and either

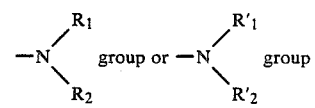

is a morpholino group, and the remaining

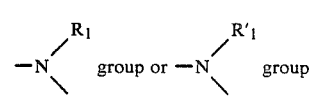

is a di-$C_{1-6}$ alkylamino group or a saturated heterocyclic ring selected from the group consisting of morpholino, pyrrolidino, piperidino, homopiperidino and piperazino groups, and the saturated heterocyclic ring except the morpholino group may have at least one $C_{1-4}$ alkyl group, hydroxyl group or halogen atom as a substituent;

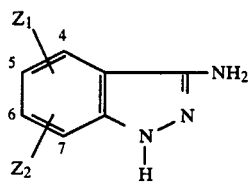
(VIII)

wherein
$Z_1$ is an iodine atom, a hydroxyl group or an amino group;
$Z_2$ is a hydrogen atom or an amino group;
when $Z_1$ is an iodine atom in the 5- or 7-position or a hydroxyl group, $Z_2$ is a hydrogen atom; and
when $Z_1$ is an amino group in the 5-position, $Z_2$ is an amino group in the 7-position.

Preferred Y groups in the formulae (II) and (III) include a n-propylene group, a n-hexylene group, a 3-methylpropylene group and a 3-(2-methylpropyl)propylene group.

Preferred

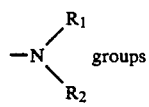 groups in the formulae (II) and (III) include a dimethylamino group, a diethylamino group, a di-n-propylamino group, a di-n-butylamino group, a pyrrolidino group, a piperidino group, a homopiperidino group, a piperazino group, a morpholino group, a 2-methylpiperidino group, a 2,6-dimethylpiperidino group, a 4-hydroxypiperidino group, a 4-chloropiperidino group and a 4-methylpiperazino group.

Preferred are compounds of the formula (II)
wherein Y is a n-propylene group;

is a 2-methylpiperidino group, a 2,6-dimethylpiperidino group, a 4-hydroxypiperidino group, a 4-chloropiperidino group, a homopiperidino group, a 4-methylpiperazino group, a pyrrolidino group or a morpholino group; $Z_1$ is a chlorine atom in the 5-position or a hydroxyl group in the 5-position; and $Z_2$ is a hydrogen atom;
wherein Y is a n-propylene group;

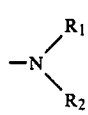

is a diethylamino group; $Z_1$ is a chlorine atom in the 4-, 6- or 7-position, an amino group in the 5-position, a methoxy group in the 5-position, a methyl group in the 5-position or an iodine atom in the 5- or 7-position; and $Z_2$ is a hydrogen atom;
wherein Y is a n-propylene group;

is a diethylamino group; $Z_1$ is a hydroxyl group in the 4-, 6- or 7-position; and $Z_2$ is a hydrogen atom; and
wherein Y is a n-propylene group;

is a diethylamino group; $Z_1$ is an amino group in the 5-position; and $Z_2$ is an amino group in the 7-position.

Preferred are compounds of the formula (III)
wherein Y is a n-propylene group;

is a 2-methylpiperidino group, a 2,6-dimethylpiperidino group, a 4-hydroxypiperidino group, a 4-chloropiperidino group, a homopiperidino group, a 4-methylpiperazino group, a pyrrolidino group or a morpholino group; $Z_1$ is a chlorine atom in the 5-position or a hydroxyl group in the 5-position; and $Z_2$ is a hydrogen atom;
wherein Y is a n-propylene group;

is a diethylamino group; $Z_1$ is a chlorine atom in the 4-, 6- or 7-position, an amino group in the 5-position, a methoxy group in the 5-position, a methyl group in the 5-position or an iodine atom in the 5- or 7-position; and $Z_2$ is a hydrogen atom;
wherein Y is a n-propylene group;

is a diethylamino group; $Z_1$ is a hydroxyl group in the 4-, 6- or 7-position; and $Z_2$ is a hydrogen atom; and
wherein Y is a n-propylene group;

is a diethylamino group; $Z_1$ is an amino group in the 5-position; and $Z_2$ is an amino group in the 7-position.

Preferred Y and Y' in the formula (IV) include an ethylene group, a n-propylene group, a n-hexylene group, a 3-methylpropylene group and a 3-(2-methylpropyl)propylene group.

Preferred

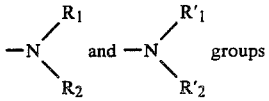

in the formula (IV) include a dimethylamino group, a diethylamino group, a di-n-propylamino group, a di-n-butylamino group, a pyrrolidino group, a piperidino group, a homopiperidino group, a 2-methylpiperidino group or a 4-methylpiperazino group.

Preferred $Z_1$ in the formula (IV) includes a hydroxyl group in 5-, 6- and 7-positions, an amino group in the 5-position, an iodine atom in 5- and 7-positions, and a chlorine atom.

Preferred are compounds of the formula (IV)
wherein Y is a n-propylene group;

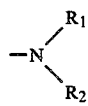

is a diethylamino group or a piperidino group; Y' is a n-propylene group, a n-hexylene group or a 3-methylpropylene group;

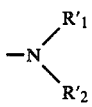

is a dimethylamino group, a diethylamino group, a di-n-propylamino group, a di-n-butylamino group or a piperidino group; $Z_1$ is a chlorine atom in the 5-position or a hydroxyl group in the 5-position; and $Z_2$ is a hydrogen atom;
wherein Y is a 3-methylpropyl group;

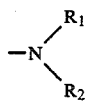

is a dimethylamino group or a piperidino group; Y' is a n-propylene group, a 3-methylpropylene group or a 3-(2-methylpropyl)propylene group;

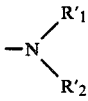

is a dimethylamino group, a diethylamino group or a piperidino group; $Z_1$ is a chlorine atom in the 5-position or a hydroxyl group in the 5-position; and $Z_2$ is a hydrogen atom;
wherein Y is a n-propylene group;

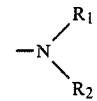

is a pyrrolidino group; Y' is a n-propylene group;

is a homopiperidino group, a methylpiperidino group or a 4-methylpiperazino group; $Z_1$ is a chlorine atom in the 5-position or a hydroxyl group in the 5-position; and $Z_2$ is a hydrogen atom;
wherein Y is a n-propylene group;

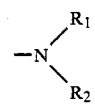

is a morpholino group; Y' is a n-propylene group;

is a diethylamino group, a 2,6-dimethylpiperidino group, a 4-chloropiperidino group or a 4-hydroxypiperidino group; $Z_1$ is a chlorine atom in the 5-position or a hydroxyl group in the 5-position; and $Z_2$ is a hydrogen atom;
wherein both Y and Y' are n-propylene groups; both

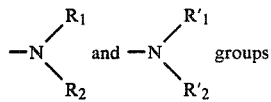

are diethylamino groups; $Z_1$ is a chlorine atom in the 4-, 6- or 7-position, a hydroxyl group in either 6- or 7-position, an amino group in the 5-position, or an iodine atom in the 5- or 7-position; and $Z_2$ is a hydrogen atom; and
wherein both Y and Y' are n-propylene groups; both

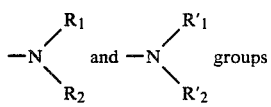

are diethylamino groups; $Z_1$ is an amino group in the 5-position; and $Z_2$ is an amino group in the 7-position.

Preferred Y groups in the formulae (V) and (VI) include an ethylene group, a n-propylene group and a 3-methylpropylene group.

Preferred Y in the formula (VII) includes an ethylene group, a n-propylene group, a hexylene group, a 3-methylpropylene group and a 3-(2-methylpropyl)propylene group.

Preferred remaining

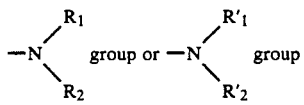 group or 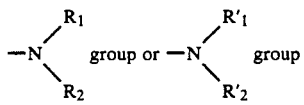 group in the formula (VII) includes a dimethylamino group, a diethylamino group, a di-n-propylamino group and a di-n-butylamino group.

Preferred are compounds of the formula (VII) wherein both Y and Y' are n-propylene groups;

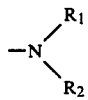

is a morpholino group; and

is a diethylamino group, a 2,6-dimethylpiperidino group, a 4-chloropiperidino group or a 4-hydroxypiperidino group; and
wherein both of Y and Y' are n-propylene groups;

is a di-n-butylamino group or a piperidino group; and

is a morpholino group.

Expemplary indazole derivatives of this invention include:

(1) 1-(3-Diethylaminopropyl)-3-amino-4-chloroindazole;
(2) 1-(3-Diethylaminopropyl)-3-amino-5-chloroindazole;
(3) 1-(3-Diethylaminopropyl)-3-amino-6-chloroindazole;
(4) 1-(3-Diethylaminopropyl)-3-amino-7-chloroindazole;
(5) 1-(3-Diethylaminopropyl)-3,5-diaminoindazole;
(6) 1-(3-Diethylaminopropyl)-3-amino-5-methoxyindazole;
(7) 1-(3-Diethylaminopropyl)-3-amino-5-methylindazole;
(8) 1-(3-Di-n-butylaminopropyl)-3-amino-5-chloroindazole;
(9) 1-(3-Dimethylaminobutyl)-3-amino-5-chloroindazole;
(10) 1-(3-Diethylamino-5-methylhexyl)-3-amino-5-chloroindazole;
(11) 1-(3-Piperidinopropyl)-3-amino-5-chloroindazole;
(12) 1-(6-Piperidinohexyl)-3-amino-5-chloroindazole;
(13) 1-(3-Piperidinobutyl)-3-amino-5-chloroindazole;
(14) 1-(3-Piperidino-5-methylhexyl)-3-amino-5-chloroindazole;
(15) 1-[3-(2-Methylpiperidino)propyl]-3-amino-5-chloroindazole;
(16) 1-[3-(2,6-Dimethylpiperidino)propyl]-3-amino-5-chloroindazole;
(17) 1-[3-(4-Hydroxypiperidino)propyl]-3-amino-5-chloroindazole;
(18) 1-[3-(4-Chloropiperidino)propyl]-3-amino-5-chloroindazole;
(19) 1-(3-Homopiperidinopropyl)-3-amino-5-chloroindazole;
(20) 1-[3-(4-Methylpiperazino)propyl]-3-amino-5-chloroindazole;
(21) 1-(3-Pyrrolidinopropyl)-3-amino-5-chloroindazole;
(22) 1-(3-Morpholinopropyl)-3-amino-5-chloroindazole;
(23) 1-(3-Diethylaminopropyl)-3-amino-4-hydroxyindazole;
(24) 1-(3-Diethylaminopropyl)-3-amino-5-hydroxyindazole;
(25) 1-(3-Diethylaminopropyl)-3-amino-6-hydroxyindazole;
(26) 1-(3-Diethylaminopropyl)-3-amino-7-hydroxyindazole;
(27) 1-(3-Diethylaminopropyl)-3-amino-5-iodoindazole;
(28) 1-(3-Diethylaminopropyl)-3-amino-7-iodoindazole;
(29) 1-(3-Diethylaminopropyl)-3,5,7-triaminoindazole;
(30) 1-(3-Di-n-butylaminopropyl)-3-amino-5-hydroxyindazole;
(31) 1-(3-Dimethylaminobutyl)-3-amino-5-hydroxyindazole;
(32) 1-(3-Diethylamino-5-methylhexyl)-3-amino-5-hydroxyindazole;
(33) 1-(3-Piperidinopropyl)-3-amino-5-hydroxyindazole;
(34) 1-(6-Piperidinohexyl)-3-amino-5-hydroxyindazole;
(35) 1-(3-Piperidinobutyl)-3-amino-5-hydroxyindazole;
(36) 1-(3-Piperidino-5-methylhexyl)-3-amino-5-hydroxyindazole;
(37) 1-[3-(2-Methylpiperidino)propyl]-3-amino-5-hydroxyindazole;
(38) 1-[3-(2,6-Dimethylpiperidino)propyl]-3-amino-5-hydroxyindazole;
(39) 1-[3-(4-Hydroxypiperidino)propyl]-3-amino-5-hydroxyindazole;
(40) 1-[3-(4-Chloropiperidino)propyl]-3-amino-5-hydroxyindazole;
(41) 1-(3-Homopiperidinopropyl)-3-amino-5-hydroxyindazole;
(42) 1-[3-(4-Methylpiperazino)propyl]-3-amino-5-hydroxyindazole;
(43) 1-(3-Pyrrolidinopropyl)-3-amino-5-hydroxyindazole;
(44) 1-(3-Morpholinopropyl)-3-amino-5-hydroxyindazole;
(45) 3-(3-Diethylaminopropylamino)-4-chloroindazole;
(46) 3-(3-Diethylaminopropylamino)-5-chloroindazole;
(47) 3-(3-Diethylaminopropylamino)-6-chloroindazole;
(48) 3-(3-Diethylaminopropylamino)-7-chloroindazole;
(49) 3-(3-Diethylaminopropylamino)-5-aminoindazole;
(50) 3-(3-Diethylaminopropylamino)-5-methoxyindazole;
(51) 3-(3-Diethylaminopropylamino)-5-methylindazole;
(52) 3-(3-Di-n-butylaminopropylamino)-5-chloroindazole;
(53) 3-(3-Dimethylaminobutylamino)-5-chloroindazole;
(54) 3-(3-Diethylamino-5-methylhexylamino)-5-chloroindazole;
(55) 3-(3-Piperidinopropylamino)-5-chloroindazole;
(56) 3-(6-Piperidinohexylamino)-5-chloroindazole;
(57) 3-(3-Piperidinobutylamino)-5-chloroindazole;
(58) 3-(3-Piperidino-5-methylhexylamino)-5-chloroindazole;
(59) 3-[3-(2-Methylpiperidino)propylamino]-5-chloroindazole;
(60) 3-[3-(2,6-Dimethylpiperidino)propylamino]-5-chloroindazole;
(61) 3-[3-(4-Hydroxypiperidino)propylamino]-5-chloroindazole;
(62) 3-[3-(4-Chloropiperidino)propylamino]-5-chloroindazole;
(63) 3-(3-Homopiperidinopropylamino)-5-chloroindazole;
(64) 3-[3-(4-Methylpiperadino)propylamino]-5-chloroindazole;
(65) 3-(3-Pyrrolidinopropylamino)-5-chloroindazole;
(66) 3-(3-Morpholinopropylamino)-5-chloroindazole;
(67) 3-(3-Diethylaminopropylamino)-4-hydroxyindazole;

(68) 3-(3-Diethylaminopropylamino)-5-hydroxyindazole;
(69) 3-(3-Diethylaminopropylamino)-6-hydroxyindazole;
(70) 3-(3-Diethylaminopropylamino)-7-hydroxyindazole;
(71) 3-(3-Diethylaminopropylamino)-5-iodoindazole;
(72) 3-(3-Diethylaminopropylamino)-7-iodoindazole;
(73) 3-(3-Diethylaminopropylamino)-5,7-diaminoindazole;
(74) 3-(3-Di-n-butylaminopropylamino)-5-hydroxyindazole;
(75) 3-(3-Dimethylaminobutylamino)-5-hydroxyindazole;
(76) 3-(3-Diethylamino-5-methylhexylamino)-5-hydroxyindazole;
(77) 3-(3-Piperidinopropylamino)-5-hydroxyindazole;
(78) 3-(6-Piperidinohexylamino)-5-hydroxyindazole;
(79) 3-(3-Piperidinobutylamino)-5-hydroxyindazole;
(80) 3-(3-Piperidino-5-methylhexylamino)-5-hydroxyindazole;
(81) 3-[3-(2-Methylpiperidino)propylamino]-5-hydroxyindazole;
(82) 3-[3-(2,6-Dimethylpiperidino)propylamino]-5-hydroxyindazole;
(83) 3-[3-(4-Hydroxypiperidino)propylamino]-5-hydroxyindazole;
(84) 3-[3-(4-Chloropiperidino)propylamino]-5-hydroxyindazole;
(85) 3-(3-Homopiperidinopropylamino)-5-hydroxyindazole;
(86) 3-[3-(4-Methylpiperadino)propylamino]-5-hydroxyindazole;
(87) 3-(3-Pyrrolidinopropylamino)-5-hydroxyindazole;
(88) 3-(3-Morpholinopropylamino)-5-hydroxyindazole;
(89) 1-(3-Diethylaminopropyl)-3-(3-diethylaminopropylamino)-4-chloroindazole;
(90) 1-(3-Diethylaminopropyl)-3-(3-diethylaminopropylamino)-5-chloroindazole;
(91) 1-(3-Diethylaminopropyl)-3-(6-diethylaminopropylamino)-6-chloroindazole;
(92) 1-(3-Diethylaminopropyl)-3-(3-diethylaminopropylamino)-7-chloroindazole;
(93) 1-(3-Diethylaminopropyl)-3-(3-diethylaminopropylamino)-5-aminoindazole;
(94) 1-(3-Diethylaminopropyl)-3-(3-diethylaminopropylamino)-5-methoxyindazole;
(95) 1-(3-Diethylaminopropyl)-3-(3-diethylaminopropylamino)-5-methylindazole;
(96) 1-(3-Diethylaminopropyl)-3-(3-piperidinopropylamino)-5-chloroindazole;
(97) 1-(3-Diethylaminopropyl)-3-(6-piperidinohexylamino)-5-chloroindazole;
(98) 1-(3-Diethylaminopropyl)-3-(3-di-n-butylaminopropylamino)-5-chloroindazole;
(99) 1-(3-Diethylaminopropyl)-3-(3-piperidinobutylamino)-5-chloroindazole;
(100) 1-(3-Piperidinopropyl)-3-(3-diethylaminopropylamino)-5-chloroindazole;
(101) 1-(3-Piperidinopropyl)-3-(3-piperidinopropylamino)-5-chloroindazole;
(102) 1-(3-Piperidinopropyl)-3-(6-piperidinohexylamino)-5-chloroindazole;
(103) 1-(3-Piperidinopropyl)-3-(3-piperidinobutylamino)-5-chloroindazole;
(104) 1-(3-Piperidinobutyl)-3-(3-diethylaminopropylamino)-5-chloroindazole;
(105) 1-(3-Piperidinobutyl)-3-(3-piperidinopropylamino)-5-chloroindazole;
(106) 1-(3-Piperidinobutyl)-3-(3-piperidino-5-methylhexylamino)-5-chloroindazole;
(107) 1-(3-Piperidinobutyl)-3-(3-dimethylaminobutylamino)-5-chloroindazole;
(108) 1-(3-Dimethylaminobutyl)-3-(3-diethylaminopropylamino)-5-chloroindazole;
(109) 1-(3-Dimethylaminobutyl)-3-(3-piperidinopropylamino)-5-chloroindazole;
(110) 1-(3-Dimethylaminobutyl)-3-(3-piperidinobutylamino)-5-chloroindazole;
(111) 1-(3-Dimethylaminobutyl)-3-(3-diethylamino-5-methylhexylamino)-5-chloroindazole;
(112) 1-(3-Pyrrolidinopropyl)-3-(3-homopiperidinopropylamino)-5-chloroindazole;
(113) 1-(3-Pyrrolidinopropyl)-3-[3-(2-methylpiperidino)propylamino]-5-chloroindazole;
(114) 1-(3-Pyrrolidinopropyl)-3-[3-(4-methylperazino)propylamino]-5-chloroindazole;
(115) 1-(3-Morpholinopropyl)-3-(3-diethylaminopropylamino)-5-chloroindazole;
(116) 1-(3-Morpholinopropyl)-3-[3-(2,6-dimethylpiperidino)propylamino]-5-chloroindazole;
(117) 1-(3-Morpholinopropyl)-3-[3-(4-chloropiperidino)propylamino]-5-chloroindazole;
(118) 1-(3-Morpholinopropyl)-3-[3-(4-hydroxypiperidino)propylamino]-5-chloroindazole;
(119) 1-(3-Diethylaminopropyl)-3-(3-diethylaminopropylamino)-4-hydroxyindazole;
(120) 1-(3-Diethylaminopropyl)-3-(3-diethylaminopropylamino)-5-hydroxyindazole;
(121) 1-(3-Diethylaminopropyl)-3-(3-diethylaminopropylamino)-6-hydroxyindazole;
(122) 1-(3-Diethylaminopropyl)-3-(3-diethylaminopropylamino)-7-hydroxyindazole;
(123) 1-(3-Diethylaminopropyl)-3-(3-diethylaminopropylamino)-5-iodoindazole;
(124) 1-(3-Diethylaminopropyl)-3-(3-diethylaminopropylamino)-7-iodoindazole;
(125) 1-(3-Diethylaminopropyl)-3-(3-diethylaminopropylamino)-5,7-diaminoindazole;
(126) 1-(3-Diethylaminopropyl)-3-(3-piperidinopropylamino)-5-hydroxyindazole;
(127) 1-(3-Diethylaminopropyl)-3-(6-piperidinohexylamino)-5-hydroxyindazole;
(128) 1-(3-Diethylaminopropyl)-3-(3-di-n-butylaminopropylamino)-5-hydroxyindazole;
(129) 1-(3-Diethylaminopropyl)-3-(3-piperidinobutylamino)-5-hydroxyindazole;
(130) 1-(3-Piperidinopropyl)-3-(3-diethylaminopropylamino)-5-hydroxyindazole;
(131) 1-(3-Piperidinopropyl)-3-(3-piperidinopropylamino)-5-hydroxyindazole;
(132) 1-(3-Piperidinopropyl)-3-(6-piperidinohexylamino)-5-hydroxyindazole;
(133) 1-(3-Piperidinopropyl)-3-(3-piperidinobutylamino)-5-hydroxyindazole;
(134) 1-(3-Piperidinobutyl)-3-(3-diethylaminopropylamino)-5-hydroxyindazole;
(135) 1-(3-Piperidinobutyl)-3-(3-piperidinopropylamino)-5-hydroxyindazole;
(136) 1-(3-Piperidinobutyl)-3-(3-piperidino-5-methylhexylamino)-5-hydroxyindazole;
(137) 1-(3-Piperidinobutyl)-3-(3-dimethylaminobutylamino)-5-hydroxyindazole;
(138) 1-(3-Dimethylaminobutyl)-3-(3-diethylaminopropylamino)-5-hydroxyindazole;
(139) 1-(3-Dimethylaminobutyl)-3-(3-piperidinopropylamino)-5-hydroxyindazole;
(140) 1-(3-Dimethylaminobutyl)-3-(3-piperidinotbutylamino)-5-hydroxyindazole;
(141) 1-(3-Dimethylaminobutyl)-3-(3-diethylamino-5-methylhexylamino)-5-hydroxyindazole;
(142) 1-(3-Pyrrolidinopropyl)-3-(3-homopiperidinopropylamino)-5-hydroxyindazole;
(143) 1-(3-Pyrrolidinopropyl)-3-[3-(2-methylpiperidino)propylamino]-5-hydroxyindazole;
(144) 1-(3-Pyrrolidinopropyl)-3-[3-(4-methylperazino)propylamino]-5-hydroxyindazole;
(145) 1-(3-Morpholinopropyl)-3-(3-diethylaminopropylamino)-5-hydroxyindazole;
(146) 1-(3-Morpholinopropyl)-3-[3-(2,6-dimethylpiperidino)propylamino]-5-hydroxyindazole;
(147) 1-(3-Morpholinopropyl)-3-[3-(4-chloropiperidino)propylamino]-5-hydroxyindazole;
(148) 1-(3-Morpholinopropyl)-3-[3-(4-hydroxypiperidino)propylamino]-5-hydroxyindazole;
(149) 1-(3-Morpholinopropyl)-3-aminoindazole;
(150) 1-(3-Morpholinobutyl)-3-aminoindazole;
(151) 1-(2-Morpholinoethyl)-3-aminoindazole;
(152) 3-(3-Morpholinopropylamino)indazole;
(153) 3-(3-Morpholinobutylamino)indazole;
(154) 3-(2-Morpholinoethylamino)indazole;
(155) 1-(3-Morpholinopropyl)-3-(3-diethylaminopropylamino)indazole;
(156) 1-(3-Morpholinopropyl)-3-[3-(2,6-dimethylpiperidino)propylamino]indazole;
(157) 1-(3-Morpholinopropyl)-3-[3-(4-chloropiperidino)propylamino]indazole;
(158) 1-(3-Morpholinopropyl)-3-[3-(4-hydroxypiper- -continued idino)propylamino]indazole;
(159) 1-(3-Di-n-butylaminopropyl)-3-(3-morpholino-propylamino)indazole;
(160) 1-(3-Piperidinopropyl)-3-(3-morpholinopropyl-amino)indazole;
(161) 3-Amino-4-hydroxyindazole;
(162) 3-Amino-5-hydroxyindazole;
(163) 3-Amino-6-hydroxyindazole;
(164) 3-Amino-7-hydroxyindazole;
(165) 3-Amino-5-iodoindazole;
(166) 3-Amino-7-iodoindazole;
(167) 3,5,7-Triaminoindazole;

and the physiologically acceptable acid addition salts thereof.

With respect to the following reactions for the preparation of compounds of the formulae (II) to (VIII) and their precursors, it is a matter of routine for experts to find out proper reaction conditions especially with respect to the amount of the reaction components, the reaction medium (if necessary), the acid acceptor (if necessary) and its amount and the reaction temperature.

Most starting compounds used for preparing the indazole derivatives of this invention are known compounds, and accordingly, they can be easily prepared by experts using chemical reagents on market. For example, 3-aminoindazoles whose benzene ring has substituents can be easily prepared in accordance with the methods as described in C. E. Kwartler et al., J. Amer. Chem. Soc., 65, 1804 (1943). Further ω-halogenoalkylamines can be prepared in accordance with the methods as described in H. C. Brill, J. Amer. Chem. Soc., 47, 1134 (1925) and C. S. Marvel et al., J. Amer. Chem. Soc., 49, 2299 (1927) by using the corresponding dihalogenoalkyl compounds. Furthermore, aminoacrylamides can be prepared in accordance with the methods as described in Ciba Ltd. Brit. 746–747, Mar. 21, 1956 by using the corresponding amines and 3-chloropropionyl chloride.

Compounds of the formula (II) of this invention can be prepared by reacting 3-aminoindazole having substituents in the benzene ring (IX) with phthalic anhydride to obtain 3-phthalimidoindazole whose benzene ring in the indazole ring has substituents, reacting the 3-phthalimidoindazole with an ω-halogenoalkylamine of the formula (X) to give a 1-(aminoalkyl)-3-phthalimidoindazole whose benzene ring in the indazole ring has substituents, and then treating the 1-(aminoalkyl)-3-phthalimidoindazole with hydrazine hydrate to release the protective group of the 3-position amino group in accordance with the following equations:

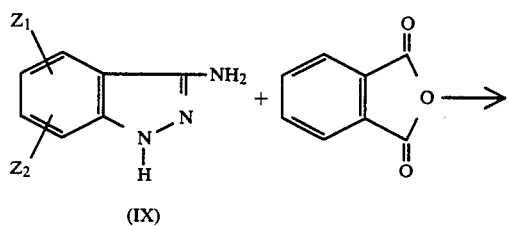

(A)

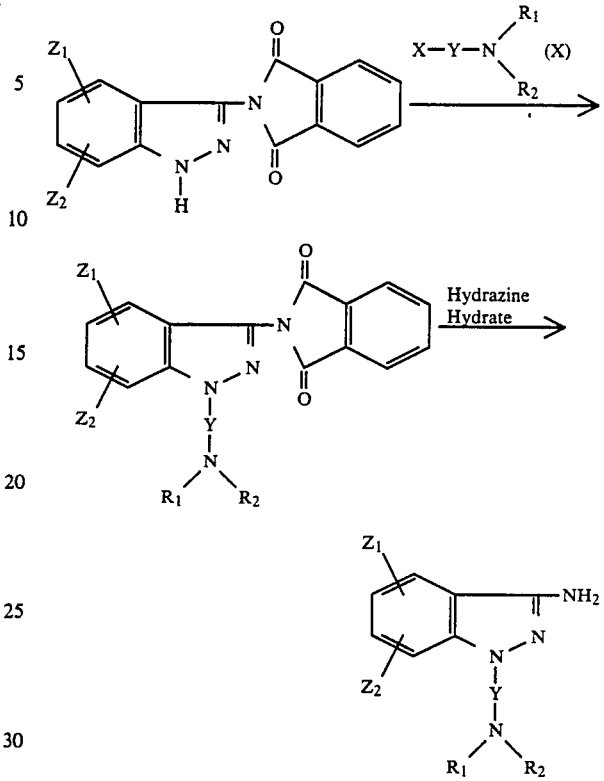

wherein Y, $R_1$ and $R_2$ are the same as defined in the formula (II); X is a chlorine atom, a bromine atom or an iodine atom; $Z_1$ is a chlorine atom in the 4-, 5-, 6- or 7-position, a methyl group in the 5-position, a methoxy group in the 5-position or an iodine atom in the 5- or 7-position; and $Z_2$ is a hydrogen atom.

The reaction between the 3-aminoindazole whose benzene ring has substituents and phthalic anhydride can be carried out in the presence of a reaction medium. Exemplary reaction media which can be employed include polar organic solvents such as dioxane, diethyl ether, tetrahydrofuran, ethyl alcohol, ethylene glycol, acetonitrile, dimethyl sulfoxide and N,N-dimethylformamide.

The reaction between the 3-aminoindazole whose benzene ring has substituents and phthalic anhydride can be carried out at a temperature of from about 10° C. to about 200° C., preferably from about 60° C. to about 150° C.

The reaction between the 3-phthalimidoindazole whose benzene ring in the indazole ring has substituents and the ω-halogenoalkylamine (IX) can be carried out in the presence of a reaction medium and an acid acceptor. Exemplary reaction media which can be employed include non-proton polar solvents such as acetonitrile, dimethyl sulfoxide and N,N-dimethylformamide; alcohols such as methyl alcohol, ethyl alcohol, n-propyl alcohol, isopropyl alcohol and n-butyl alcohol. Exemplary acid acceptors which can be employed include tertiary amines such as triethylamine; alkali metal carbonates such as potassium carbonate; alkali metal bicarbonates such as sodium hydrogencarbonate; and alkali metal hydroxides such as sodium hydroxide.

Then ω-halogenoalkylamines (X) which can be employed include 1-(2-chloroethyl)piperidine, 1-(2-bromoethyl)piperidine, 1-(2-iodoethyl)piperidine, 1-(3-chloropropyl)piperidine, 1-(3-bromopropyl)piperidine, 1-(3-iodopropyl)piperidine, 1-(6-chlorohexyl)piperidine, 1-(6-bromohexyl)piperidine, 1-(6-iodohexyl)piperidine, 1-(3-chloropropyl)pyrrolidine, 1-(3-bromopropyl)pyrrolidine, 1-(3-iodopropyl)pyrrolidine, 1-(3-chloropropyl)homopiperidine, 1-(3-bromopropyl)homopiperidine, 1-(3-iodopropyl)homopiperinde, 1-(3-chloropropyl)-2-methylpiperidine, 1-(3-bromopropyl)-2-methylpiperidine, 1-(3-iodopropyl)-2-methylpiperidine, 1-(3-chloropropyl)-2,6-dimetehylpiperidine, 1-(3-bromopropyl)-2,6-dimethylpiperidine, 1-(3-iodopropyl)-2,6-dimethylpiperidine, 1-(3-chloropropyl)- 4-hydroxypiperidine, 1-(3-bromopropyl)-4-hydroxypiperidine, 1-(3-iodopropyl)-4-hydroxypiperidine, 1-(3-chloropropyl)-4-chloropiperidine, 1-(3-bromopropyl)-4-chloropiperidine, 1-(3-iodopropyl)-4-chloropiperidine, N,N-diethyl-3-chloropropylamine, N,N-diethyl-3-bromopropylamine, N,N-diethyl-3-iodopropylamine, N-(3-chloropropyl)dibutylamine, N-(3-bromopropyl)dibutylamine, N-(3-iodopropyl)dibutylamine, N,N-di-n-butyl-3-chloropropylamine, N,N-di-n-butyl-3-bromopropylamine, N,N-di-n-butyl-3-iodopropylamine, N,N-dimethyl-2-chloroethylamine, N,N-dimethyl-2-bromoethylamine, N,N-di-methyl-2-iodoethylamine, 1-(3-chloropropyl)-4-methylpiperazine, 1-(3-bromopropyl)-4-methylpiperazine, 1-(3-iodopropyl)-4-methylpiperazine, 1-(1-methyl-3-chloropropyl)piperidine, 1-(1-methyl-3-bromopropyl)piperidine, 1-(1-methyl-3-iodopropyl)piperidine, 1-(1-isobutyl-3-chloropropyl)piperidine, 1-(1-isobutyl-3-bromopropyl)piperidine, 1-(1-isobutyl-3-iodopropyl)piperidine, N,N-diethyl-3-chloro-1-methylpropylamine, N,N-diethyl-3-bromo-1-methylpropylamine, N,N-diethyl-3-iodo-1-methylpropylamine, N,N-diethyl-3-chloro-1-isobutylpropylamine, N,N-diethyl-3-bromo-1-isobutylpropylamine, N,N-diethyl-3-iodo-1-isobutylpropylamine, N,N-dimethyl-3-chloro-1-methylpropylamine, N,N-dimethyl-3-bromo-1-methylpropylamine, N,N-dimethyl-3-iodo-1-methylpropylamine, N,N-dimethyl-3-chloro-1-isobutylpropylamine, N,N-dimethyl-3-bromo-1-isobutylpropylamine, N,N-dimethyl-3-iodo-1-isobutylpropylamine, 1-(2-chloroethyl)morpholine, 1-(2-bromoethyl)morpholine, 1-(2-iodoethyl)morpholine, 1-(3-chloropropyl)morpholine, 1-(3-bromopropyl)morpholine, 1-(3-iodopropyl)morpholine, 1-(1-methyl-3-chloropropyl)morpholine, 1-(1-methyl-3-bromopropyl)morpholine and 1-(1-methyl-3-iodopropyl)morpholine.

The reaction between the 3-phthalimidoindazole whose benzene ring in the indazole ring has substituents and the ω-halogenoalkylamine can be carried out at a temperature of from about 10° C. to about 200° C., preferably from about 80° C. to about 120° C.

The reaction between the 1-(aminoalkyl)-3-phthalimidoindazole whose benzene ring in the indazole ring as substituents and hydrazine hydrate can be carried out in the presence of a reaction medium. Exemplary reaction media which can be employed include alcohols such as methyl alcohol and ethyl alcohol; glycols such as ethylene glycol and propylene glycol; diglyme and triethanolamine. Preferably this reaction can be carried out under cooling with ice.

Compounds of the formula (II) of this invention, wherein $Z_1$ is a hydroxyl group in the 4-, 6- or 7-position and $Z_2$ is a hydrogen atom can be prepared by reacting a 1-(aminoalkyl)-3-amino-chloroindazole whose chlorine atom is in the 4-, 6- or 7-position with magnesium powder, isopropyl bromide, oxygen gas and carbon dioxide gas in the presence of a reaction medium. Exemplary reaction media which can be employed include ethers such as diethyl ether, tetrahydrofuran and dioxane. This reaction can be carried out at a temperature of from about 0° C. to about 100° C., preferably from about 0° C. to about 10° C.

Compounds of the formula (II) of this invention, wherein $Z_1$ is a hydroxyl group in the 5-position and $Z_2$ is a hydrogen atom can be prepared by sulfonating a 1-(aminoalkyl)-3-aminoindazole with sulfuric acid, and then reacting the sulfonated 1-(aminoalkyl)-3-aminoindazole with an alkali compound in the presence of a reaction medium. The sulfonation reaction can be carried out at a temperature of from about 0° C. to about 100° C., preferably from about 50° C. to about 100° C. The reaction between the sulfonated 1-(aminoalkyl)-3-aminoindazole and the alkali compound can be carried out at a temperature of from about 0° C. to about 300° C., preferably from about 250° C. to about 300° C. Exemplary alkali compounds which can be employed include metal hydroxides such as sodium hydroxide, potassium hydroxide and calcium hydroxide. The reaction medium which can be employed is water.

Compounds of the formula (II) of this invention, wherein $Z_1$ is an amino group in the 5-position and $Z_2$ is a hydrogen atom can be prepared by reacting a 1-(aminoalkyl)-3-aminoindazole with both nitric acid and sulfuric acid in the absence of a reaction medium to obtain a 1-(aminoalkyl)-3-amino-5-nitroindazole, and then reducing the 1-(aminoalkyl)-3-amino-5-nitroindazole with both iron powder and hydrochloric acid in the presence of a reaction medium to give a 1-(aminoalkyl)-3,5-diaminoindazole. The reaction among the 1-(aminoalkyl)-3-aminoindazole, nitric acid and sulfuric acid can be carried out at a temperature of from about −20° C. to about 20° C., preferably from about 0° C. to about 10° C. The reduction reaction of the 1-(aminoalkyl)-3-amino-5-nitroindazole can be carried out at a temperature of from about 0° C. to about 200° C., preferably from about 0° C. to about 80° C. Exemplary reaction media which can be employed in the reduction reaction include water and alcohols such as methyl alcohol, ethyl alcohol, n-propyl alcohol, isopropyl alcohol and n-butyl alcohol.

Compounds of the formula (II) of this invention, wherein both $Z_1$ and $Z_2$ are amino groups in the 5- and 7-positions can be prepared by reacting a 1-(aminoalkyl)-3-aminoindazole with both nitric acid and sulfuric acid in the absence of a reaction medium to obtain a 1-(aminoalkyl)-3-amino-5,7-dinitroindazole, and then reducing the 1-(aminoalkyl)-3-amino-5,7-dinitroindazole with a reducing agent to give a 1-(aminoalkyl)-3,5,7-triaminoindazole. The reaction among the 1-(aminoalkyl)-3-aminoindazole, nitric acid and sulfuric acid can be carried out at a temperature of from about 0° C. to about 100° C., preferably from about 0° C. to about 10° C. The reduction reaction of the 1-(aminoalkyl)-3-amino-5,7-dinitroindazole can be carried out at a temperature of from about 0° C. to about 200° C., preferably from about 50° C. to about 80° C. Exemplary reducing agents which can be employed in the reduction reaction include iron-hydrochloric acid, zinc-hydrochloric acid, lithium aluminum hydride and hydrogen gas.

Another method of preparing compounds of the formula (II) comprises reacting a 2-cyano-1-(aminoalkylamino)benzene whose benzene ring has substituents (XI) with sodium nitrite and hydrochloric acid in water to obtain a nitroso compound, reducing the nitroso compound with stannous chloride and hydrochloric acid, and then treating the reactant with hydrochloric acid in accordance with the following equations:

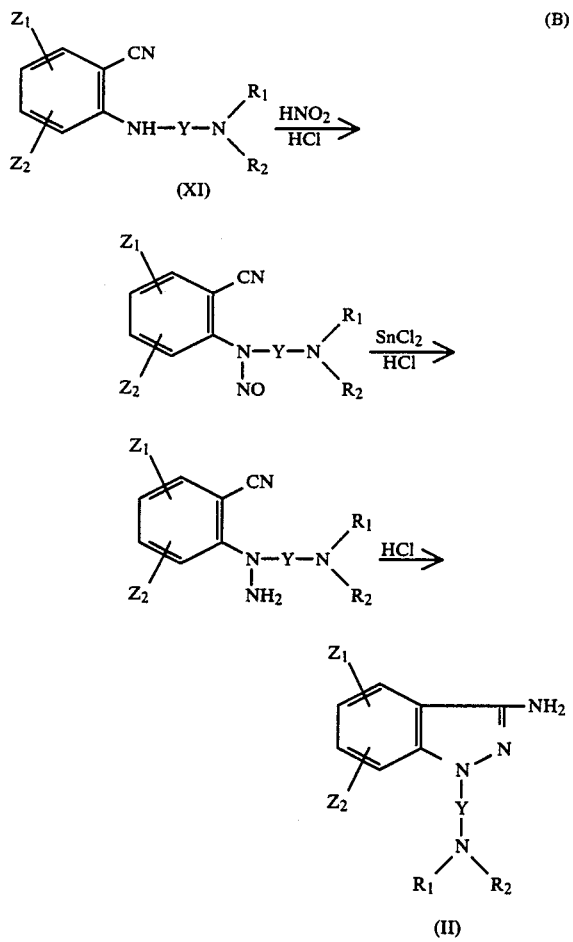

(B)

wherein Y, $R_1$ and $R_2$ are the same as defined in the formula (II), and $Z_1$ and $Z_2$ are the same as defined in the formula (IX).

Reaction (B) can be carried out in a manner which corresponds to C. E. Kwartler et al., J. Am. Chem. Soc., 65, 1804 (1943). It can be carried out at a temperature of from about −20° C. to about 20° C., preferably from about 0° C. to 10° C.

Compounds of the formula (III) of this invention can be prepared by reacting a 3-aminoindazole having substituents in the benzene ring (IX) with an ω-halogenoalkylamine of the formula (X) in accordance with the following equation:

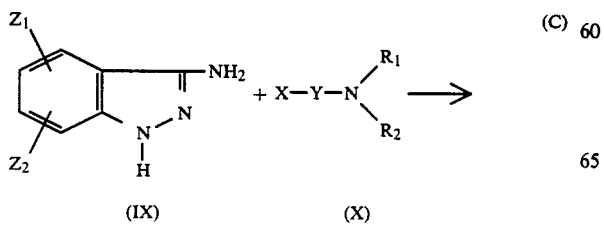

(C)

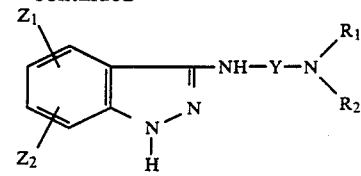

wherein Y, $R_1$ and $R_2$ are the same as defined in the formula (II), $Z_1$ and $Z_2$ are the same as defined in the formula (IX); and X is a chlorine atom, a bromine atom or an iodine atom.

The 3-aminoindazoles having substituents in the benzene ring (IX) and the ω-halogenoalkylamines (X) which can be employed in the reaction (C) include the same 3-aminoindazoles and ω-halogenoalkylamines as the ones used in the reaction (A).

The reaction (C) can be carried out in the presence of a reaction medium. Exemplary reaction media which can be employed include non-proton polar solvents such as acetonitrile, dimethyl sulfoxide and N,N-dimethylformamide; and alcohols such as methyl alcohol, ethyl alcohol, n-propyl alcohol, isopropyl alcohol and n-butyl alcohol.

The reaction (C) can be carried out in the presence of an acid acceptor for hydrogen halides generated in the reaction. Exemplary acid acceptors which can be employed include tertiary amines such as triethylamine; alkali metal carbonates such as potassium carbonate; alkali metal bicarbonates such as sodium hydrogencarbonate; and alkali metal hydroxides such as sodium hydroxide.

The reaction (C) can be carried out at a temperature of from about 10° C. to about 200° C., preferably from about 80° C. to about 120° C.

Compounds of the formula (III) of this invention, especially compounds of the formula (XIII) can be prepared in accordance with the following equations:

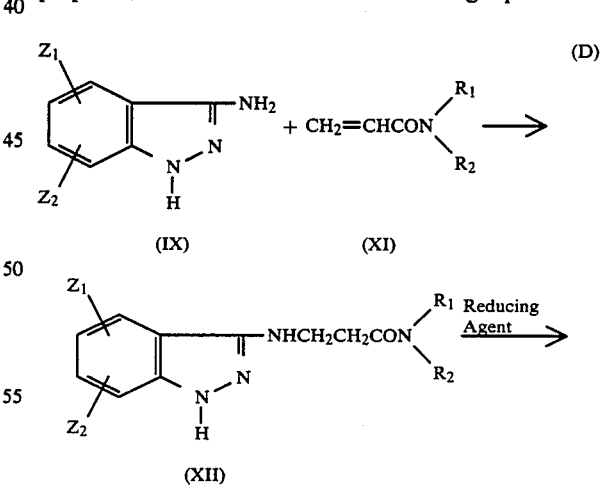

(D)

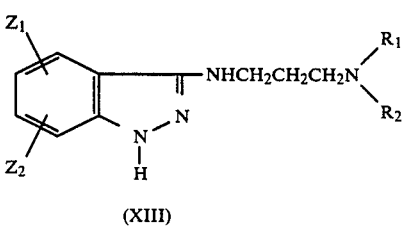

wherein $R_1$ and $R_2$ are the same as defined in the formula (II), and $Z_1$ and $Z_2$ are the same as defined in the formula (IX).

The reaction between the 3-aminoindazole (IX) and the aminoacrylamide of the formula (XI) can be carried out either in the absence or presence of a reaction medium. Exemplary reaction media which can be employed include polar organic solvents such as dioxane, diethyl ether, tetrahydrofuran, ethyl alcohol, ethylene glycol, acetonitrile, dimethyl sulfoxide and N,N-dimethylformamide.

The reaction between the 3-aminoindazole (XI) and the aminoacrylamide (XI) can be carried out at a temperature of from about 10° C. to about 200° C., preferably from about 60° C. to about 100° C.

The reduction reaction between the compound of the formula (XII) and the reducing agent can be carried out in the presence of a reaction medium. Exemplary reaction media include ethers such as ethyl ether, tetrahydrofuran and dioxane. Exemplary reducing agents which can be employed include lithium aluminum hydride, sodium boron hydride and diborane.

The reduction reaction of the compound (XII) can be carried out at a temperature of from about 10° C. to about 100° C., preferably from about 50° C. to about 80° C.

Compounds of the formula (III) of this invention, wherein $Z_1$ is a hydroxyl group in the 4-, 6- or 7-position and $Z_2$ is a hydrogen atom can be prepared by reacting a 3-(aminoalkylamino)-chloroindazole whose chlorine atom is in the 4-, 6- or 7-position with magnesium powder, isopropyl bromide, oxygen gas and carbon dioxide gas in the presence of a reaction medium. Exemplary reaction media which can be employed include ethers such as diethyl ether, tetrahydrofuran and dioxane. This reaction can be carried out at a temperature of from about 0° C. to about 100° C., preferably from about 0° C. to about 10° C.

Compounds of the formula (II) of this invention, wherein $Z_1$ is a hydroxyl group in the 5-position and $Z_2$ is a hydrogen atom can be prepared by sulfonating a 3-(aminoalkylamino)indazole with sulfuric acid, and then reacting the sulfonated compound with an alkali compound in the presence of a reaction medium. The sulfonation reaction can be carried out at a temperature of from about 0° C. to about 100° C., preferably from about 50° C. to about 100° C. The reaction between the sulfonated compound and the alkali compound can be carried out at a temperature of from about 0° C. to about 300° C., preferably from about 250° C. to about 300° C. Exemplary alkali compounds which can be employed include metal hydroxides such as sodium hydroxide, potassium hydroxide and calcium hydroxide. The reaction medium which can be employed is water.

Compounds of the formula (III) of this invention, wherein $Z_1$ is an amino group in the 5-position and $Z_2$ is a hydrogen atom can be prepared by reacting a 3-(aminoalkylamino)indazole with both nitric acid and sulfuric acid in the absence of a reaction medium to obtain a 3-(aminoalkylamino)-5-nitroindazole, and then reducing the 3-(aminoalkylamino)-5-nitroindazole with both iron powder and hydrochloric acid in the presence of a reaction medium to give a 3-(aminoalkylamino)-5-aminoindazole. The reaction among the 3-(aminoalkylamino)indazole, nitric acid and sulfuric acid can be carried out at a temperature of from about −20° C. to about 20° C., preferably from about 0° C. to about 10° C. The reduction reaction of the 3-(aminoalkylamino)-5-nitroindazole can be carried out at a temperature of from about 0° C. to about 200° C., preferably from about 0° C. to about 80° C. Exemplary reaction media which can be employed in the reduction reaction include water and alcohols such as methyl alcohol, ethyl alcohol, n-propyl alcohol, isopropyl alcohol and n-butyl alcohol.

Compounds of the formula (III) of this invention, wherein both $Z_1$ and $Z_2$ are amino groups in the 5 and 7-positions can be prepared by reacting a 3-(aminoalkylamino)indazole with both nitric acid and sulfuric acid in the absence of a reaction medium to obtain a 3-(aminoalkylamino)-5,7-dinitroindazole, and then reducing the 3-(aminoalkylamino)-5,7-dinitroindazole with a reducing agent to give a 3-(aminoalkylamino)-5,7-diaminoindazole. The reaction among the 3-(aminoalkylamino)indazole, nitric acid and sulfuric acid can be carried out at a temperature of from about 0° C. to about 100° C., preferably from about 0° C. to about 10° C. The reduction reaction of the 3-(aminoalkylamino)-5,7-dinitroindazole can be carried out at a temperature of from about 0° C. to about 200° C., preferably from about 50° C. to about 80° C. Exemplary reducing agents which can be employed in the reduction reaction include iron-hydrochloric acid, zinchydrochloric acid, lithium aluminum hydride and hydrogen gas.

Compounds of the formula (III) of this invention can also be prepared by reacting a 3-halogenoindazole having substituents in the benzene ring (XIV) with an aminoalkylamine compound (XV) in the presence of a reaction medium and an acid acceptor in accordance with the following equation:

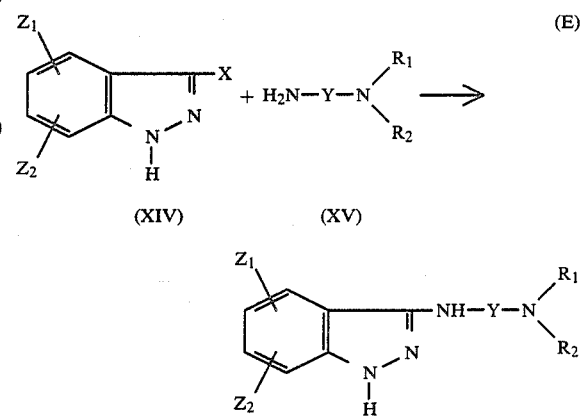

wherein Y, $R_1$ and $R_2$ are the same as defined in the formula (II); $Z_1$ and $Z_2$ are the same as defined in the formula (IX), and X is a chlorine atom, a bromine atom or an iodine atom.

The 3-halogenoindazole having substituents in the benzene ring (XIV) can be prepared by the method described in Org. Syntheses, Coll. Vol. III, 475 (1955).

The aminoalkylamine compound (XV) can be prepared by the ordinary synthetic method described in Org. Syntheses, Coll. Vol. II, 83 (1943), by using halogenoalkyl compounds which correspond to the desired aminoalkylamines (XV).

Exemplary reaction media which can be employed in the reaction (E) include non-proton polar solvents such as acetonitrile, dimethyl sulfoxide and N,N-dimethylformamide; and halogenated hydrocarbons such as chloroform, methylene chloride, carbon tetrachloride and 1,2-dichloroethane.

Exemplary acid acceptors which can be employed in the reaction (E) include tertiary amines such as pyridine and triethylamine; alkali metal carbonates such as potassium carbonate; alkali metal bicarbonates such as sodium hydrogencarbonate; and alkali metal hydroxides such as sodium hydroxide.

The reaction (E) can be carried out at a temperature of from about 0° C. to about 200° C., preferably from about 35° C. to about 120° C.

Another method for preparing the compound of the formula (III) is to react a 2-amino-1-(aminoalkyl)benzamide having substituents in the benzene ring of the formula (XVI) with sodium nitrite and hydrochloric acid in water, reduce the reactant with sulfurous acid, and then treat the reactant with hydrochloric acid in accordance with the following equations:

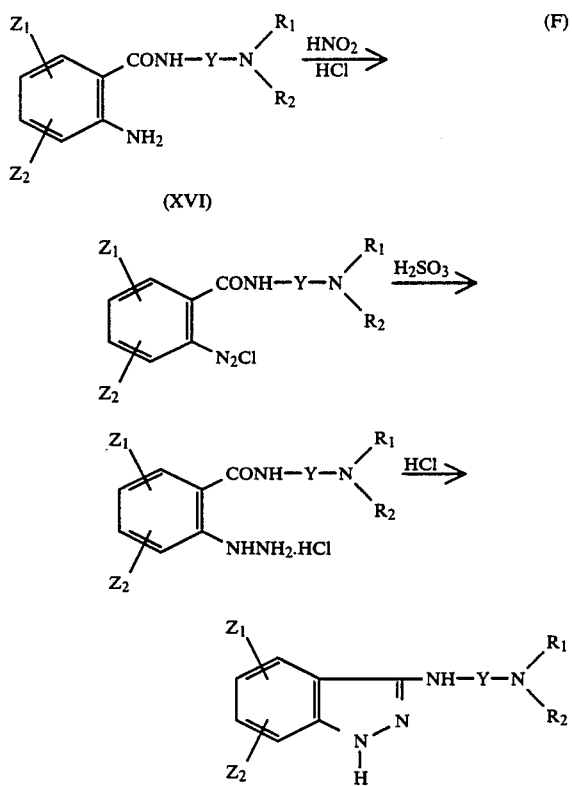

wherein Y, $R_1$ and $R_2$ are the same as defined in the formula (II), and $Z_1$ and $Z_2$ are the same as defined in the formula (IX).

The 2-amino-1-(aminoalkyl)benzene whose benzene ring has substituents (XVI) can be prepared from a 2-amino-1-(aminoalkyl)benzene in accordance with the method as described in Org. Syntheses, Coll. Vol. III, 475(1955).

The reaction (F) can be carried out at a temperature of from about −20° C. to about 20° C., preferably from about 0° C. to 10° C.

Compounds of the formula (IV) can be prepared by reacting an 1-(aminoalkyl)-3-aminoindazole whose benzene ring has substituents of the formula (II) with an ω-halogenoalkylamine compound of the formula (XVII) in the presence of an acid acceptor in accordance with the following equation:

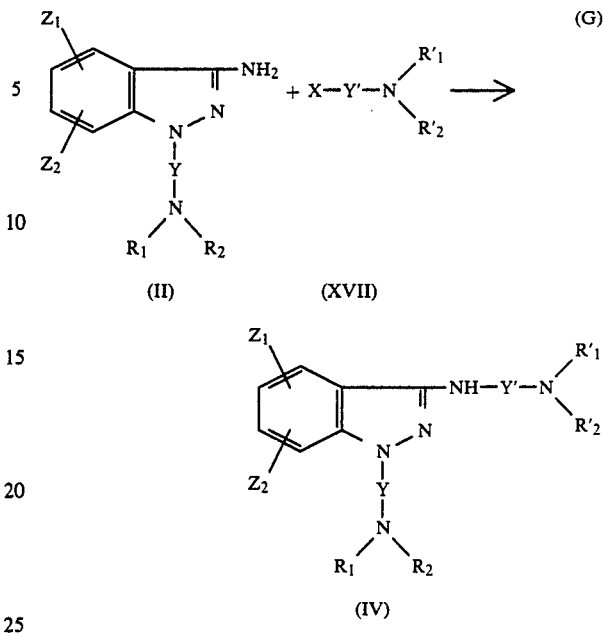

wherein Y, $R_1$, $R_2$, Y′, $R'_1$ and $R'_2$ are the same as defined in the formula (IV); $Z_1$ and $Z_2$ are the same as defined in the formula (IX); and X is a chlorine atom, a bromine atom or an iodine atom.

The ω-halogenoalkylamines (XVII) which can be employed in the reaction (G) include the same ω-halogenoalkylamines as the ones used in the reaction (A) of this invention.

The reaction (G) can be carried out in the presence of a reaction medium. Exemplary reaction media which can be employed include non-proton polar solvents such as acetonitrile, dimethyl sulfoxide and N,N-dimethylformamide; and alcohols such as methyl alcohol, ethyl alcohol, n-propyl alcohol, isopropyl alcohol and n-butyl alcohol.

Exemplary acid acceptors which can be employed in the reaction (G) include tertiary amines such as triethylamine; alkali metal carbonates such as potassium carbonate; alkali metal bicarbonates such as sodium hydrogencarbonate; and alkali metal hydroxides such as sodium hydroxide.

The reaction (G) can be carried out at the temperature of from about 10° C. to about 200° C., preferably from about 80° C. to about 120° C.

Compounds of the formula (IV) of this invention, wherein $Z_1$ is a hydroxyl group in the 4-, 6- or 7-position and $Z_2$ is a hydrogen atom can be prepared by reacting a 1-(aminoalkyl)-3-(aminoalkylamino)-chloroindazole whose chlorine atom is in the 4-, 6- or 7-position with magnesium powder, isopropyl bromide, oxygen gas and carbon dioxide gas in the presence of a reaction medium. Exemplary reaction media which can be employed include ethers such as diethyl ether, tetrahydrofuran and dioxane. This reaction can be carried out at a temperature of from about 0° C. to about 100° C., preferably from about 0° C. to about 10° C.

Compounds of the formula (IV) of this invention, wherein $Z_1$ is a hydroxyl group in the 5-position and $Z_2$ is a hydrogen atom can be prepared by sulfonating a 1-(aminoalkyl)-3-(aminoalkylamino)indazole with sulfuric acid, and then reacting the sulfonated compound with an alkali compound in the presence of a reaction medium. The sulfonation reaction can be carried out at a temperature of from about 0° C. to about 100° C., preferably from about 50° C. to about 100° C. The reaction between the sulfonated compound and the alkali compound can be carried out at a temperature of from about 0° C. to about 300° C., preferably from about 250° C. to about 300° C. Exemplary alkali compounds which can be employed include metal hydroxides such as sodium hydroxide, potassium hydroxide and calcium hydroxide. The reaction medium which can be employed is water.

Compounds of the formula (IV) of this invention, wherein $Z_1$ is an amino group in the 5-position and $Z_2$ is a hydrogen atom can be prepared by reacting a 1-(aminoalkyl)-3-(aminoalkylamino)indazole with both nitric acid and sulfuric acid in the absence of a reaction medium to obtain a 1-(aminoalkyl)-3-(aminoalkylamino)-5-nitroindazole, and then reducing the 1-(aminoalkyl)-3-(aminoalkylamino)-5-nitroindazole with both iron powder and hydrochloric acid in the presence of a reaction medium to give a 1-(aminoalkyl)-3-(aminoalkylamino)-5-aminoindazole. The reaction along the 1-(aminoalkyl)-3-(aminoalkylamino)-indazole, nitric acid and sulfuric acid can be carried out at a temperature of from about −20° C. to about 20° C., preferably from about 0° C. to about 10° C. The reduction reaction of the 1-(aminoalkyl)-3-(aminoalkylamino)-5-nitroindazole can be carried out at a temperature of from about 0° C. to about 200° C., preferably from about 0° C. to about 80° C. Exemplary reaction media which can be employed in the reduction reaction include water and alcohols such as methyl alcohol, ethyl alcohol, n-propyl alcohol, isopropyl alcohol and n-butyl alcohol.

Compounds of the formula (IV) of this invention, wherein both $Z_1$ and $Z_2$ are amino groups in the 5- and 7-positions can be prepared by reacting a 1-(aminoalkyl)-3-(aminoalkylamino)indazole with both nitric acid and sulfuric acid in the absence of a reaction medium to obtain a 1-(aminoalkyl)-3-(aminoalkylamino)-5,7-dinitroindazole, and then reducing the 1-(aminoalkyl)-3-(aminoalkylamino)-5,7-dinitroindazole with a reducing agent to give a 1-(aminoalkyl)-3-(aminoalkylamino)-5,7-diaminoindazole. The reaction among the 1-(aminoalkyl)-3-(aminoalkylamino)indazole, nitric acid and sulfuric acid can be carried out at a temperature of from about 0° C. to about 100° C., preferably from about 0° C. to about 10° C. The reduction reaction of the 1-(aminoalkyl)-3-(aminoalkylamino)-5,7-dinitroindazole can be carried out at a temperature of from about 0° C. to about 200° C., preferably from about 50° C. to about 80° C. Exemplary reducing agents which can be employed in the reduction reaction include iron-hydrochloric acid, zinc-hydrochloric acid, lithium aluminum hydride and hydrogen gas.

Compounds of the formula (IV) of this invention can be also prepared by reacting a 1-aminoalkyl-3-halogenoindazole whose benzene ring has substituents of the formula (XVIII) with an aminoalkylamine compound of the formula (XIX) in the presence of an acid acceptor in accordance with the following equation:

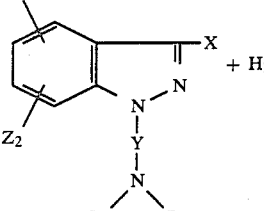

wherein Y, $R_1$, $R_2$, Y', $R'_1$ and $R'_2$ are the same as defined in the formula (IV); $Z_1$ and $Z_2$ are the same as defined in the formula (IX); and X is a chlorine atom, a bromine atom or an iodine atom.

The 1-aminoalkyl-3-halogenoindazole (XVIII) can be prepared by reacting a 3-halogenoindazole of the formula (XIV) with an ω-halogenoalkylamine of the formula (X) in accordance with the following equation:

wherein Y, $R_1$ and $R_2$ are the same as defined in the formula (II); $Z_1$ and $Z_2$ are the same as defined in the formula (IV); and X is a chlorine atom, a bromine atom or an iodine atom.

The ω-halogenoalkylamines (X) which can be employed in this reaction include the same ω-halogenoalkylamines used in the reaction (A) of this invention.

The aminoalkylamine compounds (XIX) which can be employed in the reaction (H) include the same aminoalkylamine compounds used in the reaction (E) of this invention.

The reaction (H) can be carried out in the presence of a reaction medium. Exemplary reaction media which can be employed include non-proton polar solvents such as acetonitrile, dimethyl sulfoxide and N,N-dimethylformamide; and halogenated hydrocarbons such as chloroform, methylene chloride, carbon tetrachloride and 1,2-dichloroethane.

Exemplary acid acceptors which can be employed in the reaction (H) include tertiary amines such as pyridine and triethylamine; alkali metal carbonates such as potassium carbonate; alkali metal bicarbonates such as sodium hydrogencarbonate; and alkali metal hydroxides such as sodium hydroxide.

The reaction (H) can be carried out at a temperature of from about 0° C. to about 200° C., preferably from about 35° C. to about 120° C.

Further, compounds of the formula (IV) of this invention can be prepared by reacting a 3-(aminoalkylamino)indazole whose benzene ring has substituents of the formula (XX) with a halogenoalkylamine compound of the formula (X) in the presence of an acid acceptor for hydrogen halides generated in the reaction in accordance with the following equation:

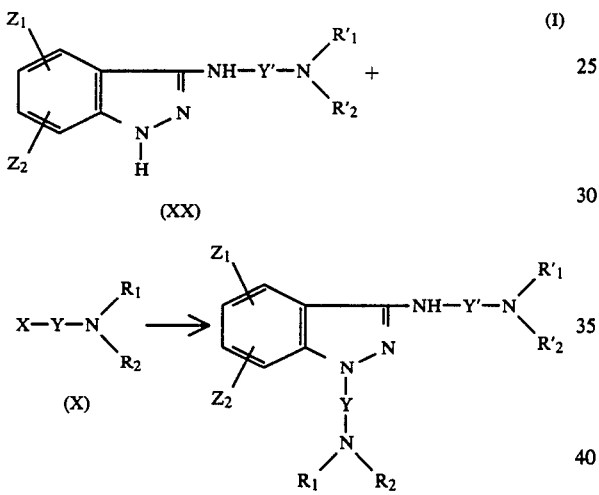

wherein Y, $R_1$, $R_2$, Y', $R'_1$ and $R'_2$ are the same as defined in the formula (IV); $Z_1$ and $Z_2$ are the same as defined in the formula (IX); and X is a chlorine atom, a bromine atom or an iodine atom.

The halogenoalkylamine compound (X) which can be employed in the reaction (I) include the same ω-halogenoalkylamines as used in the reaction (A) of this invention.

The reaction (I) can be carried out in the presence of a reaction medium. Exemplary reaction media which can be employed include non-proton polar solvents such as acetonitrile, dimethyl sulfoxide and N,N-dimethylformamide; and alcohols such as methyl alcohol, ethyl alcohol, propyl alcohol and butyl alcohol.

Exemplary acid acceptors which can be employed in the reaction (I) include tertiary amines such as pyridine and triethylamine; alkali metal carbonates such as potassium carbonate; alkali metal bicarbonates such as sodium hydrogencarbonate; and alkali metal hydroxide such as sodium hydroxide.

The reaction (I) can be carried out at a temperature of from about 0° C. to about 200° C., preferably from about 80° C. to about 120° C.

Furthermore, Compounds of the formula (IV) of this invention can be prepared by reacting an 2-amino-1-(aminoalkyl)benzamide whose benzene ring has substituents of the formula (XVI) with a halogenoalkylamine compound of the formula (X) in the presence of an acid acceptor in accordance with the following equations:

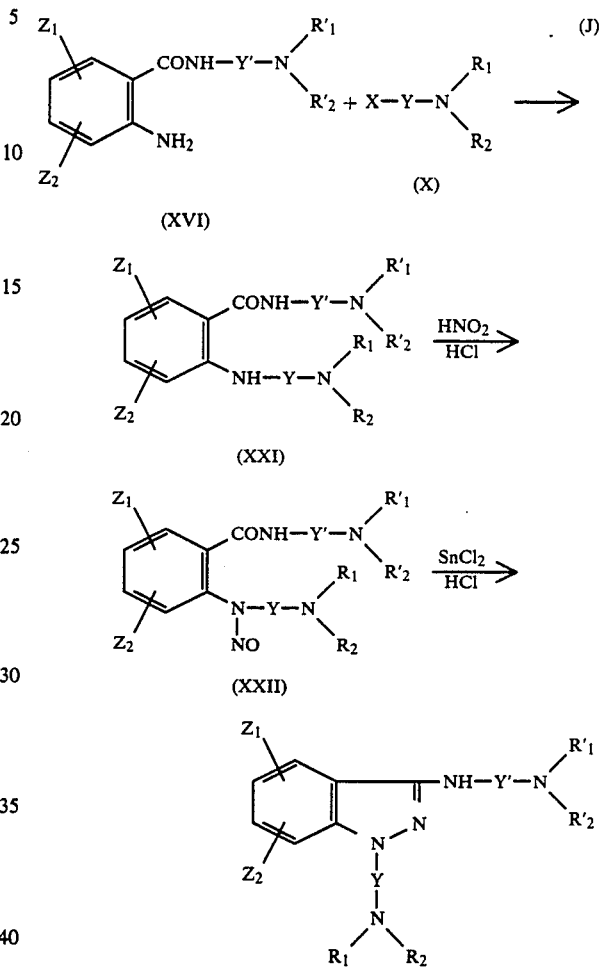

wherein Y, $R_1$, $R_2$, Y', $R'_1$ and $R'_2$ are the same as defined in the formula (IV); $Z_1$ and $Z_2$ are the same as defined in the formula (IX); and X is a chlorine atom, a bromine atom or an iodine atom.

The reaction between the compound of the formula (XVI) and the compound of the formula (X) can be carried out in the presence of an acid acceptor and a reaction medium. Exemplary reaction media which can be employed include non-proton polar solvents such as acetonitrile, dimethyl sulfoxide and N,N-dimethylformamide; and alcohols such as methyl alcohol, ethyl alcohol, propyl alcohol and butyl alcohol. Exemplary acid acceptors which can be employed include tertiary amines such as pyridine and triethylamine; alkali metal carbonates such as potassium carbonate; alkali metal bicarbonates such as sodium hydrogencarbonate; and alkali metal hydroxide such as sodium hydroxide.

The reaction between the compound of the formula (XVI) and the compound of the formula (X) can be carried out at a temperature of from about 0° C. to about 200° C., preferably from about 80° C. to about 120° C.

The compound (XXI) is reacted with sodium nitrite and hydrochloric acid to obtain a nitroso compound (XXII), and the compound (XXII) thus obtained is reduced with stannous chloride and hydrochloric acid to obtain the compound of the formula (IV). These reactions can be carried out at a temperature of from about −20° C. to about 20° C., preferably from about 0° C. to about 10° C.

Compounds of the formula (V) of this invention can be prepared by reacting 3-aminoindazole with phthalic anhydride to obtain a 3-phthalimidoindazole, reacting the 3-phthalimidoindazole with a 1-(halogenoalkyl)-morpholine to give a 1-(morpholinoalkyl)-3-phthalimidoindazole, and then treating the 1-(morpholinoalkyl)-3-phthalimidoindazole with hydrazine hydrate to release the protective group of the 3-position amino group. The reaction conditions which can be employed are the same as those of the reaction (A).

The 1-(halogenoalkyl)morpholines which can be employed in this reaction include 1-(2-chloroethyl)morpholine, 1-(2-bromoethyl)morpholine, 1-(2-iodoethyl)morpholine, 1-(3-chloropropyl)morpholine, 1-(3-bromopropyl)morpholine, 1-(3-iodopropyl)morpholine, 1-(1-methyl-3-chloropropyl)morpholine, 1-(1-methyl-3-bromopropyl)morpholine and 1-(1-methyl-3-iodopropyl)morpholine.

Compounds of the formula (VI) of this invention can be prepared by reacting a 3-aminoindazole with a 1-(halogenoalkyl)morpholine in the presence of a reaction medium and an acid acceptor. The reaction conditions which can be employed are the same as those of the reaction (C) of this invention. Exemplary 1-(halogenoalkyl)morpholines which can be employed include the same 1-(halogenoalkyl)morpholines as used in the reaction which is preparing the compounds (V) of this invention.

Compounds of the formula (VI) of this invention can also be prepared by reacting a 3-aminoindazole with morpholinoacrylamide. The reaction conditions which can be employed are the same as those of the reaction (D) of this invention.

Compound of the formula (VII) of this invention can be prepared by reacting a 1-(morpholinoalkyl)-3-aminoindazole of the formula (V) with an ω-halogenoalkylamine. The ω-halogenoalkylamines which can be employed include the same ω-halogenoalkylamines as used in the reaction (A) of this invention. The reaction conditions which can be employed are the same as those of the reaction (G) of this invention.

Compounds of the formula (VIII) of this invention, wherein $Z_1$ is a hydroxyl group in the 4-, 6- or 7-position and $Z_2$ is a hydrogen atom can be prepared by reacting a 3-aminoindazole having a hydroxyl group in the 4-, 6- or 7-position with magnesium powder, isopropyl bromide, oxygen gas and carbon dioxide gas in the presence of a reaction medium. Exemplary reaction media which can be employed include ethers such as diethyl ether, tetrahydrofuran and dioxane. This reaction can be carried out at a temperature of from about 0° C. to about 100° C., preferably from about 0° C. to about 10° C.

Compounds of the formula (VIII) of this invention, wherein $Z_1$ is a hydroxyl group in the 5-position and $Z_2$ is a hydrogen atom can be prepared by sulfonating 3-aminoindazole with sulfuric acid, and then reacting the sulfonated 3-aminoindazole with an alkali compound in the presence of a reaction medium. The sulfonation reaction can be carried out at a temperature of from about 0° C. to about 100° C., preferably from about 50° C. to about 100° C. The reaction between the sulfonated 3-aminoindazole and the alkali compound can be carried out at a temperature of from about 0° C. to about 300° C., preferably from about 250° C. to about 300° C. Exemplary alkali compounds which can be employed include metal hydroxides such as sodium hydroxide, potassium hydroxide and calcium hydroxide. The reaction medium which can be employed is water.

Compounds of the formula (VIII) of this invention, wherein $Z_1$ is an iodine atom in the 5- or 7-position and $Z_2$ is a hydrogen atom can be prepared by reacting 5-iodoanthranilonitrile or 3-iodoanthranilonitrile with sodium nitrite, and then treating the reaction product with a reducing agent. These reactions can be carried out at a temperature of from about 0° C. to about 100° C., preferably from about 0° C. to about 10° C. Exemplary reducing agents which can be employed in the reduction reaction include stannous chloride-hydrochloric acid, ferrous chloride-hydrochloric acid, zinc chloridehydrochloric acid and sodium sulfite.

Compounds of the formula (VIII) of this invention, wherein both $Z_1$ and $Z_2$ are amino groups in the 5- and 7-positions can be prepared by reacting 3-aminoindazole with both nitric acid and sulfuric acid, and then treating the reaction product with a reducing agent. The reaction among 3-aminoindazole, nitric acid and sulfuric acid can be carried out at a temperature of from about 0° C. to about 100° C., preferably from about 0° C. to about 10° C. The reduction reaction can be carried out at a temperature of from about 0° C. to about 200° C., preferably from about 50° C. to about 80° C. Exemplary reducing agents which can be employed in the reduction reaction include iron-hydrochloric acid, zinc-hydrochloric, lithium aluminum hydride and hydrogen gas.

The pharmaceutically acceptable non-toxic acid addition salts of the indazole derivatives of the general formula (I) according to this invention can be prepared by reacting the indazole derivatives with inorganic or organic acids. The amount of the acids which can be employed in this reaction is substantially equimolar of the indazole derivatives. The reaction can be carried out in an aqueous solvent or an organic solvent such as methyl alcohol and ethyl alcohol. After the reaction is completed, the solvent is evaporated carefully to give the salts in a solid state.

Suitable examples of such physiologically acceptable acid addition salts include the salts of inorganic acids such as hydrochloric acid, hydrobromic acid, hydroiodic acid, sulfuric acid, phosphoric acid and nitric acid; the salts of organic acids such as formic acid, acetic acid, propionic acid, succinic acid, lactic acid, maleic acid, fumaric acid, malonic acid, oxalic acid, citric acid, tartric acid, malic acid, mucic acid, gluconic acid, benzoic acid, salicyclic acid, 1,5-naphthalenedisulfonic acid, ascoroic acid, phenylacetic acid, p-aminosalicylic acid, methanesulfonic acid, ethanesulfonic acid, hydroxyethanesulfonic acid, benzenesulfonic acid and p-toluenesulfonic acid; and saccharates.

It has now been found that all the indazole derivatives of the general formula (I) and their physiologically acceptable salts have therapeutic use such as anti-inflammatory drugs and analgesic drugs. More specifically, the indazole derivatives and the physiologically acceptable salts of this invention have unique effects as compared with known 3-aminoindazole derivatives, for example, reduction of swelling caused by an inflammatory, abatement of pain and suppression of digestive tract ulcers, a side effect caused by using acidic non-steroidal anti-inflammatory drugs. Thus, the novel indazole derivatives of this invention have many advantages as anti-inflammatory drugs.

The following tests illustrate the therapeutic activities of the indazoles of this invention.

Anti-inflammatory Activity

An anti-inflammatory activity was measured by orally administering 100 mg/kg of a hydrochloride of the indazole derivative of this invention as set forth in Table 1 to an animal in accordance with the standard method of Carrageenin Edema Test in Rat's Paw described in C. A. Winter et al., Proc. Soc. Exp. Biol. Med., 111, 544 (1962). The activity is evaluated with respect to whether the effect of inhibition shows a statistically significant difference (20%) in a rat. The results of the Carrageenin edema test are shown in Table 1.

TABLE 1

| Compound No. | Indazole Derivative | Inhibition (%) |
|---|---|---|
| (1) | 1-(3-Diethylaminopropyl)-3-amino-4-chloroindaole | 58 |
| (2) | 1-(3-Diethylaminopropyl)-3-amino-5-chloroindazole | 55 |
| (3) | 1-(3-Diethylaminopropyl)-3-amino-6-chloroindazole | 54 |
| (4) | 1-(3-Diethylaminopropyl)-3-amino-7-chloroindazole | 59 |
| (5) | 1-(3-Diethylaminopropyl)-3,5-diaminoindazole | 59 |
| (6) | 1-(3-Diethylaminopropyl)-3-amino-5-methoxyindazole | 56 |
| (7) | 1-(3-Diethylaminopropyl)-3-amino-5-methoxyindazole | 58 |
| (8) | 1-(3-Di-n-butylaminopropyl)-3-amino-5-chloroindazole | 56 |
| (9) | 1-(3-Dimethylaminobutyl)-3-amino-5-chloroindazole | 37 |
| (10) | 1-(3-Diethylamino-5-methylhexyl)-3-amino-5-chloroindazole | 49 |
| (11) | 1-(3-Piperidinopropyl)-3-amino-5-chloroindazole | 54 |
| (12) | 1-(6-Piperidinohexyl)-3-amino-5-chloroindazole | 28 |
| (13) | 1-(3-Piperidinobutyl)-3-amino-5-chloroindazole | 49 |
| (14) | 1-(3-Piperidino-5-methylhexyl)-3-amino-5-chloroindazole | 34 |
| (15) | 1-[3-(2-Methylpiperidino)propyl]-3-amino-5-chloroindazole | 50 |
| (16) | 1-[3-(2,6-Dimethylpiperidino)propyl]-3-amino-5-chloroindazole | 33 |
| (17) | 1-[3-(4-Hydroxypiperidino)propyl]-3-amino-5-chloroindazole | 37 |
| (18) | 1-[3-(4-Chloropiperidino)propyl]-3-amino-5-chloroindazole | 66 |
| (19) | 1-(3-Homopiperidinopropyl)-3-amino-5-chloroindazole | 38 |
| (20) | 1-[3-(4-Methylpiperazino)propyl]-3-amino-5-chloroindazole | 26 |
| (21) | 1-(3-Pyrrolidinopropyl)-3-amino-5-chloroindazole | 39 |
| (22) | 1-(3-Morpholinopropyl)-3-amino-5-chloroindazole | 46 |
| (23) | 1-(3-Diethylaminopropyl)-3-amino-4-hydroxyindazole | 56 |
| (24) | 1-(3-Diethylaminopropyl)-3-amino-5-hydroxyindazole | 53 |
| (25) | 1-(3-Diethylaminopropyl)-3-amino-6-hydroxyindazole | 52 |
| (26) | 1-(3-Diethylaminopropyl)-3-amino-7-hydroxyindazole | 57 |
| (27) | 1-(3-Diethylaminopropyl)-3-amino-5-iodoindazole | 57 |
| (28) | 1-(3-Diethylaminopropyl)-3-amino-7-iodoindazole | 54 |
| (29) | 1-(3-Diethylaminopropyl)-3,5,7-triaminoindazole | 56 |
| (30) | 1-(3-Di-n-butylaminopropyl)-3-amino-5-hydroxyindazole | 54 |
| (31) | 1-(3-Dimethylaminobutyl)-3-amino-5-hydroxyindazole | 35 |
| (32) | 1-(3-Diethylamino-5-methylhexyl)-3-amino-5-hydroxyindazole | 47 |
| (33) | 1-(3-Piperidinopropyl)-3-amino-5-hydroxyindazole | 52 |
| (34) | 1-(6-Piperidinohexyl)-3-amino-5-hydroxyindazole | 26 |
| (35) | 1-(3-Piperidinobutyl)-3-amino-5-hydroxyindazole | 47 |
| (36) | 1-(3-Piperidino-5-methylhexyl)-3-amino-5-hydroxyindazole | 32 |
| (37) | 1-[3-(2-Methylpiperidino)propyl]-3-amino-5-hydroxyindazole | 48 |
| (38) | 1-[3-(2,6-Dimethylpiperidino)propyl]-3-amino-5-hydroxyindazole | 31 |
| (39) | 1-[3-(4-Hydroxypiperidino)propyl]-3-amino-5-hydroxyindazole | 35 |
| (40) | 1-[3-(4-Chloropiperidino)propyl]-3-amino-5-hydroxyindazole | 64 |
| (41) | 1-(3-Homopiperidinopropyl)-3-amino-5-hydroxyindazole | 36 |
| (42) | 1-[3-(4-Methylpiperazino)propyl]-3-amino-5-hydroxyindazole | 24 |
| (43) | 1-(3-Pyrrolidinopropyl)-3-amino-5-hydroxyindazole | 36 |
| (44) | 1-(3-Morpholinopropyl)-3-amino-5-hydroxyindazole | 46 |
| (45) | 3-(3-Diethylaminopropylamino)-4-chloroindazole | 61 |
| (46) | 3-(3-Diethylaminopropylamino)-5-chloroindazole | 59 |
| (47) | 3-(3-Diethylaminopropylamino)-6-chloroindazole | 58 |
| (48) | 3-(3-Diethylaminopropylamino)-7-chloroindazole | 57 |
| (49) | 3-(3-Diethylaminopropylamino)-5-aminoindazole | 55 |
| (50) | 3-(3-Diethylaminopropylamino)-5-methoxyindazole | 52 |
| (51) | 3-(3-Diethylaminopropylamino)-5-methylindazle | 60 |
| (52) | 3-(3-Di-n-butylaminopropylamino)-5-chloroindazole | 61 |
| (53) | 3-(3-Dimethylaminobutylamino)-5-chloroindazole | 48 |
| (54) | 3-(3-Diethylamino-5-methylhexylamino)-5-chloroindazole | 46 |
| (55) | 3-(3-Piperidinopropylamino)-5-chloroindazole | 47 |
| (56) | 3-(6-Piperidinohexylamino)-5-chloroindazole | 29 |
| (57) | 3-(3-Piperidinobutylamino)-5-chloroindazole | 54 |
| (58) | 3-(3-Piperidino-5-methylhexylamino)-5-chloroindazole | 40 |
| (59) | 3-[3-(2-Methylpiperidino)propylamino]-5-chloroindazole | 63 |
| (60) | 3-[3-(2,6-Dimethylpiperidino)propylamino]-5-chloroindazole | 36 |
| (61) | 3-[3-(4-Hydroxypiperidino)propylamino]-5-chloroindazole | 46 |
| (62) | 3-[3-(4-Chloropiperidino)propylamino]-5-chloroindazole | 65 |
| (63) | 3-(3-Homopiperidinopropylamino)-5-chloroindazole | 57 |
| (64) | 3-[3-(4-Methylpiperadino)propylamino]-5-chloroindazole | 29 |
| (65) | 3-(3-Pyrrolidinopropylamino)-5-chloroindazole | 36 |
| (66) | 3-(3-Morpholinopropylamino)-5-hydroxyindazole | 46 |
| (67) | 3-(3-Diethylaminopropylamino)-4-hydroxyindazole | 55 |
| (68) | 3-(3-Diethylaminopropylamino)-5-hydroxyindazole | 52 |

TABLE 1-continued

| Compound No. | Indazole Derivative | Inhibition (%) |
|---|---|---|
| (69) | 3-(3-Diethylaminopropylamino)-6-hydroxyindazole | 51 |
| (70) | 3-(3-Diethylaminopropylamino)-7-hydroxyindazole | 56 |
| (71) | 3-(3-Diethylaminopropylamino)-5-iodoindazole | 56 |
| (72) | 3-(3-Diethylaminopropylamino)-7-iodoindazole | 53 |
| (73) | 3-(3-Diethylaminopropylamino)-5,7-diaminoindazole | 55 |
| (74) | 3-(3-Di-n-butylaminopropylamino)-5-hydroxyindazole | 53 |
| (75) | 3-(3-Dimethylaminobutylamino)-5-hydroxyindazole | 34 |
| (76) | 3-(3-Diethylamino-5-methylhexylamino)-5-hydroxyindazole | 46 |
| (77) | 3-(3-Piperidinopropylamino)-5-hydroxyindazole | 51 |
| (78) | 3-(6-Piperidinohexylamino)-5-hydroxyindazole | 25 |
| (79) | 3-(3-Piperidinobutylamino)-5-hydroxyindazole | 46 |
| (80) | 3-(3-Piperidino-5-methylhexylamino)-5-hydroxyindazole | 32 |
| (81) | 3-[3-(2-Methylpiperidino)propylamino]-5-hydroxyindazole | 47 |
| (82) | 3-[3-(2,6-Dimethylpiperidino)propylamino]-5-hydroxyindazole | 30 |
| (83) | 3-[3-(4-Hydroxypiperidino)propylamino]-5-hydroxyindazole | 34 |
| (84) | 3-[3-(4-Chloropiperidino)propylamino]-5-hydroxyindazole | 63 |
| (85) | 3-(3-Homopiperidinopropylamino)-5-hydroxyindazole | 35 |
| (86) | 3-[3-(4-Methylpiperadino)propylamino]9 -5-hydroxyindazole | 23 |
| (87) | 3-(3-Pyrrolidinopropylamino)-5-hydroxyindazole | 38 |
| (88) | 3-(3-Morpholinopropylamino)-5-hydroxyindazole | 46 |
| (89) | 1-(3-Diethylaminopropyl)-3-(3-diethylaminopropylamino)-4-chloroindazole | 30 |
| (90) | 1-(3-Diethylaminopropyl)-3-(3-diethylaminopropylamino)-5-chloroindazole | 29 |
| (91) | 1-(3-Diethylaminopropyl)-3-(6-diethylaminopyropylamino)-6-chloroindazole | 22 |
| (92) | 1-(3-Diethylaminopropyl)-3-(3-diethylaminopropylamino)-7-chloroindazole | 32 |
| (93) | 1-(3-Diethylaminopropyl)-3-(3-diethylaminopropylamino)-5-aminoindazole | 28 |
| (94) | 1-(3-Diethylaminopropyl)-3-(3-diethylaminopropylamino)-5-methoxyindazole | 30 |
| (95) | 1-(3-Diethylaminopropyl)-3-(3-diethylaminoamino)-5-methylindazole | 29 |
| (96) | 1-(3-Diethylaminopropyl)-3-(3-piperidinopropylamino)-5-chloroindazole | 29 |
| (97) | 1-(3-Diethylaminopropyl)-3-(6-piperidinoamino)-5-chloroindazole | 22 |
| (98) | 1-(3-Diethylaminopropyl)-3-(3-di-n-butylaminopropylamino)-5-chloroindazole | 32 |
| (99) | 1-(3-Diethylaminopropyl)-3-(3-piperidinobutylamino)-5-chloroindazole | 28 |
| (100) | 1-(3-Piperidinopropyl)-3-(3-diethylamino propylamino)-5-chloroindazole | 30 |
| (101) | 1-(3-Piperidinopropyl)-3-(3-piperidinopropylamino)-5-chlorindazole | 29 |
| (102) | 1-(3-Piperidinopropyl)-3-(6-piperidinohexylamino)-5-chloroindazole | 22 |
| (103) | 1-(3-Piperidinopropyl)-3-(3-piperidinobutylamino)-5-chloroindazole | 29 |
| (104) | 1-(3-Piperidinobutyl)-3-(3-diethylaminopropyl-chloroindazole | 30 |
| (105) | 1-(3-Piperidinobutyl)-3-(3-piperidinopropylamino)-5-chloroindazole | 29 |
| (106) | 1-(3-Piperidinobutyl)-3-(3-piperidino-5-methylhexylamino)-5-chloroindazole | 22 |
| (107) | 1-(3-Piperidinobutyl)-3-(3-dimethylaminobutylamino)-5-chloroindazole | 22 |
| (108) | 1-(3-Dimethylaminobutyl)-3-(3-diethylamino-5-chloroindazole | 30 |
| (109) | 1-(3-Dimethylaminobutyl)-3-(3-piperidinopropylamino)-5-chloroindazole | 29 |
| (110) | 1-(3-Dimethylaminobutyl)-3-(3-piperidinobutylamino)-5-chloroindazole | 28 |
| (111) | 1-(3-Dimethylaminobutyl)-3-(3-diethylamino-5-methylhexylamino)-5-chloroindazole | 22 |
| (112) | 1-(3-Pyrrolidinopropyl)-3-(3-homopiperidinopropylamino)-5-chloroindazole | 29 |
| (113) | 1-(3-Pyrrolidinopropyl)-3-[3-(2-methylpiperidino)propylamino]-5-chloroindazole | 31 |
| (114) | 1-(3-Pyrrolidinopropyl)-3-[3-(4-methylpiperazino)propylamino]-5-chloroindazole | 30 |
| (115) | 1-(3-Morpholinopropyl)-3-(3-diethylaminopropylamino)-5-chloroindazole | 31 |
| (116) | 1-(3-Morpholinopropyl)-3-[3-(2,6-dimethylpiperidin0)propyl-amino]-5-chloroindazole | 33 |
| (117) | 1-(3-Morpholinopropyl)-3-[3-(4-chloropiperidino)propylamino]-5-chloroindazole | 30 |
| (118) | 1-(3-Morpholinopropyl)-3-[3-(4-hydroxypiperidino)propylamino]-5-chloroindazole | 31 |
| (119) | 1-(3-Diethylaminopropyl)-3-(3-diethylaminopropylamino)-4-hydroxyindazole | 29 |
| (120) | 1-(3-Diethylaminopropyl)-3-(3-diethylaminopropylamino)-5-hydroxyindazole | 28 |
| (121) | 1-(3-Diethylaminopropyl)-3-(3-diethylamino propylamino)-6-hydroxyindazole | 21 |
| (122) | 1-(3-Diethylaminopropyl)-3-(3-diethylaminopropylamino)-7-hydroxyindazole | 31 |
| (123) | 1-(3-Diethylaminopropyl)-3-(3-diethylaminopropylamino)-5-iodoindazole | 27 |
| (124) | 1-(3-Diethylaminopropyl)-3-(3-diethylaminopropylamino)-7-iodoindazole | 29 |
| (125) | 1-(3-Diethylaminopropyl)-3-(3-diethylaminopropylamino)-5,7-diaminoindazole | 28 |
| (126) | 1-(3-Diethylaminopropyl)-3-(3-piperidinopropylamino)-5-hydroxyindazole | 28 |
| (127) | 1-(3-Diethylaminopropyl)-3-(6-piperidinohexylamino)-5-hydroxyindazole | 21 |
| (128) | 1-(3-Diethylaminopropyl)-3-(3-di-n-butylaminopropylamino)-5-hydroxyindazole | 31 |
| (129) | 1-(3-Diethylaminopropyl)-3-(3-piperidinobutylamino)-5-hydroxyindazole | 27 |
| (130) | 1-(3-Piperidinopropyl)-3-(3-diethylaminoamino)-5-hydroxyindazole | 29 |
| (131) | 1-(3-Piperidinopropyl)-3-(3-piperidinopropylamino)-5-hydroxyindazole | 28 |
| (132) | 1-(3-Piperidinopropyl)-3-(6-piperidinohexylamino)-5-hydroxyindazole | 21 |
| (133) | 1-(3-Piperidinopropyl)-3-(3-piperidinobutylamino)-5-hydroxyindazole | 28 |
| (134) | 1-(3-Piperidinobutyl)-3-(3-diethylaminopropylamino)-5-hydroxyindazole | 29 |
| (135) | 1-(3-Piperidinobutyl)-3-(3-piperidinopropylamino)-5-hydroxyindazole | 28 |
| (136) | 1-(3-Piperidinobutyl)-3-(3-piperidino-5-methylhexylamino)-5-hydroxyindazole | 21 |
| (137) | 1-(3-Piperidinobutyl)-3-(3-dimethylaminobutylamino)-5-hydroxyindazole | 21 |
| (138) | 1-(3-Dimethylaminobutyl)-3-(3-diethylaminopropylamino)-5-hydroxyindazole | 29 |
| (139) | 1-(3-Dimethylaminobutyl)-3-(3-piperidinopropylamino)-5-hydroxyindazole | 28 |
| (140) | 1-(3-Dimethylaminobutyl)-3-(3-piperidinobutylamino)-5-hydroxyindazole | 27 |
| (141) | 1-(3-Dimethylaminobutyl)-3-(3-diethylamino-5-methylhexylamino)-5-hydroxyindazole | 21 |
| (142) | 1-(3-Pyrrolidinopropyl)-3-(3-homopiperidinopropylamino)-5-hydroxyindazole | 28 |
| (143) | 1-(3-Pyrrolidinopropyl)-3-[3-(2-methylpiperidino)propylamino]-5-hydroxyindazole | 30 |
| (144) | 1-(3-Pyrrolidinopropyl)-3-[3-(4-methylpiperazino)propylamino]-5-hydroxyindazole | 26 |
| (145) | 1-(3-Morpholinopropyl)-3-(3-diethylaminoamino)-5-hydroxyindazole | 30 |
| (146) | 1-(3-Morpholinopropyl)-3-[3-(2,6-dimethylpiperidino)propylamino]-5-hydroxyindazole | 32 |
| (147) | 1-(3-Morpholinopropyl)-3-[3-(4-chloropiperidino) | 29 |

TABLE 1-continued

| Compound No. | Indazole Derivative | Inhibition (%) |
|---|---|---|
| | propylamino]-5-hydroxyindazole | |
| (148) | 1-(3-Morpholinopropyl)-3-[3-(4-hydroxypiperidino)propylamino]-5-hydroxyindazole | 30 |
| (149) | 1-(3-Morpholinopropyl)-3-aminoindazole | 50 |
| (150) | 1-(3-Morpholinobutyl)-3-aminoindazole | 39 |
| (151) | 1-(2-Morpholinoethyl)-3-aminoindazole | 48 |
| (152) | 3-(3-Morpholinopropylamino)indazole | 51 |
| (153) | 3-(3-Morpholinobutylamino)indazole | 51 |
| (154) | 3-(2-Morpholinoethylamino)indazole | 50 |
| (155) | 1-(3-Morpholinopropyl)-3-(3-diethylaminopropylamino)indazole | 30 |
| (156) | 1-(3-Morpholinopropyl)-3-[3-(2,6-dimethylpiperidino)propylamino]indazole | 32 |
| (157) | 1-(3-Morpholinopropyl)-3-[3-(4-chloropiperidino)propylamino]indazole | 29 |
| (158) | 1-(3-Morpholinopropyl)-3-[3-(4-hydroxypiperidino)propylamino]indazole | 30 |
| (159) | 1-(3-Di-n-butylaminopropyl)-3-(3-morpholinopropylamino)indazole | 41 |
| (160) | 1-(3-Piperidinopropyl)-3-(3-morpholinopropylamino)indazole | 39 |
| (161) | 3-Amino-4- | 41 |
| (162) | 3-Amino-5- | 45 |
| (163) | 3-Amino-6- | 43 |
| (164) | 3-Amino-7- | 42 |
| (165) | 3-Amino-5- | 55 |
| (166) | 3-Amino-7- | 50 |
| (167) | 3,5,7-Triaminoindazole | 85 |
| C-1 | 1-Propyl-3-aminoindazole | 7 |
| C-2 | 1-(2-Phenylethyl)-3-aminoindazole | 7 |
| C-3 | 3,7-Diaminoindazole | 6 |

In Table 1, 1-propyl-3-aminoindazole [referred to as Compound No. "C-1"], 1-(2-phenylethyl)-3-aminoindazole [referred to as Compound No. "C-2"] and 3,7-diaminoindazole [referred to as Compound No. "C-3"] are all comparative compounds.

As clearly shown in Table 1, the indazole derivatives having no amino group at the ω-position such as Compounds C-1 and C-2 have little anti-inflammatory activity in comparison with Compounds (1) to (160) of this invention. Further, the indazole derivatives having only one amino group in the benzene ring such as Compound C-3 have little anti-inflammatory activity in comparison with Compound (167) of this invention.

As described in Yoshihiko Oyagi, "Superoxide and Medical Science", pp. 120–144, published by Kyoritsu Shuppan, a superoxide is considered to be one of the factors which cause the inflammation. The inventors have confirmed that 3-amino-5-hydroxyindazole of this invention [Compound (162)] can catch the superoxide. More specifically, it has been confirmed by the Electron Spin Resonance spectra (ESR spectra) and UV spectra that the 3-amino-5-hydroxyindazole accepts one electron from the superoxide when 3-amino-5-hydroxyindazole exists with potassium superoxide and dicyclohexyl-18-crown-6 (Ardrich, U.S.A.) in acetonitrile.

In the measurement of the ESR spectrum, a mixture of potassium superoxide and dicyclohexyl-18-crown-6 shows a single signal which is due to the superoxide in acetonitrile. However, when the 3-amino-5-hydroxyindazole was added to the mixture, six superfine signals are observed. These six signals are due to a phenoxy radical produced when the 3-amino-5-hydroxyindazole accepts one electron from the superoxide.

According to the description on Transactions of the Faraday Society, 59, 2016–2026 (1963), the UV spectrum of a phenoxy radical is observed at 380–430 nm. When the UV spectrum of a mixture of the 3-amino-5-hydroxyindazole and dicyclohexyl-18-crown-6 is measured in acetonitrile, λmax is observed at 306 nm. If potassium superoxide is added to the mixture, λmax is observed at 403 nm and 426 nm. On the other hand, no absorptions are observed at 350–450 nm when the UV spectra of potassium superoxide and 3-amino-5-hydroxyindazole are measured respectively in the presence of both dicyclohexyl-18-crown-6 and acetonitrile. These results show that a phenoxy radical is produced when 3-amino-5-hydroxyindazole exists with potassium superoxide.

Edema Inhibition Effect

An edema inhibition effect was measured by orally administering 100 mg/kg of a hydrochloride of the indazole derivative of this invention as set forth in Table 2 to an animal (rat) in accordance with the anti-edema test as described in C. A. Winter et al., NonSteroidal Anti-inflammatory Drugs. As an edema inducing substance, bradykinin, histamine and serotonin were employed. The effect is evaluated with respect to whether the effect of inhibition shows a statistically significant difference (20%) in a rat. Bradykinin inducing edema inhibition and histamine inducing edema inhibition were measured after 30 minutes of the administration, and serotonin inducing edema inhibition was measured after 3 hours of the administration. The results of the antiedema test are shown in Table 2.

TABLE 2

| Compound No. | Indazole Derivative | Bradykinin inducing edema Inhibition (%) | Histamine inducing edema Inhibition (%) | Serotonin inducing edema Inhibition (%) |
|---|---|---|---|---|
| (46) | 3-(3-Diethylaminopropylamino)-5-chloroindazole | 14.7 | 31.0 | 73.4 |
| (152) | 3-(3-Morpholinopropylamino)indazole | 37 | 20.7 | 42.9 |
| C-4 | Indomethacin (Dose: 10 mg/kg) | 0.4 | 0 | 21.4 |
| C-5 | Phenylbutazone (Dose: 100 mg/kg) | 2.9 | 0 | 2.8 |
| C-6 | Ketoprofen (Dose: 10 mg/kg) | 1.6 | 2.9 | 5.2 |

In Table 2, indomethacin [1-(p-chlorobenzoyl)-5-methoxy-2-methyl-indole-3-acetic acid; referred to as Compound No. "C-4"], phenylbutazone [3,5-dioxo-1,2-diphenyl-4-n-butylpyrazolidine; referred to as Compound No. "C-5"] and ketoprofen [3-benzoylhydratropic acid; referred to as Compound No. "C-6"] are all comparative compounds and have been actually used as medicines.

As shown in Table 2, indazole derivatives of this invention show significant pharmacological activities to the edema which is caused by chemical mediators of inflammatory reaction such as bradykinin, histamine and serotonin in comparison with Compounds C-4, C-5 and C-6.

Compound (46) having substituted amino group in the ω-position of this invention is superior to 3-amino-5-chloroindazole as described in Beck, Gunther et al., Justus Liebigs Ann. Chem. 716, 47-60 (1968). More specifically, Compound (46) obtained by introducing a diethylaminopropyl group to the 3-position of the 3-amino-5-chloroindazole can relieve the side effects of 3-amino-5-chloroindazole such as decrease of body temperature and depression of locomotor activity, in addition to the fact that Compound (46) has the same Carrageenin edema inhibition activity as 3-amino-5-chloroindazole. These effects were confirmed by the following test.

To female Wister rats weighing 130–150 g nothing was fed for 19 hours. Then, the rats were orally administered the test compound. Sixty minutes later, the pad of a hind paw of the rat was injected with 0.1 ml of 1% carrageenin solution. After edema was formed on the paw, paw volume and body temperature of the rat were measured, and movement of the rat was observed. As a result, both 3-amino-5-chloroindazole and Compound (46) show a strong inhibition to the edema, that is, 65% and 59%, respectively, after 3 hours from the injection. However, in contrast to Compound (46), 3-amino-5-chloroindazole caused to the rats decrease of body temperature of 3–4° C. and remarkable depression of locomotor activity.

Analgesic Activity

Analgesic activity was measured by orally administering 100 mg/kg of a hydrochloride of the indazole derivative of this invention as set forth in Table 3 to an animal (rat) in accordance with the standard mouse acetic acid-writing test as described in R. Koster et al., Fred. Proc., 18, 412 (1959). The test results are shown in Table 3.

TABLE 3

| Compound No. | Indazole Derivative | Inhibition (%) |
|---|---|---|
| (46) | 3-(3-Diethylaminopropylamino)-5-chloroindazole | 52 |
| (152) | 3-(3-Morpholinopropylamino)-indazole | 57 |
| C-4 | Indomethacin (Dose: 20 mg/kg) | 50 |

TABLE 3-continued

| Compound No. | Indazole Derivative | Inhibition (%) |
|---|---|---|
| C-5 | Phenylbutazone (Dose: 100 mg/kg) | 9 |

In Table 3, Compounds C-4 and C-5 are both comparative compounds.

Anti-Ulcer Test

The test compound was suspended in 1% HCO-60 (trade name for polyoxyethylene hydrogenated castor oil; a product of Nikko Chemical Co., Ltd., Japan) at the concentration of 10 mg/ml. Male donryu rats weighing 150–160 g were orally administered 100 mg/kg of the test compound. The occurrence of gastric ulcer was examined 24 hours after the administration.

When 100 mg/kg of 1-(3-diethylaminopropyl)-3-(3-piperidinopropylamino)-5-hydroxyindazole referred to as Compound (126), one of typical and preferred compounds of this invention, was singly administered at one time, gastric ulcer did not occur. Further, gastric ulcer did not occur even if Compound (126) was administered for 5 days.

It is well known that the single use of acidic non-steroidal anti-inflammatory drugs causes a side effect in digestive tract ulcers such as gastric ulcer. The inventors found, however, that the side effect could be suppressed if the acidic non-steroidal anti-inflammatory drugs were used in combination with the indazole derivatives or pharmaceutically acceptable salts thereof of this invention. For example, gastric ulcer was caused by a single administration of 10 mg/kg of indomethacin in an ulcer index of 10.2 mm, and in an occurrence frequency of 6/6 (Ulcer generation animal number/Total animal number). However, when 100 mg/kg of Compound (126) of this invention was used together with 10 mg/kg of indomethacin, the ulcer index decreased to 5.8 mm though the occurrence frequency was not changed.

Acute Toxicity

Acute toxicity was measured by intraperitoneally injecting a hydrochloride of the indazole derivative of this invention as set forth in Table 4 to male ddy mice in accordance with the ordinary method described in Finney DJ Probit Analysis University Press 48, (1952). The results are shown in Table 4.

TABLE 4

| Compound No. | Indazole Derivative | $LD_{50}$ (mg/kg) |
|---|---|---|
| (1) | 1-(3-Diethylaminopropyl)-3-amino-4-chloroindazole | 171 |
| (2) | 1-(3-Diethylaminopropyl)-3-amino-5-chloroindazole | 192 |
| (3) | 1-(3-Diethylaminopropyl)-3-amino-6-chloroindazole | 241 |
| (4) | 1-(3-Diethylaminopropyl)-3-amino-7-chloroindazole | 273 |
| (5) | 1-(3-Diethylaminopropyl)-3,5-diaminoindazole | 311 |
| (6) | 1-(3-Diethylaminopropyl)-3-amino-5-methoxyindazole | 188 |
| (7) | 1-(3-Diethylaminopropyl)-3-amino-5-methylindazole | 221 |
| (8) | 1-(3-Di-n-butylaminopropyl)-3-amino-5-chloroindazole | 231 |
| (9) | 1-(3-Dimethylaminobutyl)-3-amino-5-chloroindazole | 113 |
| (10) | 1-(3-Diethylamino-5-methylhexyl)-3-amino-5-chloroindazole | 239 |
| (11) | 1-(3-Piperidinopropyl)-3-amino-5-chloroindazole | 211 |
| (12) | 1-(6-Piperidinohexyl)-3-amino-5-chloroindazole | 337 |
| (13) | 1-(3-Piperidinobutyl)-3-amino-5-chloroindazole | 310 |
| (14) | 1-(3-Piperidino-5-methylhexyl)-3-amino-5-chloroindazole | 301 |
| (15) | 1-[3-(2-Methylpiperidino)propyl]-3-amino-5-chloroindazole | 250 |
| (16) | 1-[3-(2,6-Dimethylpiperidino)propyl]-3-amino-5-chloroindazole | 214 |
| (17) | 1-[3-(4-Hydroxypiperidino)propyl]-3-amino-5-chloroindazole | 251 |
| (18) | 1-[3-(4-Chloropiperidino)propyl]-3-amino-5-chloroindazole | 278 |
| (19) | 1-(3-Homopiperidinopropyl)-3-amino-5-chloroindazole | 251 |
| (20) | 1-[3-(4-Methylpiperazino)propyl]-3-amino-5-chloroindazole | 278 |

TABLE 4-continued

| Compound No. | Indazole Derivative | LD$_{50}$ (mg/kg) |
|---|---|---|
| (21) | 1-(3-Pyrrolidinopropyl)-3-amino-5-chloroindazole | 311 |
| (22) | 1-(3-Morpholinopropyl)-3-amino-5-chloroindazole | 388 |
| (23) | 1-(3-Diethylaminopropyl)-3-amino-4-hydroxyindazole | 179 |
| (24) | 1-(3-Diethylaminopropyl)-3-amino-5-hydroxyindazole | 161 |
| (25) | 1-(3-Diethylaminopropyl)-3-amino-6-hydroxyindazole | 301 |
| (26) | 1-(3-Diethylaminopropyl)-3-amino-7-hydroxyindazole | 297 |
| (27) | 1-(3-Diethylaminopropyl)-3-amino-5-iodoindazole | 281 |
| (28) | 1-(3-Diethylaminopropyl)-3-amino-7-iodoindazole | 103 |
| (29) | 1-(3-Diethylaminopropyl)-3,5,7-triaminoindazole | 104 |
| (30) | 1-(3-Di-n-butylaminopropyl)-3-amino-5-hydroxyindazole | 255 |
| (31) | 1-(3-Dimethylaminobutyl)-3-amino-5-hydroxyindazole | 241 |
| (32) | 1-(3-Diethylamino-5-methylhexyl)-3-amino-5-hydroxyindazole | 251 |
| (33) | 1-(3-Piperidinopropyl)-3-amino-5-hydroxyindazole | 227 |
| (34) | 1-(6-Piperidinohexyl)-3-amino-5-hydroxyindazole | 231 |
| (35) | 1-(3-Piperidinobutyl)-3-amino-5-hydroxyindazole | 246 |
| (36) | 1-(3-Piperidino-5-methylhexyl)-3-amino-5-hydroxyindazole | 251 |
| (37) | 1-[3-(2-Methylpiperidino)propyl]-3-amino-5-hydroxyindazole | 267 |
| (38) | 1-[3-(2,6-Dimethylpiperidino)propyl]-3-amino-5-hydroxy-indazole | 278 |
| (39) | 1-[3-(4-Hydroxypiperidino)propyl]-3-amino-5-hydroxyindazole | 311 |
| (40) | 1-[3-(4-Chloropiperidino)propyl]-3-amino-5-hydroxyindazole | 335 |
| (41) | 1-(3-Homopiperidinopropyl)-3-amino-5-hydroxyindazole | 340 |
| (42) | 1-[3-(4-Methylpiperazino)propyl]-3-amino-5-hydroxyindazole | 341 |
| (43) | 1-(3-Pyrrolidinopropyl)-3-amino-5-hydroxyindazole | 211 |
| (44) | 1-(3-Morpholinopropyl)-3-amino-5-hydroxyindazole | 368 |
| (45) | 3-(3-Diethylaminopropylamino)-4-chloroindazole | 271 |
| (46) | 3-(3-Diethylaminopropylamino)-5-chloroindazole | 211 |
| (47) | 3-(3-Diethylaminopropylamino)-6-chloroindazole | 278 |
| (48) | 3-(3-Diethylaminopropylamino)-7-chloroindazole | 291 |
| (49) | 3-(3-Diethylaminopropylamino)-5-aminoindazole | 244 |
| (50) | 3-(3-Diethylaminopropylamino)-5-methoxyindazole | 200 |
| (51) | 3-(3-Diethylaminopropylamino)-5-methylindazole | 231 |
| (52) | 3-(3-Di-n-butylaminopropylamino)-5-chloroindazole | 211 |
| (53) | 3-(3-Dimethylaminobutylamino)-5-chloroindazole | 313 |
| (54) | 3-(3-Diethylamino-5-methylhexylamino)-5-chloroindazole | 251 |
| (55) | 3-(3-Piperidinopropylamino)-5-chloroindazole | 133 |
| (56) | 3-(6-Piperidinohexylamino)-5-chloroindazole | 145 |
| (57) | 3-(3-Piperidinobutylamino)-5-chloroindazole | 173 |
| (58) | 3-(3-Piperidino-5-methylhexylamino)-5-chloroindazole | 180 |
| (59) | 3-[3-(2-Methylpiperidino)propylamino]-5-chloroindazole | 210 |
| (60) | 3-[3-(2,6-Dimethylpiperidino)propylamino]-5-chloroindazole | 310 |
| (61) | 3-[3-(4-Hydroxypiperidino)propylamino]-5-chloroindazole | 210 |
| (62) | 3-[3-(4-Chloropiperidino)propylamino]-5-chloroindazole | 312 |
| (63) | 3-(3-Homopiperidinopropylamino)-5-chloroindazole | 331 |
| (64) | 3-[3-(4-Methylpiperadino)propylamino]-5-chloroindazole | 229 |
| (65) | 3-(3-Pyrrolidinopropylamino)-5-chloroindazole | 136 |
| (66) | 3-(3-Morpholinopropylamino)-5-chloroindazole | 246 |
| (67) | 3-(3-Diethylaminopropylamino)-4-hydroxyindazole | 255 |
| (68) | 3-(3-Diethylaminopropylamino)-5-hydroxyindazole | 352 |
| (69) | 3-(3-Diethylaminopropylamino)-6-hydroxyindazole | 151 |
| (70) | 3-(3-Diethylaminopropylamino)-7-hydroxyindazole | 156 |
| (71) | 3-(3-Diethylaminopropylamino)-5-iodoindazole | 256 |
| (72) | 3-(3-Diethylaminopropylamino)-7-iodoindazole | 253 |
| (73) | 3-(3-Diethylaminopropylamino)-5,7-diaminoindazole | 355 |
| (74) | 3-(3-Di-n-butylaminopropylamino)-5-hydroxyindazole | 253 |
| (75) | 3-(3-Dimethylaminobutylamino)-5-hydroxyindazole | 234 |
| (76) | 3-(3-Diethylamino-5-methylhexylamino)-5-hydroxyindazole | 146 |
| (77) | 3-(3-Piperidinopropylamino)-5-hydroxyindazole | 251 |
| (78) | 3-(6-Piperidinohexylamino)-5-hydroxyindazole | 225 |
| (79) | 3-(3-Piperidinobutylamino)-5-hydroxyindazole | 146 |
| (80) | 3-(3-Piperidino-5-methylhexylamino)-5-hydroxyindazole | 332 |
| (81) | 3-[3-(2-Methylpiperidino)propylamino]-5-hydroxyindazole | 147 |
| (82) | 3-[3-(2,6-Dimethylpiperidino)propylamino]-5-hydroxyindazole | 230 |
| (83) | 3-[3-(4-Hydroxypiperidino)propylamino]-5-hydroxyindazole | 134 |
| (84) | 3-[3-(4-Chloropiperidino)propylamino]-5-hydroxyindazole | 163 |
| (85) | 3-(3-Homopiperidinopropylamino)-5-hydroxyindazole | 135 |
| (86) | 3-[3-(4-Methylpiperadino)propylamino]-5-hyroxyindazole | 123 |
| (87) | 3-(3-Pyrrolidinopropylamino)-5-hydroxyindazole | 238 |
| (88) | 3-(3-Morpholinopropylamino)-5-hydroxyindazole | 346 |
| (89) | 1-(3-Diethylaminopropyl)-3-(3-diethylaminopropylamino)-4-chloroindazole | 214 |
| (90) | 1-(3-Diethylaminopropyl)-3-(3-diethylaminopropylamino)-5-chloroindazole | 223 |
| (91) | 1-(3-Diethylaminopropyl)-3-(6-diethylaminopropylamino)-6-chloroindazole | 251 |
| (92) | 1-(3-Diethylaminopropyl)-3-(3-diethylaminopropylamino)-7-chloroindazole | 211 |
| (93) | 1-(3-Diethylaminopropyl)-3-(3-diethylaminopropylamino)-5-aminoindazole | 191 |
| (94) | 1-(3-Diethylaminopropyl)-3-(3-diethylaminopropylamino)-5-methoxyindazole | 301 |
| (95) | 1-(3-Diethylaminopropyl)-3-(3-diethylaminopropylamino)-5-methylindazole | 211 |
| (96) | 1-(3-Diethylaminopropyl)-3-(3-piperidinopropylamino)-5-chloroindazole | 243 |
| (97) | 1-(3-Diethylaminopropyl)-3-(6-piperidinohexylamino)-5-chloroindazole | 229 |
| (98) | 1-(3-Diethylaminopropyl)-3-(3-di-n-butylaminopropylamino)-5-chloroindazole | 286 |
| (99) | 1-(3-Diethylaminopropyl)-3-(3-piperidinobutylamino)-5-chloroindazole | 295 |
| (100) | 1-(3-Piperidinopropyl)-3-(3-diethylaminopropylamino)-5-chloroindazole | 281 |

TABLE 4-continued

| Compound No. | Indazole Derivative | LD$_{50}$ (mg/kg) |
|---|---|---|
| (101) | 1-(3-Piperidinopropyl)-3-(3-piperidinopropylamino)-5-chloroindazole | 211 |
| (102) | 1-(3-Piperidinopropyl)-3-(6-piperidinohexylamino)-5-chloroindazole | 255 |
| (103) | 1-(3-Piperidinopropyl)-3-(3-piperidinobutylamino)-5-chloroindazole | 261 |
| (104) | 1-(3-Piperidinobutyl)-3-(3-diethylaminopropylamino)-5-chloroindazole | 277 |
| (105) | 1-(3-Piperidinobutyl)-3-(3-piperidinopropylamino)-5-chloroindazole | 231 |
| (106) | 1-(3-Piperidinobutyl)-3-(3-piperidino-5-methylhexylamino)-5-chloroindazole | 228 |
| (107) | 1-(3-Piperidinobutyl)-3-(3-dimethylaminobutylamino)-5-chloroindazole | 231 |
| (108) | 1-(3-Dimethylaminobutyl)-3-(3-diethylaminopropylamino)-5-chloroindazole | 118 |
| (109) | 1-(3-Dimethylaminobutyl)-3-(3-piperidinopropylamino)-5-chloroindazole | 387 |
| (110) | 1-(3-Dimethylaminobutyl)-3-(3-piperidinobutylamino)-5-chloroindazole | 293 |
| (111) | 1-(3-Dimethylaminobutyl)-3-(3-diethylamino-5-methylhexylamino)-5-chloroindazole | 314 |
| (112) | 1-(3-Pyrrolidinopropyl)-3-(3-homopiperidinopropylamino)-5-chloroindazole | 325 |
| (113) | 1-(3-Pyrrolidinopropyl)-3-[3-(2-methylpiperidino)propylamino]-5-chloroindazole | 221 |
| (114) | 1-(3-Pyrrolidinopropyl)-3-[3-(4-methylpiperazino)propylamino]-5-chloroindazole | 299 |
| (115) | 1-(3-Morpholinopropyl)-3-(3-diethylaminopropylamino)-5-chloroindazole | 301 |
| (116) | 1-(3-Morpholinopropyl)-3-[3-(2,6-dimethylpiperidino)propylamino]-5-chloroindazole | 311 |
| (117) | 1-(3-Morpholinopropyl)-3-[3-(4-chloropiperidino)propylamino]-5-chloroindazole | 291 |
| (118) | 1-(3-Morpholinopropyl)-3-[3-(4-hydroxypiperidino)propylamino]-5-chloroindazole | 287 |
| (119) | 1-(3-Diethylaminopropyl)-3-(3-diethylaminopropylamino)-4-hydroxyindazole | 271 |
| (120) | 1-(3-Diethylaminopropyl)-3-(3-diethylaminopropylamino)-5-hydroxyindazole | 269 |
| (121) | 1-(3-Diethylaminopropyl)-3-(3-diethylaminopropylamino)-6-hydroxyindazole | 251 |
| (122) | 1-(3-Diethylaminopropyl)-3-(3-diethylaminopropylamino)-7-hydroxyindazole | 245 |
| (123) | 1-(3-Diethylaminopropyl)-3-(3-diethylaminopropylamino)-5-iodoindazole | 291 |
| (124) | 1-(3-Diethylaminopropyl)-3-(3-diethylaminopropylamino)-7-iodoindazole | 313 |
| (125) | 1-(3-Diethylaminopropyl)-3-(3-diethylaminopropylamino)-5,7-diaminoindazole | 320 |
| (126) | 1-(3-Diethylaminopropyl)-3-(3-piperidinopropylamino)-5-hydroxyindazole | 310 |
| (127) | 1-(3-Diethylaminopropyl)-3-(6-piperidinohexylamino)-5-hydroxyindazole | 198 |
| (128) | 1-(3-Diethylaminopropyl)-3-(3-di-n-butylaminopropylamino)-5-hydroxyindazole | 170 |
| (129) | 1-(3-Diethylaminopropyl)-3-(3-piperidinobutylamino)-5-hydroxyindazole | 240 |
| (130) | 1-(3-Piperidinopropyl)-3-(3-diethylaminopropylamino)-5-hydroxyindazole | 211 |
| (131) | 1-(3-Piperidinopropyl)-3-(3-piperidinopropylamino)-5-hydroxyindazole | 298 |
| (132) | 1-(3-Piperidinopropyl)-3-(6-piperidinohexylamino)-5-hydroxyindazole | 310 |
| (133) | 1-(3-Piperidinopropyl)-3-(3-piperidinobutylamino)-5-hydroxyindazole | 330 |
| (134) | 1-(3-Piperidinobutyl)-3-(3-diethylaminopropylamino)-5-hydroxyindazole | 349 |
| (135) | 1-(3-Piperidinobutyl)-3-(3-piperidinopropylamino)-5-hydroxyindazole | 298 |
| (136) | 1-(3-Piperidinobutyl)-3-(3-piperidino-5-methylhexylamino)-5-hydroxyindazole | 241 |
| (137) | 1-(3-Piperidinobutyl)-3-(3-dimethylaminobutylamino)-5-hydroxyindazole | 258 |
| (138) | 1-(3-Dimethylaminobutyl)-3-(3-diethylaminopropylamino)-5-hydroxyindazole | 213 |
| (139) | 1-(3-Dimethylaminobutyl)-3-(3-piperidinopropylamino)-5-hydroxyindazole | 249 |
| (140) | 1-(3-Dimethylaminobutyl)-3-(3-piperidinobutylamino)-5-hydroxyindazole | 313 |
| (141) | 1-(3-Dimethylaminobutyl)-3-(3-diethylamino-5-methylhexylamino)-5-hydroxyindazole | 340 |
| (142) | 1-(3-Pyrrolidinopropyl)-3-(3-homopiperidinopropylamino)-5-hydroxyindazole | 349 |
| (143) | 1-(3-Pyrrolidinopropyl)-3-[3-(2-methylpiperidino)propylamino]-5-hydroxyindazole | 291 |
| (144) | 1-(3-Pyrrolidinopropyl)-3-[3-(4-methylpiperazino)propylamino]-5-hydroxyindazole | 281 |
| (145) | 1-(3-Morpholinopropyl)-3-(3-diethylaminopropylamino)-5-hydroxyindazole | 211 |
| (146) | 1-(3-Morpholinopropyl)-3-[3-(2,6-dimethylpiperidino)propylamino]-5-hydroxyindazole | 198 |
| (147) | 1-(3-Morpholinopropyl)-3-[3-(4-chloropiperidino)propylamino]-5-hydroxyindazole | 181 |
| (148) | 1-(3-Morpholinopropyl)-3-[3-(4-hydroxypiperidino)propylamino]-5-hydroxyindazole | 245 |
| (149) | 1-(3-Morpholinopropyl)-3-aminoindazole | 261 |
| (150) | 1-(3-Morpholinobutyl)-3-aminoindazole | 270 |
| (151) | 1-(2-Morpholinoethyl)-3-aminoindazole | 290 |
| (152) | 3-(3-Morpholinopropylamino)indazole | 389 |
| (153) | 3-(3-Morpholinobutylamino)indazole | 331 |
| (154) | 3-(2-Morpholinoethylamino)indazole | 351 |
| (155) | 1-(3-Morpholinopropyl)-3-(3-diethylaminopropylamino)indazole | 291 |
| (156) | 1-(3-Morpholinopropyl)-3-[3-(2,6-dimethylpiperidino)propylamino]indazole | 301 |
| (157) | 1-(3-Morpholinopropyl)-3-[3-(4-chloropiperidino)propylamino]indazole | 251 |
| (158) | 1-(3-Morpholinopropyl)-3-[3-(4-hydroxypiperidino)propylamino]indazole | 288 |
| (159) | 1-(3-Di-n-butylaminopropyl)-3-(3-morpholinopropylamino)indazole | 191 |
| (160) | 1-(3-Piperidinopropyl)-3-(3-morpholinopropylamino)indazole | 244 |
| (161) | 3-Amino-4-hydroxyindazole | 211 |
| (162) | 3-Amino-5-hydroxyindazole | 243 |
| (163) | 3-Amino-6-hydroxyindazole | 252 |
| (164) | 3-Amino-7-hydroxyindazole | 231 |
| (165) | 3-Amino-5-iodoindazole | 242 |
| (166) | 3-Amino-7-iodoindazole | 198 |
| (167) | 3,5,7-Triaminoindazole | 171 |

As shown in Table 4, the toxicity of the indazole derivatives is very low. The acute toxicity (LD$_{50}$) ranged from 50 mg/kg to 400 mg/kg.

The following examples illustrate the present invention in more detail, but they are given for illustrative purposes only and are not to be construed as limiting the invention. In the following referential examples, ω-halogenoalkylamine salts were synthesized from the corresponding phenoxyalkylaldehydes, phenoxyalkylketoalkylhalides or dihalogenoalkyl compounds in accordance with the general synthetic methods described in Marvel et al., J. Am. Chem. Soc. 63 1894 (1941), Norris., J. Am. Chem. Soc. 38 642 (1907), H. Franke and R. Paitch, J. med. Chem. 9 643 (1966). C. S. Marvel et al., J. Am. Chem. Soc., 49 2299 (1927) or H. C. Brill, J. Am. Chem. Soc., 47 1134 (1925).

REFERENTIAL EXAMPLE 1

1-(2-Bromoethyl)piperidine hydrobromide

In a mixed solution consisting of 50 g of 1,2-dibromoethane, 18.5 g of phenol and 100 ml of water was added dropwise 30 ml of water containing therein 7.9 g of sodium hydroxide at a temperature of 130° C. over 30 minutes with stirring, and the reaction solution was further stirred for 6 hours. After completion the reaction, the organic layer was separated from the reaction solution, washed twice with a saturated aqueous potassium carbonate solution, washed twice with water and dried over anhydrous sodium sulfate. The organic layer was separated by filtration and condensed under reduced pressure to give 34.3 g of 2-phenoxyethyl bromide having a boiling point of 105° C. to 107° C. at 6 mmHg in a yield of 85%.

A mixture of 20 g of 2-phenoxyethyl bromide thus obtained, 7.92 g of piperidine and 12.86 g of potassium carbonate was added into 100 ml of ethyl alcohol and stirred for 6 hours at 100° C. The reaction mixture was filtered and condensed under reduced pressure to give 18.4 g of 1-(2-phenoxyethyl)piperidine having a boiling point of 111° C. to 112° C. at 7 mmHg in a yield of 90%.

15 g of the 1-(2-phenoxyethyl)piperidine thus obtained was reacted with 30 ml of 40% hydrobromic acid at 150° C. for 7 hours with stirring. The reaction solution was cooled, added with 20 ml of chloroform and then the chloroform layer was separated. The hydrobromic acid layer was condensed under reduced pressure and the residue was recrystallized from 5 ml of ethyl alcohol to give 15.1 g of 1-(2-bromoethyl)piperidine hydrobromide having a melting point of 89° C. to 91° C. in a yield of 79%.

Elemental Analysis Value: $C_7H_{15}NBr_2$:
Calcd.(%): C 30.80; H 5.54; N 5.13; Br 58.53.
Found (%): C 30.71; H 5.68; N 5.01; Br 58.60.

In the same manner as described above were obtained other ω-halogenoalkylamine salts as set forth in Table 5-3 using the reaction conditions as set forth in Tables 5-1, 5-2 and 5-3.

TABLE 5-1

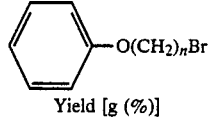

| Run No. | Br(CH$_2$)$_n$Br n | (g) | Phenol (g) | Water (ml) | Aq.NaOH soln. NaOH (g) | Water (ml) | Reaction Temperature (°C.) | Reaction Time (hr) | Yield [g (%)] |
|---|---|---|---|---|---|---|---|---|---|
| 1 | 3 | 53.7 | 18.5 | 100 | 7.9 | 30 | 130 | 6.5 | 87 |
| 2 | 6 | 64.9 | 18.5 | 100 | 7.9 | 30 | 130 | 6.5 | 78 |
| 3 | 3 | 53.7 | 18.5 | 100 | 7.9 | 30 | 130 | 6.5 | 81 |
| 4 | 3 | 53.7 | 18.5 | 100 | 7.9 | 30 | 130 | 6.5 | 89 |
| 5 | 3 | 53.7 | 18.5 | 100 | 7.9 | 30 | 130 | 6.5 | 85 |
| 6 | 3 | 53.7 | 18.5 | 100 | 7.9 | 30 | 130 | 6.5 | 83 |
| 7 | 3 | 53.7 | 18.5 | 100 | 7.9 | 30 | 130 | 6.5 | 83 |
| 8 | 3 | 53.7 | 18.5 | 100 | 7.9 | 30 | 130 | 6.5 | 87 |
| 9 | 3 | 53.7 | 18.5 | 100 | 7.9 | 30 | 130 | 6.5 | 82 |
| 10 | 3 | 53.7 | 18.5 | 100 | 7.9 | 30 | 130 | 6.5 | 79 |
| 11 | 2 | 50.0 | 18.5 | 100 | 7.9 | 30 | 130 | 6.5 | 80 |
| 12 | 3 | 53.7 | 18.5 | 100 | 7.9 | 30 | 130 | 6.5 | 83 |
| 13 | 3 | 53.7 | 18.5 | 100 | 7.9 | 30 | 130 | 6.5 | 81 |

TABLE 5-2

| Run No. | Phenoxyalkyl bromide $\text{C}_6\text{H}_5\text{O(CH}_2)_n\text{Br}$ n | (g) | Amine | (g) | Potassium Carbonate (g) | Reaction Medium $\text{C}_2\text{H}_5\text{OH}$ (ml) | Reaction Temperature (°C.) | Reaction Time (hr) | 1-(n-Phenoxyalkyl)amine | (g) | Yield (%) |
|---|---|---|---|---|---|---|---|---|---|---|---|
| 1 | 3 | 21.40 | piperidine (NH) | 7.92 | 12.86 | 100 | 100 | 6 | 1-(3-phenoxypropyl)piperidine | 18.41 | 89 |
| 2 | 6 | 25.58 | piperidine (NH) | 7.92 | 12.86 | 100 | 100 | 6 | 1-(6-phenoxyhexyl)piperidine | 21.60 | 83 |
| 3 | 3 | 21.40 | pyrrolidine (NH) | 6.62 | 12.86 | 100 | 100 | 6 | 1-(3-phenoxypropyl)pyrrolidine | 18.60 | 91 |
| 4 | 3 | 21.40 | hexamethyleneimine (NH) | 9.22 | 12.86 | 100 | 100 | 6 | 1-(3-phenoxypropyl)hexamethyleneimine | 19.52 | 84 |
| 5 | 3 | 21.40 | 2-methylpiperidine | 9.22 | 12.86 | 100 | 100 | 6 | 1-(3-phenoxypropyl)-2-methylpiperidine | 18.82 | 81 |
| 6 | 3 | 21.40 | 2,6-dimethylpiperidine | 10.53 | 12.86 | 100 | 100 | 6 | 1-(3-phenoxypropyl)-2,6-dimethylpiperidine | 19.95 | 81 |
| 7 | 3 | 21.40 | 4-hydroxypiperidine | 9.41 | 12.86 | 100 | 100 | 6 | 1-(3-phenoxypropyl)-4-hydroxypiperidine | 17.11 | 73 |

TABLE 5-2-continued

| Run No. | O(CH₂)ₙBr n | (g) | Amine | (g) | Potassium Carbonate (g) | Reaction Medium C₂H₅OH (ml) | Reaction Temperature (°C.) | Reaction Time (hr) | 1-(n-Phenoxyalkyl)amine | (g) | Yield (%) |
|---|---|---|---|---|---|---|---|---|---|---|---|
| 8 | 3 | 21.40 | 4-Cl-piperidine (NH) | 11.12 | 12.86 | 100 | 100 | 6 | 4-Cl-piperidinyl-N(CH₂)₃O-Ph | 20.56 | 81 |
| 9 | 3 | 21.40 | (C₂H₅)₂NH | 6.80 | 12.86 | 100 | 100 | 6 | (C₂H₅)₂N(CH₂)₃O-Ph | 18.58 | 90 |
| 10 | 3 | 21.40 | (C₄H₉)₂NH | 12.02 | 12.86 | 100 | 100 | 6 | (C₄H₉)₂N(CH₂)₃O-Ph | 23.35 | 89 |
| 11 | 2 | 20.00 | (CH₃)₂NH | 4.19 | 12.86 | 100 | 100 | 6 | (CH₃)₂N(CH₂)₂O-Ph | 14.57 | 88 |
| 12 | 3 | 21.40 | N-methylpiperazine | 9.32 | 12.86 | 100 | 100 | 6 | N-methylpiperazinyl-N(CH₂)₃O-Ph | 21.23 | 91 |
| 13 | 3 | 21.40 | morpholine | 8.11 | 12.86 | 100 | 100 | 6 | morpholinyl-N(CH₂)₃O-Ph | 18.58 | 89 |

TABLE 5-3

| Run No. | 1-(n-Phenoxyalkyl)amine | (g) | 40% Hydrobromic Acid (ml) | Reaction Temperature (°C.) | Reaction Time (hr) | 1-Halogenoalkylamine Salt | Yield(%) | NMR δ (CH₃)₃Si(CH₂)₃SO₃Na; D₂O | Elemental Analysis Value Calcd.(%) | Found(%) |
|---|---|---|---|---|---|---|---|---|---|---|
| 1 | [cyclohexyl-N(CH₂)₃O-phenyl] | 16.02 | 30 | 150 | 7 | [cyclohexyl-N(CH₂)₃Br·HBr] | 71 | 1.77 (m, 6H) 2.37 (m, 2H) 3.33 (m, 6H) 3.57 (t, 2H) | C₈H₁₇NBr₂ C 33.48 H 5.97 N 4.88 Br 55.67 | C 33.31 H 5.98 N 4.91 Br 55.80 |
| 2 | [cyclohexyl-N(CH₂)₆O-phenyl] | 19.10 | 30 | 150 | 7 | [cyclohexyl-N(CH₂)₆Br·HBr] | 73 | 1.64 (m, 14H) 3.35 (m, 6H) 3.59 (t, 2H) | C₁₁H₂₃NBr₂ C 40.14 H 7.04 N 4.26 Br 48.56 | C 40.17 H 7.25 N 4.13 Br 48.45 |
| 3 | [cyclopentyl-N(CH₂)₃O-phenyl] | 15.00 | 30 | 150 | 7 | [cyclopentyl-N(CH₂)₃Br·HBr] | 68 | 2.13 (m, 6H) 3.47 (m, 8H) | C₇H₁₃NBr₂ C 30.80 H 5.54 N 5.13 Br 58.53 | C 30.67 H 5.31 N 5.34 Br 58.68 |
| 4 | [cycloheptyl-N(CH₂)₃O-phenyl] | 17.05 | 30 | 150 | 7 | [cycloheptyl-N(CH₂)₃Br·HBr] | 79 | 1.73 (bs, 8H) 2.35 (m, 2H) 3.34 (m, 6H) 3.53 (t, 2H) | C₉H₁₉NBr₂ C 35.91 H 6.36 N 4.65 Br 53.08 | C 36.08 H 6.42 N 4.48 Br 53.02 |
| 5 | [2-methylcyclohexyl-N(CH₂)₃O-phenyl] | 17.05 | 30 | 150 | 7 | [2-methylcyclohexyl-N(CH₂)₃Br·HBr] | 65 | 1.40 (d, 3H) 1.80 (bs, 6H) 2.35 (m, 2H) 3.37 (m, 5H) 3.53 (t, 2H) | C₉H₁₉NBr₂ C 35.91 H 6.36 N 4.65 Br 53.08 | C 35.82 H 6.27 N 4.78 Br 53.13 |
| 6 | [2,6-dimethylcyclohexyl-N(CH₂)₃O-phenyl] | 18.07 | 30 | 150 | 7 | [2,6-dimethylcyclohexyl-N(CH₂)₃Br·HBr] | 74 | 1.33 (d, 6H) 1.65 (bs, 8H) 2.23 (m, 2H) 3.45 (m, 4H) | C₁₀H₂₁NBr₂ C 38.12 H 6.72 N 4.45 Br 50.71 | C 38.21 H 6.85 N 4.27 Br 50.67 |
| 7 | [4-hydroxycyclohexyl-N(CH₂)₃O-phenyl] | 17.19 | 30 | 150 | 7 | [4-hydroxycyclohexyl-N(CH₂)₃Br·HBr] | 69 | 1.77 (m, 4H) 2.15 (m, 3H) 2.83 (m, 6H) 3.82 (t, 2H) | C₈H₁₇NOBr₂ C 31.71 H 5.65 N 4.62 Br 52.74 | C 31.55 H 5.72 N 4.71 Br 52.55 |

TABLE 5-3-continued

| Run No. | 1-(n-Phenoxyalkyl)amine | (g) | 40% Hydrobromic Acid (ml) | Reaction Temperature (°C.) | Reaction Time (hr) | 1-Halogenoalkylamine Salt | Yield(%) | NMR δ (CH₃)₃Si(CH₂)₃SO₃Na; D₂O | Elemental Analysis Value Calcd.(%) Found(%) |
|---|---|---|---|---|---|---|---|---|---|
| 8 | 4-Cl-cyclohexyl-N(CH₂)₃O-C₆H₅ | 18.54 | 30 | 150 | 7 | 4-Cl-cyclohexyl-N(CH₂)₃Br·HBr | 71 | 1.63 (m, 4H) 2.15 (m, 3H) 2.85 (m, 6H) 3.87 (t, 2H) | C₈H₁₆NClBr₂ C 29.88 C 29.71 H 5.02 H 4.91 N 4.36 N 4.63 Cl 11.03 Cl 11.31 Br 49.71 Br 49.44 |
| 9 | (C₂H₅)₂N(CH₂)₃O-C₆H₅ | 15.15 | 30 | 150 | 7 | (C₂H₅)₂N(CH₂)₃Br·HBr | 78 | 1.30 (t, 6H) 2.30 (m, 2H) 3.30 (m, 8H) | C₇H₁₇NBr₂ C 30.57 C 30.49 H 6.23 H 6.22 N 5.09 N 5.23 Br 58.11 Br 58.06 |
| 10 | (C₄H₉)₂N(CH₂)₃O-C₆H₅ | 19.25 | 30 | 150 | 7 | (C₄H₉)₂N(CH₂)₃Br·HBr | 66 | 1.05 (m, 6H) 1.58 (m, 8H) 2.32 (m, 2H) 3.35 (m, 8H) | C₁₁H₂₅NBr₂ C 39.90 C 39.81 H 7.61 H 7.55 N 4.23 N 4.53 Br 48.26 Br 48.11 |
| 11 | (CH₃)₂N(CH₂)₂O-C₆H₅ | 12.07 | 30 | 150 | 7 | (CH₃)₂N(CH₂)₂Br·HBr | 78 | 2.93 (s, 6H) 3.70 (bs, 4H) | C₄H₁₁NBr₂ C 20.63 C 20.71 H 4.76 H 4.83 N 6.01 N 5.95 Br 68.60 Br 68.51 |
| 12 | CH₃N(piperazinyl)(CH₂)₃O-C₆H₅ | 17.12 | 30 | 150 | 7 | CH₃N(piperazinyl)(CH₂)₃Br·2HBr | 71 | 2.37 (m, 2H) 3.03 (s, 3H) 3.73 (m, 12H) | C₈H₁₈N₂Br₂ C 31.81 C 31.77 H 6.01 H 5.98 N 9.28 N 9.51 Br 52.90 Br 52.74 |
| 13 | (morpholinyl)N(CH₂)₃O-C₆H₅ | 16.17 | 30 | 150 | 7 | (morpholinyl)N(CH₂)₃Br·HBr | 73 | 2.36 (m, 2H) 3.32 (m, 6H) 3.80 (m, 6H) | C₇H₁₅NOBr₂ C 29.09 C 29.13 H 5.23 H 5.19 N 4.85 N 4.87 Br 55.30 Br 55.26 |

REFERENCE EXAMPLE 3

Syntheses of 1-(1-alkyl-3-bromopropyl)piperidine hydrobromides 1-(1-Methyl-3-bromopropyl)piperidine hydrobromide 1-(1-Methyl-3-bromopropyl)piperidine hydrobromide was obtained in accordance with the following equations:

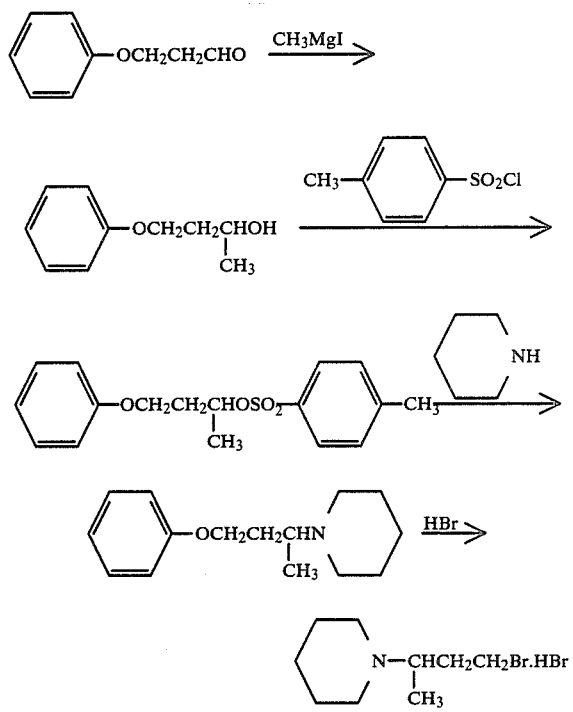

24.9 g of methyl iodide was reacted with 7.26 g of magnesium in 150 ml of anhydrous diethyl ether to obtain methylmagnesium iodide by Grignard reaction. To a solution consisting of 20 g of 3-phenoxypropionaldehyde and 200 ml of anhydrous diethyl ether was added dropwise the methylmagnesium while maintaining a temperature of not more than 20° C. The reaction solution was added with 25 ml of concentrated hydrochloric acid, and then the diethyl ether layer was separated from an aqueous layer. The ether layer was washed with an aqueous sodium bicarbonate solution, washed with water, dried over anhydrous sodium sulfate and then condensed under reduced pressure to obtain 15.0 g of 4-phenoxy-2-butanol having a boiling point of 61° C. to 62° C. at 3 mmHg in a yield of 67%.

10 g of the 4-phenoxy-2-butanol was reacted with 13.9 g of p-toluenesulfonyl chloride in 21.2 ml of 5N-sodium hydroxide in accordance with the method described in Norris, J. Am. Chem. Sec. 38, 642(1907) to obtain 18.9 g of 4-phenoxy-2-butyl-p-toluene sulfonate (4-phenoxy-2-butyl tosylate) having a boiling point of 170° C. to 171° C. at 2 mmHg in a yield of 89%.

In a sealed tube, 10 g of the 4-phenoxy-2-butyl tosylate was reacted with 11.2 g of piperidine in 60 ml of absolute methyl alcohol for one hour at 125° C. After the reaction solution was condensed under reduced pressure, 100 ml of diethyl ether was added into the solution, and then the solution was separated into the diethyl ether solution and 20% aqueous sodium hydroxide solution. After the ether layer was dried over anhydrous sodium sulfate, ether was removed under reduced pressure therefrom. The residue thus obtained was subjected to an alumina-column chromatography using chloroform as the developing solvent to give 5.46 g of 1-(1-methyl-3-phenoxypropyl)piperidine in a yield of 75%.

5 g of the 1-(1-methyl-3-phenoxypropyl)piperidine thus obtained was reacted with 30 ml of 40% hydrobromic acid at 150° C for 7 hours with stirring. The reaction solution was cooled and added with 20 ml of chloroform. Then, the hydrobromic acid layer was separated from the chloroform layer. The hydrobromic acid was removed under reduced pressure and the residue was recrystallized from 5 ml of ethyl alcohol to give 4.84 g of 1-(1-methyl-3-bromopropyl)piperidine hydrobromide in a yield of 75%.

Elemental Analysis Value: $C_9H_{19}NBr_2$: Calcd. (%): C 35.91; H 6.36; N 4.65; Br 53.08. Found (%): C 35.95; H 6.31; N 4.81; Br 52.93.

1-(1-Isobutyl-3-bromopropyl)piperidine hydrobromide

The above described procedures were repeated except that 24.0 g of isobutyl bromide was employed instead of 24.9 g of methyl iodide, and then 5.74 g of 1-(1-isobutyl-3-bromopropyl)piperidine hydrobromide was obtained in a yield of 78%.

Elemental Analysis Value: $C_{12}H_{25}NBr_2$: Calcd.(%): C 42.00; H 7.35; N 4.08; Br 46.57. Found (%): C 42.11; H 7.39; N 3.89; Br 46.61.

REFERENTIAL EXAMPLE 3

Syntheses of 1-alkyl-3-bromopropyldiethylamines

1-Methyl-3-bromopropyldiethylamine

1-Methyl-3-bromopropyldiethylamine was prepared in accordance with the following equations:

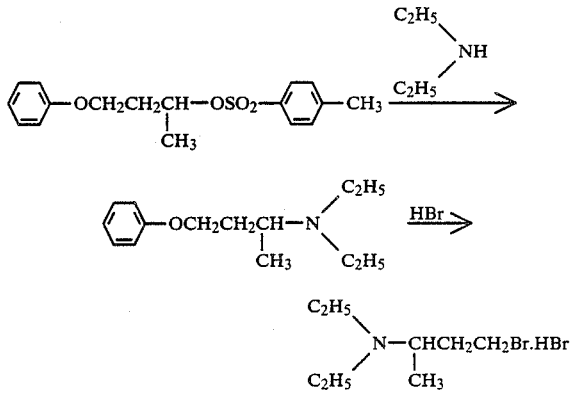

To 60 ml of absolute methyl alcohol were added 10 g of 4-phenoxy-2-butyl tosylate and 9.62 g of diethylamine. The mixture was reacted in a sealed tube for one hour at 125° C. After the reaction solution was condensed under reduced pressure, 100 ml of diethyl ether was added into the solution, and then the solution was separated into the diethyl ether solution and 20% aqueous sodium hydroxide solution. The ether layer was dried over anhydrous sodium sulfate, and the ether was removed under reduced pressure therefrom. The residue thus obtained was subjected to an alumina-column chromatography using chloroform as the developing solvent to give 5.32 g of 1-methyl-3-phenoxypropyldiethylamine in a yield of 77%.

5 g of the 1-methyl-3-phenoxypropyldiethylamine was reacted with 30 ml of 40% hydrobromic acid at 150° C. for 7 hours with stirring. The reaction solution was cooled and added with 20 ml of chloroform, and then the hydrobromic acid layer was separated from the chloroform layer. The hydrobromic acid was removed under reduced pressure and the residue was recrystallized from 5 ml of ethyl alcohol to give 4.88 g of 1-methyl-3-bromopropyldiethylamine hydrobromide in a yield of 78%.

Elemental Analysis Value: $C_8H_{19}NBr_2$: Calcd.(%): C 33.24; H 6.63; N 4.85; Br 55.28. Found (%): C 33.37; H 6.69; N 4.69; Br 55.25.

1-Isobutyl-3-bromopropyldiethylamine hydrobromide

The procedures of obtaining the tosylate as described in Referential Example 2 were repeated except that 24.0 g of isobutyl bromide was employed instead of the 24.9 g of methyl iodide, and 2-methyl-6-phenoxyhexyl tosylate was obtained.

The procedures of preparing 1-methyl-3-bromopropyldiethylamine as described above were repeated except that 11.31 g of 2-methyl-6-phenoxyhexyl tosylate was employed instead of the 10 g of 4-phenoxy-2-butyl tosylate, and 5.33 g of 1-isobutyl-3-bromopropyldiethylamine hydrobromide was obtained in a yield of 75%.

Elemental Analysis Value: $C_{11}H_{25}NBr_2$: Calcd.(%): C 39.90; H 7.61; N 4.23; Br 48.26. Found (%): C 39.89; H 7.83; N 4.10; Br 48.18.

REFERENTIAL EXAMPLE 4

Syntheses of 1-alkyl-3-bromopropyldimethylamines

1-Methyl-3-bromopropyldimethylamine

1-Methyl-3-bromopropyldimethylamine was obtained in accordance with the following equations:

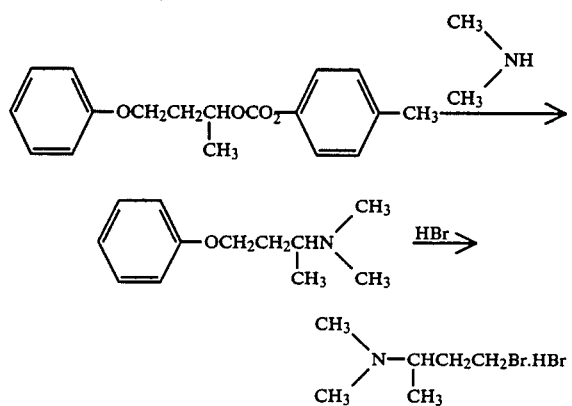

To 60 ml of absolute methyl alcohol were added 10 g of 4-phenoxy-2-butyl tosylate and 5.93 g of dimethylamine. The mixture was reacted in a sealed tube for one hour at 125° C. After the reaction solution was condensed under reduced pressure, 100 ml of diethyl ether was added into the solution and the solution was separated into the diethyl ether solution and 20% aqueous sodium hydroxide solution. The ether layer was dried over anhydrous sodium sulfate, and then the ether was removed under reduced pressure therefrom. The residue thus obtained was subjected to an alumina-column chromatography using chloroform as the developing solvent to give 3.98 g of 1-methyl-3-phenoxypropyldimethylamine in a yield of 66%.

5 g of the 1-methyl-3-phenoxypropyldimethylamine thus obtained was reacted with 30 ml of 40% hydrobromic acid at 150° C. for 7 hours with stirring. The reaction solution was cooled and added with 20 ml of chloroform, and then the hydrobromic acid layer was separated from the chloroform layer. The hydrobromic acid was removed under reduced pressure and the residue was recrystallized from 5 ml of ethyl alcohol to give 4.46 g of 1-methyl-3-bromopropyldimethylamine hydrobromide in a yield of 79%.

Elemental Analysis Value: $C_6H_{15}NBr_2$: Calcd.(%): C 27.61; H 5.79; N 5.37; Br 61.23. Found (%): C 27.57; H 5.91; N 5.28; Br 61.24.

1-Isobutyl-3-bromopropyldimethylamine hydrobromide

The above described procedures were repeated except that 11.31 g of 2-methyl-6-phenoxyhexyl tosylate obtained in Referential Example 3 was employed instead of the 10 g of 4-phenoxy-2-butyl tosylate, and 5.02 g of 1-isobutyl-3-bromopropyldimethylamine hydrobromide was obtained in a yield of 77%.

Elemental Analysis Value: $C_9H_{21}NBr_2$: Calcd.(%): C 35.67; H 6.98; N 4.62; Br 52.73. Found (%): C 35.91; H 6.71; N 4.66; Br 52.72.

EXAMPLE 1

3-Amino-4-chloroindazole was prepared in accordance with the method described in Beck, Gunkther, et al., Justus Liebigs Ann. Chem., 716 47 (1968).

To 50 ml of dioxane were added 5.66 g of 3-amino-4-chloroindazole thus obtained and 6.68 g of phthalic anhydride, and the mixture was stirred for 5 hours at 120° C. After the mixture was condensed under reduced pressure, the condensed residue was added with 30 ml of diethyl ether and stirred under cooling with ice and water for 30 minutes to separate crystals. Then the crystals were obtained by filtration and dried under reduced pressure to give 9.96 g of 3-phthalimido-4-chloroindazole having the following analytical values in a yield of 89%.

IR absorption spectrum ($\nu_{max}$, cm$^{-1}$): 3300, 1785, 1735 and 1620.

NMR spectrum [$\delta$,$(CD_3)_2SO$]: 7.52(m, 7H) and 13.20(bs, 1H).

Mass spectrum (m/e): 297(M+), 299(M+2), 270(M-27), 253(M-44), 241(M-56) and 226(M-71).

To 60 ml of anhydrous N,N-dimethylformamide were added 4.54 g of 3-phthalimido-4-chloroindazole, 4.83 g of 3-bromopropyldiethylamine hydrobromide as obtained in Referential Example 1 and 6.3 g of anhydrous potassium carbonate, and the mixture was stirred for 12 hours at 80° C. After cooling the mixture, the mixture was added with 80 ml of water, and the reaction product was extracted with diethyl ether. The ether layer was extracted three times with 2N-hydrochloric acid. Then the hydrochloric acid layer was washed with diethyl ether and the pH of the layer was adjusted to at least 11 with potassium carbonate. The layer was extracted with chloroform and the chloroform layer was dried over anhydrous sodium sulfate, and then chloroform was removed under reduced pressure to give 3.70 g of 1-(3-diethylaminopropyl)-3-phthalimido-4-chloroindazole having the following analytical values in a yield of 59%.

IR absorption spectrum ($\nu_{max}$, cm$^{-1}$): 3040, 2960, 1780, 1730 and 1615.

NMR spectrum [δ,CDCl$_3$]: 0.96(t, 6H), 2.34(m, 4H), 2.47(q, 4H), 4.25(t, 2H) and 7.18(m, 7H).

Mass spectrum (m/e): 410(M$^+$), 412(M+2), 326(M-84), 312(M-98) and 298(M-112).

To 70 ml of ethyl alcohol was added 3.50 g of 1-(3-diethylaminopropyl)-3-phthalimido-4-chloroindazole. The mixture was added with 2.50 g of 85% hydrazine hydrate under cooling with ice and stirred for 3 hours under cooling with ice. The reaction mixture was filtered and the filtrate was condensed under reduced pressure. The condensed residue was added with 20 ml of water and extracted with chloroform. The chloroform layer was extracted with 2N-hydrochloric acid and the pH of the hydrochloric acid layer was adjusted to 10 with potassium carbonate. The alkali layer was extracted with chloroform. The chloroform layer was dried over anhydrous sodium sulfate and chloroform was removed under reduced pressure to give 2.03 g of 1-(3-diethylaminopropyl)-3-amino-4-chloroindazole having the following analytical values in a yield of 85%.

IR absorption spectrum ($\nu_{max}$, cm$^{-1}$): 3310, 3230, 2940, 2850, 1615 and 1580.

NMR spectrum [δ,CDCl$_3$]: 0.97(t, 6H), 2.35(m, 4H), 2.48(q, 4H), 4.20(t, 2H), 5.30(bs, 2H), 7.27(s, 2H) and 7.69(s, 1H).

Mass spectrum (m/e): 281(M$^+$), 283(M+1), 252(M-29), 223(M-58), 209(M-72) and 195(M-86).

In 15 ml of absolute ethyl alcohol was dissolved 1.50 g of 1-(3-diethylaminopropyl)-3-amino-4-chloroindazole and into the solution was introduced dried hydrogen chloride gas under cooling with ice. To the solution was added anhydrous diethyl ether to separate crystals. Then the crystals were obtained by filtration and dried to give 1-(3-diethylaminopropyl)-3-amino-4-chloroindazole dihydrochloride having the following analytical value.

Elemental Analysis Value: $C_{14}H_{23}N_4Cl_3$: Calcd.(%): C 47.54; H 6.55; N 15.84; Cl 30.07. Found (%): C 47.68; H 6.81; N 15.59; Cl 29.92.

EXAMPLE 2-4

The same procedures as described in Example 1 were repeated except that 3-aminoindazoles having a chlorine atom in either 5-, 6- or 7-position of the benzene ring as set forth in Table 6 were employed instead of the 5.66 g of 3-amino-4-chloroindazole. The 3-aminoindazoles as set forth in Table 6 were synthesized from 5-chloroanthranilonitrile, 4-chloroanthranilonitrile and 3-chloroanthranilonitrile in accordance with the methods described in C. E. Kwartler et al., J. Am. Chem. Soc., 65, 1804 (1943), respectively. The results including the analytical values are shown in Tables 6 and 7.

TABLE 6

| Example No. | 3-Amino-chlorindazole | (g) | Product | Form | Yield (%) |
|---|---|---|---|---|---|
| 2 | 5-Cl-3-amino-indazole | 5.66 | 1-(3-diethylaminopropyl)-5-chloro-3-amino-indazole | Solid | 58 |
| 3 | 6-Cl-3-amino-indazole | 5.66 | 1-(3-diethylaminopropyl)-6-chloro-3-amino-indazole | Solid | 60 |
| 4 | 7-Cl-3-amino-indazole | 5.66 | 1-(3-diethylaminopropyl)-7-chloro-3-amino-indazole | Solid | 55 |

TABLE 7

| Example No. | IR Spectrum (cm$^{-1}$) | NMR Spectrum (δ, CDCl$_3$) | Mass Spectrum (m/e) | Elemental Analysis Value Calcd.(%) | Found(%) |
|---|---|---|---|---|---|
| 2 | 3320, 3210 | 0.97(t, 6H), 2.34(m, 4H) | 281, 283, 252 | $C_{14}H_{23}N_4Cl_3$ | |
|   | 2950, 2860 | 2.47(q, 4H), 4.21(t, 2H) | 223, 209, 195 | C 47.54; H 6.55 | C 47.48; H 6.51 |
|   | 1610, 1590 | 5.00(bs, 2H), 7.27(s, 2H) 7.69(s, 1H) |  | N 15.84; Cl 30.07 | N 15.99; Cl 30.02 |
| 3 | 3310, 3230 | 0.96(t, 6H), 2.34(m, 4H) | 281, 283, 252 | $C_{14}H_{23}N_4Cl_3$ | |
|   | 2940, 2850 | 2.48(q, 4H), 4.20(t, 2H) | 223, 209, 195 | C 47.54; H 6.55 | C 47.61; H 6.58 |
|   | 1615, 1590 | 5.30(bs, 2H), 6.87(d, 1H) 7.26(s, 1H), 7.67(d, 1H) |  | N 15.84; Cl 30.07 | N 15.68; Cl 30.13 |
| 4 | 3310, 3230 | 0.97(t, 6H), 2.33(m, 4H) | 281, 283, 252 | $C_{14}H_{23}N_4Cl_3$ | |
|   | 2950, 2850 | 2.47(q, 4H), 4.23(t, 2H) | 223, 209, 195 | C 47.54; H 6.55 | C 47.68; H 6.54 |

TABLE 7-continued

| Example No. | IR Spectrum (cm$^{-1}$) | NMR Spectrum (δ, CDCl$_3$) | Mass Spectrum (m/e) | Elemental Analysis Value Calcd.(%) | Found(%) |
| --- | --- | --- | --- | --- | --- |
| | 1615, 1580 | 5.28(bs, 2H), 7.00(d, 1H) 7.30(d, 1H), 7.63(d, 1H) | | N 15.84; Cl 30.07 | N 15.78; Cl 30.00 |

EXAMPLE 5

3-Aminoindazole was prepared in accordance with the method described in C. E. Kwartler et al., J. Am. Chem. Soc., 65, 1804 (1943).

To 50 ml of dioxane were added 5.0 g of 3-aminoindazole thus obtained and 6.68 g of phthalic anhydride, and the mixture was stirred for 5 hours at 120° C. After the mixture was condensed under reduced pressure, the condensed residue was added with 30 ml of diethyl ether and stirred under cooling with ice and water for 30 minutes to separate crystals. Then the crystals were obtained by filtration and dried under reduced pressure to give 8.6 g of 3-phthalimidoindazole having the following analytical values in a yield of 87%.

IR absorption spectrum ($\nu_{max}$, cm$^{-1}$): 3310, 1790, 1735 and 1625.

NMR spectrum [δ,(CD$_3$)$_2$SO]: 7.57(m, 8H) and 13.35(bs, 1H).

Mass spectrum (m/e): 263(M$^+$, 100), 238(M-27, 17), 219(M-44, 10), 207(M-56, 3), 192(M-71, 5) and 179(M-84, 5).

To 60 ml of anhydrous N,N-dimethylformamide were added 4.0 g of 3-phthalimidoindazole, 4.83 g of 3-bromo-propyldiethylamine hydrobromide as obtained in Referential Example 1 and 6.3 g of anhydrous potassium carbonate, and the mixture was stirred for 12 hours at 80° C. After cooling the mixture, the mixture was added with 80 ml of water and the reaction product was extracted with diethyl ether. The ether layer was extracted three times with 2N-hydrochloric acid. Then the hydrochloric acid layer was washed with diethyl ether and the pH of the layer was adjusted to 11 with potassium carbonate. The layer was extracted three times with chloroform. The chloroform layer was dried over anhydrous solidum sulfate and chloroform was removed under reduced pressure to give 3.33 g of 1-(3-diethylaminopropyl)-3-phthalimidoindazole having the following analytical values in a yield of 58%.

IR absorption spectrum ($\nu_{max}$, cm$^{-1}$): 3050, 2970, 1780, 1730 and 1615.

NMR spectrum [δ, CDCl$_3$]: 0.96(t, 6H), 2.34(m, 4H), 2.47(q, 4H), 4.25(t, 2H) and 7.18(m, 8H).

Mass spectrum (m/e): 375(M$^+$), 291(M-84), 277(M-98) and 263(M-112).

To 70 ml of ethyl alcohol was added 3.30 g of 1-(3-diethylaminopropyl)-3-phthalimidoindazole. The mixture was added with 2.50 g of 85% hydrazine hydrate under cooling with ice and stirred for 3 hours under cooling with ice. The reaction mixture was filtered and the filtrate was condensed under reduced pressure. The condensed residue was added with 20 ml of water and the reaction product was extracted with chloroform. The chloroform layer was extracted with 2N-hydrochloric acid and the pH of the hydrochloric acid layer was adjusted to 10 with potassium carbonate. The alkali layer was extracted with chloroform. The chloroform layer was dried over anhydrous sodium sulfate, and chloroform was removed under reduced pressure to give 1.78 g of 1-(3-diethylaminopropyl)-3-aminoindazole having the following analytical values in a yield of 85%.

IR absorption spectrum ($\nu_{max}$, cm$^{-1}$): 3320, 3220, 2930, 2850, 1615 and 1580.

NMR spectrum [δ, CDCl$_3$]: 0.97(t, 6H), 2.34(bm, 4H), 2.47(q, 4H), 4.25(t, 2H), 5.00(bs, 2H) and 7.11(m, 4H).

Mass spectrum (m/e): 246(M$^+$), 217(M-29), 188(M-58), 174(M-72) and 160(M-86).

1-(3-Diethylaminopropyl)-3,5-diaminoindazole was prepared by the following method with reference to R. Adam et al., "Laboratory Experiments in Organic Chemistry" 4th ed., PP. 299, 301 and 303, Macmillan, New York, 1949 and S. E. Hazlet and C. A. Dornfeld, J. Am. Chem. Soc. 75 4334 (1935).

In 2.58 ml of sulfuric acid was dissolved 1.5 g of 1-(3-diethylaminopropyl)-3-aminoindazole, and to the solution were added dropwise 0.41 ml of nitric acid (d-1.42) and 0.41 ml of sulfuric acid (sp.gr. 1.84) under cooling with ice. The solution was stirred for 2 hours at 5°-10° C. and then added to 12.1 ml of ice and water. The pH of the solution was adjusted to at least 11 with aqueous ammonia solution and the solution was extracted with chloroform. The chloroform layer was dried with anhydrous sodium sulfate and chloroform was removed under reduced pressure. In 50 ml of anhydrous benzene was dissolved the residue obtained. To the solution were added 10 g of iron powder and 2 ml of hydrochloric acid, and the solution was stirred for 30 minutes at 80° C. The solution was further added with 0.5 ml of water and stirred for 10 hours at 80° C. After cooling the solution, the solution was filtered and the benzene layer obtained as the filtrate was extracted three times with 20 ml of 1N-hydrochloric acid. The pH of the hydrochloric acid layer was adjusted to at least 11 with potassium carbonate, and the alkali layer was extracted with chloroform. The chloroform layer was dried with anhydrous sodium sulfate, and chloroform was removed under reduced pressure. The residue thus obtained was subjected to an alumina-column chromatography (alumina: 100 g) using chloroform as the developing solvent to give 0.65 g of 1-(3-diethylaminopropyl)-3,5-diaminoindazole having the following analytical values in a yield of 41%.

IR absorption spectrum ($\nu_{max}$, cm$^{-1}$): 3320, 3220, 2940, 2880, 1620 and 1590.

NMR spectrum [δ, CD$_3$OD]: 0.97(t, 6H), 2.33(m, 4H), 2.48(q. 4H), 4.23(t, 2H) and 7.30(m, 3H).

Mass spectrum (m/e): 261(M$^+$), 232(M-29), 203(M-58), 189(M-72) and 175(M-86).

In 15 ml of absolute ethyl alcohol was dissolved 0.6 g of 1-(3-diethylaminopropyl)-3,5-diaminoindazole, and into the solution was introduced dried hydrogen chloride gas under cooling with ice. To the solution was added anhydrous diethyl ether to separate crystals. Then the crystals were obtained by filtration and dried to give 1-(3-diethylaminopropyl)-3,5-diaminoindazole trihydrochloride having the following analytical value.

Elemental Analysis Value: $C_{14}H_{26}N_5Cl_3$: Calcd.(%): C 45.35; H 7.07; N 18.89; Cl 28.69. Found (%): C 45.41; H 7.10; N 18.68; Cl 28.81.

described in C. E. Kwartler et al., J. Am. Chem. Soc., 65 1804 (1943). The results including the analytical values are shown in Tables 8 and 9.

TABLE 8

| Example No. | 3-Aminoindazole | (g) | Product | Form | Yield (%) |
|---|---|---|---|---|---|
| 6 | 5-methoxy-3-aminoindazole | 5.51 | 5-methoxy-1-(3-diethylaminopropyl)-3-aminoindazole | Solid | 57 |
| 7 | 5-methyl-3-aminoindazole | 4.97 | 5-methyl-1-(3-diethylaminopropyl)-3-aminoindazole | Solid | 55 |

TABLE 9

| Example No. | IR Spectrum (cm$^{-1}$) | NMR Spectrum (δ, CDCl$_3$) | Mass Spectrum (m/e) | Elemental Analysis Value Calcd.(%) | Elemental Analysis Value Found(%) |
|---|---|---|---|---|---|
| 6 | 3330, 3200 2950, 2890 1620, 1580 | 0.97(t, 6H), 2.35(m, 4H) 2.47(q, 4H), 3.80(s, 3H) 4.20(t, 2H), 5.20(bs, 2H) 7.13(m, 3H) | 276(M$^+$), 247 218, 204, 190 | $C_{15}H_{26}ON_4Cl_2$ C 51.58; H 7.50 N 16.04; Cl 20.30 | C 51.61; H 7.48 N 15.98; Cl 20.34 |
| 7 | 3310, 3210 2960, 2880 1630, 1580 | 0.95(t, 6H), 2.33(s, 3H) 2.36(m, 4H), 2.47(q, 4H) 4.21(t, 2H), 5.20(bs, 2H) 7.08(s, 2H), 7.41(s, 1H) | 260(M$^+$), 231 202, 188, 174 | $C_{15}H_{26}N_4Cl_2$ C 54.05; H 7.86 N 16.81; Cl 21.28 | C 53.98; H 7.81 N 16.98; Cl 21.23 |

EXAMPLE 6 and 7

The same procedures as described in Example 1 were repeated except that 3-amino-5-methoxyindazole and 3-amino-5-methylindazole as set forth in Table 8 were employed, respectively, instead of the 5.66 g of 3-amino-4-chloroindazole. The 3-amino-5-methoxyindazole was prepared in accordance with the method described in Ger. Offen. No. 25 27 288 (Cl, C09B), and the 3-amino-5-methylindazole was prepared from 5-methylanthranilonitrile in accordance with the method

EXAMPLES 8-22

The same procedures as described in Example 1 were repeated except that the 3-amino-5-chloroindazole as prepared in Example 2 and ω-halogenoalkylamine hydrobromides as set forth in Table 10 were employed instead of the 5.66 g of 3-amino-4-chloroindazole and the 4.83 g of 3-bromopropyldiethylamine hydrobromide. The results including the analytical values are shown in Tables 10 and 11.

TABLE 10

| Example No. | ω-Halogenoalkylamine Hydrobromide | (g) | Product | Form | Yield (%) |
|---|---|---|---|---|---|
| 8 | $(C_4H_9)_2N-(CH_2)_3Br \cdot HBr$ | 5.76 | 5-chloro-1-(3-dibutylaminopropyl)-3-aminoindazole | Solid | 61 |
| 9 | $(CH_3)_2N-CH(CH_3)CH_2CH_2Br \cdot HBr$ | 4.55 | 5-chloro-1-[3-(dimethylamino)butyl]-3-aminoindazole | Solid | 55 |

TABLE 10-continued
| Example No. | ω-Halogenoalkylamine Hydrobromide | (g) | Product | Form | Yield (%) |
|---|---|---|---|---|---|
| 10 | 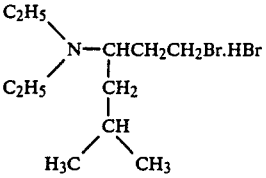 | 5.77 | 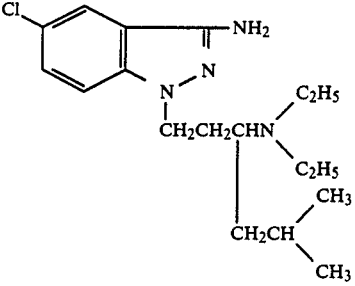 | Solid | 51 |
| 11 | 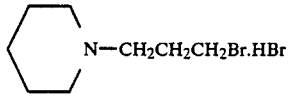 | 5.00 | 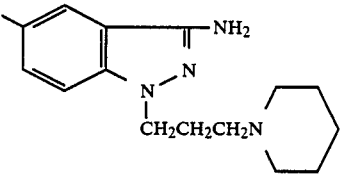 | Solid | 49 |
| 12 | 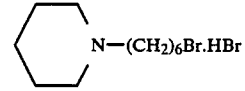 | 5.74 | 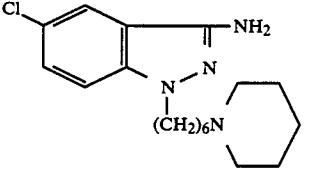 | Solid | 63 |
| 13 | 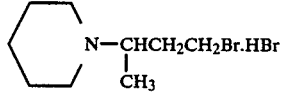 | 5.24 | 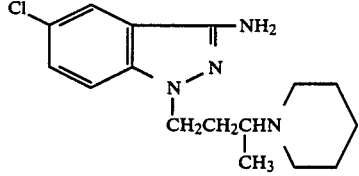 | Solid | 58 |
| 14 | 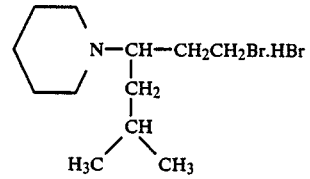 | 5.98 | 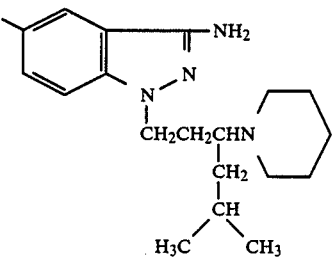 | Solid | 53 |
| 15 | 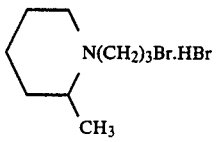 | 5.24 | 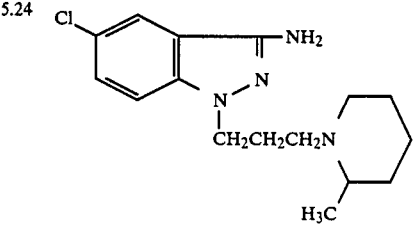 | Solid | 55 |

TABLE 10-continued

| Example No. | ω-Halogenoalkylamine Hydrobromide | (g) | Product | Form | Yield (%) |
|---|---|---|---|---|---|
| 16 | 2,6-dimethylpiperidine-N—(CH$_2$)$_3$Br·HBr | 5.52 | 5-chloro-1-[3-(2,6-dimethylpiperidin-1-yl)propyl]-1H-indazol-3-amine | Solid | 60 |
| 17 | 4-hydroxypiperidine-N—(CH$_2$)$_3$Br·HBr | 5.30 | 5-chloro-1-[3-(4-hydroxypiperidin-1-yl)propyl]-1H-indazol-3-amine | Solid | 59 |
| 18 | 4-chloropiperidine-N—(CH$_2$)$_3$Br·HBr | 5.63 | 5-chloro-1-[3-(4-chloropiperidin-1-yl)propyl]-1H-indazol-3-amine | Solid | 60 |
| 19 | hexamethyleneimine-N—(CH$_2$)$_3$Br·HBr | 5.27 | 5-chloro-1-[3-(hexamethyleneimin-1-yl)propyl]-1H-indazol-3-amine | Solid | 58 |
| 20 | CH$_3$—N(piperazine)N—(CH$_2$)$_3$Br·HBr | 4.98 | 5-chloro-1-[3-(4-methylpiperazin-1-yl)propyl]-1H-indazol-3-amine | Solid | 59 |
| 21 | pyrrolidine-N—(CH$_2$)$_3$Br·HBr | 4.78 | 5-chloro-1-[3-(pyrrolidin-1-yl)propyl]-1H-indazol-3-amine | Solid | 53 |
| 22 | morpholine-N—(CH$_2$)$_3$Br·HBr | 5.03 | 5-chloro-1-[3-(morpholin-4-yl)propyl]-1H-indazol-3-amine | Solid | 57 |

TABLE 11

| Example No. | IR Spectrum (cm$^{-1}$) | NMR Spectrum (δ, CDCl$_3$) | Mass Spectrum (m/e) | Elemental Analysis Value Calcd.(%) | Found(%) |
|---|---|---|---|---|---|
| 8 | 3310, 3220<br>3010, 2960<br>1640, 1605<br>1580 | 0.92(m, 6H), 1.28(m, 10H)<br>2.30(m, 6H), 4.20(t, 2H)<br>4.51(bs, 2H), 7.28(s, 2H)<br>7.70(s, 1H) | 337(M$^+$), 339<br>280, 223, 209 | C$_{18}$H$_{31}$N$_4$Cl$_3$<br>C 52.75; H 7.63<br>N 13.67; Cl 25.95 | C 53.01; H 7.65<br>N 13.40; Cl 25.94 |
| 9 | 3320, 3150<br>2975, 1610<br>1585 | 0.87(d, 3H), 1.34(m, 2H)<br>2.24(s, 6H), 2.34(m, 1H)<br>4.20(t, 2H), 5.10(bs, 2H)<br>7.27(s, 2H), 7.68(s, 1H) | 267(M$^+$), 269<br>252, 237, 222 | C$_{13}$H$_{21}$N$_4$Cl$_3$<br>C 45.97; H 6.23<br>N 16.49; Cl 31.31 | C 46.03; H 6.27<br>N 16.31; Cl 31.39 |
| 10 | 3310, 3150<br>2980, 1610<br>1590 | 0.95(m, 12H), 1.35(m, 5H)<br>2.59(m, 5H), 4.20(t, 2H)<br>5.09(bs, 2H), 7.26(s, 2H)<br>7.68(s, 1H) | 337(M$^+$), 339<br>280, 208, 195 | C$_{18}$H$_{31}$N$_4$Cl$_3$<br>C 52.75; H 7.62<br>N 13.67; Cl 25.96 | C 52.78; H 7.71<br>N 13.53; Cl 25.98 |
| 11 | 3320, 3200<br>2950, 1650<br>1605 | 1.43(m, 6H), 2.17(m, 8H)<br>4.25(t, 2H), 5.02(bs, 2H)<br>7.28(s, 2H), 7.67(s, 1H) | 293(M$^+$), 295<br>208, 195, 181 | C$_{15}$H$_{23}$N$_4$Cl$_3$<br>C 49.26; H 6.34<br>N 15.32; C 29.08 | C 49.33; H 6.38<br>N 15.27; C 29.02 |
| 12 | 3320, 3200<br>2950, 1650<br>1610 | 1.38(m, 14H), 2.27(m, 6H)<br>4.10(t, 2H), 4.50(bs, 2H)<br>7.26(s, 2H), 7.68(s, 1H) | 335(M$^+$), 337<br>251, 237, 223 | C$_{18}$H$_{29}$N$_4$Cl$_3$<br>C 53.01; H 7.17<br>N 13.74; Cl 26.08 | C 52.93; H 7.08<br>N 13.91; Cl 26.08 |
| 13 | 3300, 3170<br>2950, 1630<br>1600, 1570 | 0.85(d, 3H), 1.41(m, 8H)<br>2.30(m, 5H), 4.20(t, 2H)<br>4.70(bs, 2H), 7.28(s, 2H)<br>7.68(s, 1H) | 307(M$^+$), 309<br>292, 208, 195 | C$_{16}$H$_{25}$N$_4$Cl$_3$<br>C 50.61; H 6.64<br>N 14.75; Cl 28.00 | C 50.72; H 6.65<br>N 14.48; Cl 28.15 |
| 14 | 3300, 3170<br>2970, 1625<br>1600, 1560 | 0.90(t, 6H), 1.34(m, 11H)<br>2.47(bs, 6H), 4.20(t, 2H)<br>4.75(bs, 2H), 7.27(s, 2H)<br>7.68(s, 1H) | 349(M$^+$), 351<br>292, 208, 195 | C$_{19}$H$_{31}$N$_4$Cl$_3$<br>C 54.10; H 7.41<br>N 13.28; Cl 25.21 | C 53.97; H 7.39<br>N 13.51; Cl 25.13 |
| 15 | 3320, 3210<br>2940, 2870<br>1615, 1580 | 0.91(d, 3H), 1.50(m, 6H)<br>2.32(m, 7H), 4.00(bs, 2H)<br>4.11(t, 2H), 7.28(s, 2H)<br>7.68(s, 1H) | 307(M$^+$), 309<br>293, 211, 196 | C$_{16}$H$_{25}$N$_4$Cl$_3$<br>C 50.60; H 6.64<br>N 14.75; Cl 28.01 | C 50.48; H 6.51<br>N 15.01; Cl 28.00 |
| 16 | 3310, 3220<br>2940, 2870<br>1630, 1605 | 1.19(d, 6H), 1.39(m, 6H)<br>2.30(m, 2H), 2.80(m, 2H)<br>3.75(t, 2H), 4.20(t, 2H)<br>4.90(bs, 2H), 7.25(s, 2H)<br>7.68(s, 1H) | 321(M$^+$), 323<br>306, 209, 195 | C$_{17}$H$_{27}$N$_4$Cl$_3$<br>C 51.85; H 6.91<br>N 14.23; Cl 27.01 | C 52.01; H 7.01<br>N 14.02; Cl 26.96 |
| 17 | 3400, 3300<br>2960, 1625<br>1570 | 1.48(bs, 4H), 2.08(m, 3H)<br>2.89(m, 6H), 4.23(t, 2H)<br>4.49(bs, 2H), 7.26(s, 2H)<br>7.70(s, 1H) | 310(M$^+$), 312<br>293, 209, 195 | C$_{15}$H$_{23}$ON$_4$Cl$_3$<br>C 47.20; H 6.07<br>N 14.68; Cl 27.86 | C 47.21; H 6.11<br>N 14.64; Cl 27.78 |
| 18 | 3345, 3260<br>2950, 2870<br>1625, 1600 | 1.45(bs, 4H), 2.09(m, 3H)<br>2.89(m, 6H), 4.23(t, 2H)<br>4.47(bs, 2H), 7.26(s, 2H)<br>7.68(s, 1H) | 327(M$^+$), 292<br>209, 195, 181 | C$_{15}$H$_{22}$N$_4$Cl$_4$<br>C 45.02; H 5.54<br>N 14.00; Cl 35.44 | C 45.06; H 5.48<br>N 13.91; Cl 35.55 |
| 19 | 3320, 3160<br>2950, 1640<br>1610 | 1.52(bs, 8H), 2.10(bs, 2H)<br>2.47(bs, 6H), 4.20(t, 2H)<br>4.69(bs, 2H), 7.26(s, 2H)<br>7.69(s, 1H) | 307(M$^+$), 309<br>209, 195, 181 | C$_{16}$H$_{25}$N$_4$Cl$_3$<br>C 50.60; H 6.64<br>N 14.75; Cl 28.01 | C 50.68; H 6.69<br>N 14.47; Cl 28.16 |
| 20 | 3320, 3210<br>2940, 2800<br>1645, 1605 | 2.32(m, 15H), 4.15(t, 2H)<br>4.68(bs, 2H), 7.28(s, 2H)<br>7.68(s, 1H) | 308(M$^+$), 310<br>293, 278, 222 | C$_{15}$H$_{25}$N$_5$Cl$_4$<br>C 43.18; H 6.04<br>N 16.79; Cl 33.99 | C 43.21; H 5.91<br>N 16.85; Cl 34.03 |
| 21 | 3315, 3180<br>2930, 1650<br>1600 | 1.69(bm, 6H), 2.48(bm, 6H)<br>4.24(t, 2H), 4.70(bs, 2H)<br>7.28(s, 2H), 7.70(s, 1H) | 278, 280, 208<br>194, 180 | C$_{14}$H$_{21}$N$_4$Cl$_3$<br>C 47.81; H 6.02<br>N 15.93; Cl 30.24 | C 47.84; H 6.05<br>N 15.90; Cl 30.21 |
| 22 | 3400, 3170<br>2980, 1620<br>1605 | 1.60(m, 2H), 2.45(m, 6H)<br>3.56(t, 4H), 4.23(t, 2H)<br>4.71(bs, 2H), 7.29(s, 2H)<br>7.69(s, 1H) | 295(M$^+$), 297<br>209, 195, 181 | C$_{14}$H$_{21}$ON$_4$Cl$_3$<br>C 45.73; H 5.76<br>N 15.24; Cl 28.92 | C 45.75; H 5.77<br>N 15.19; Cl 28.99 |

EXAMPLE 23

To 20 ml of diethyl ether solution containing 600 mg of magnesium powder was added dropwise a mixed solution consisting of 2.81 g of 1-(3-diethylaminopropyl)-3-amino-4-chloroindazole obtained by the same method as described in Example 1, 2.06 g of iso-propyl bromide and 20 ml of diethyl ether. Into the solution were introduced dried oxygen gas and dried carbon dioxide gas for 10 hours so as to reflux the solution, and the solution was left to stand for 12 hours. The pH of the solution was adjusted to 4.0 by adding dropwise sulfuric acid to the solution at 0° C. The solution was added with 50 ml of water and filtered. To the aqueous layer of the filtrate was added an aqueous potassium carbonate solution to separate crystals. The crystals were obtained by filtration and dried to give 1.01 g of 1-(3-diethylaminopropyl)-3-amino-4-hydroxyindazole having the following analytical values in a yield of 40%.

IR absorption spectrum ($\nu_{max}$, cm$^{-1}$): 3590, 3330, 2970, 1610 and 1580.

NMR spectrum [δ, CD$_3$OD]: 0.97(t, 6H), 2.34(m, 4H), 2.49(q, 4H), 4.21(t, 2H) and 7.19(m, 3H).

Mass spectrum (m/e): 263(M$^+$), 234(M-29), 205(m-58), 191(M-72) and 177(M-86).

In 50 ml of absolute ethyl alcohol was dissolved 3.0 g of 1-(3-diethylaminopropyl)-3-amino-4-hydroxyindazole, and into the solution was introduced dried hydrogen chloride gas under cooling with ice. To the solution was added anhydrous diethyl ether to separate crystals. Then the crystals were obtained by filtration and dried to give 1-(3-diethylaminopropyl)-3-amino-4-hydroxyindazole dihydrochloride having the following analytical value.

Elemental Analysis Value: $C_{14}H_{24}ON_4Cl_2$: Calcd.(%): C 50.15; H 7.22; N 16.71; Cl 21.15. Found (%): C 50.21; H 7.19; N 16.83; Cl 21.19.

EXAMPLE 24

To 9.25 g of 1-(3-diethylaminopropyl)-3-aminoindazole obtained by the same method as described in Example 5 was added 4.3 g of 95% sulfuric acid, and the mixture was stirred for 3 hours at 80° C. To the mixture was added 13 ml of water, and the pH of the mixture was adjusted to 14 with potassium hydroxide. Then the mixture was washed twice with 20 ml of chloroform, and water was removed under reduced pressure. The residue was added with 12.5 g of potassium hydroxide and 0.6 ml of water, and stirred for 8 hours at 250° C.

After the mixture was cooled, to the mixture was added hydrochloric acid to separate crystals. The crystals were filtered and dried to give 4.50 g of 1-(3-diethylaminopropyl)-3-amino-5-hydroxyindazole having the following analytical values in a yield of 41%.

IR absorption spectrum ($\nu_{max}$, cm$^{-1}$): 3610, 3350, 3020, 2980, 1615 and 1580.

NMR spectrum [$\delta$,CD$_3$OD]: 0.96(t, 6H), 2.35(m, 4H), 2.48(q. 4H), 4.21(t, 2H) and 7.13(m, 3H).

Mass spectrum (m/e): 263(M$^+$), 164(M-98), 150(M-112) and 136(M-126).

In 50 ml of absolute ethyl alcohol was dissolved 4.0 g of 1-(3-diethylaminopropyl)-3-amino-5-hydroxyindazole, and into the solution was introduced dried hydrogen chloride gas under cooling with ice. To the solution was added anhydrous diethyl ether to separate crystals. Then the crystals were obtained by filtration and dried to give 1-(3-diethylaminopropyl)- 3-amino-5-hydroxyindazole dihydrochloride having the following analytical value.

Elemental Analysis Value: $C_{14}H_{24}ON_4Cl_2$: Calcd.(%): C 50.15; H 7.22; N 16.71; Cl 21.15. Found (%): C 50.21; H 7.23; N 16.68; Cl 21.02.

EXAMPLES 25 and 26

1-(3-Diethylaminopropyl)-3-amino-6-chloroindazole and 1-(3-diethylaminopropyl)-3-amino-7-chloroindazole were prepared by the same method as described in Example 1 except that 3-amino-6-chloroindazole and 3-amino-7-chloroindazole were employed, respectively, instead of the 5.66 g of 3-amino-4-chloroindazole.

The same procedures as described in Example 23 were repeated except that 1-(3-diethylaminopropyl)-3-amino-6-chloroindazole and 1-(3-diethylaminopropyl)-amino-7-chloroindazole were employed, respectively, instead of the 1-(3-diethylaminopropyl)-3-amino-4-chloroindazole. The results including the analytical values are shown in Tables 12 and 13.

TABLE 12

| Example No. | 3-Amino-chloroindazole | (g) | Product | Form | Yield (%) |
|---|---|---|---|---|---|
| 25 | [structure: 5-chloro-3-amino-indazole] | 5.66 | [structure: 1-(3-diethylaminopropyl)-3-amino-5-hydroxyindazole] | Solid | 50 |
| 26 | [structure: 7-chloro-3-amino-indazole] | 5.66 | [structure: 1-(3-diethylaminopropyl)-3-amino-7-hydroxyindazole] | Solid | 40 |

TABLE 13

| Example No. | IR Spectrum (cm$^{-1}$) | NMR Spectrum ($\delta$, CD$_3$OD) | Mass Spectrum (m/e) | Elemental Analysis Value Calcd.(%) | Found(%) |
|---|---|---|---|---|---|
| 25 | 3590, 3310 | 0.98(t, 6H), 2.35(m, 4H) | 263(M$^+$), 234 | $C_{14}H_{24}ON_4Cl_2$ | |
| | 2970, 1610 1570 | 2.48(q, 4H), 4.19(t, 2H) 7.21(m, 3H) | 205, 191, 177 | C 50.15; H 7.22 N 16.71; Cl 21.15 | C 50.14; H 7.19 N 16.82; Cl 20.92 |
| 26 | 3600, 3320 | 0.97(t, 6H), 2.34(m, 4H) | 263(M$^+$), 234 | $C_{14}H_{24}ON_4Cl_2$ | |
| | 2980, 1615 1580 | 2.49(q, 4H), 4.20(t, 2H) 7.20(m, 3H) | 205, 191, 177 | C 50.15; H 7.22 N 16.71; Cl 21.15 | C 50.21; H 7.28 N 16.68; Cl 20.06 |

EXAMPLE 27

The same procedures as described in Example 1 were repeated except that 3-amino-5-iodoindazole was employed instead of the 3-amino-4-chloroindazole. 1-(33-amino-5-iodoindazole having the following analytical values was obtained in a yield of 85%.

IR absorption spectrum ($\nu_{max}$, cm$^{-1}$): 3320, 3210, 2940, 2860, 1615 and 1580.

NMR spectrum [$\delta$,CDCl$_3$]: 0.98(t, 6H), 2.34(m, 4H), 2.48(q, 4H), 4.2l(t, 2H), 5.0l(bs,2H), 7.01(d, 1H), 7.33(d, 1H) and 7.69(d, 1H).

Mass spectrum (m/e): 373(M+), 301(M-72), 273(M-102), 259(M-114) and 239(M-134).

In 15 ml of absolute ethyl alcohol was dissolved 1.50 g of 1-(3-diethylaminopropyl)-3-amino-5-iodoindazole, and into the solution was introduced dried hydrogen chloride gas under cooling with ice. To the solution was added anhydrous diethyl ether to separate crystals. Then the crystals were obtained by filtration and dried to give 1-(3-diethylaminopropyl)-3-amino-5-iodoindazole dihydrochloride having the following analytical value.

Elemental Analysis Value: $C_{14}H_{23}N_4Cl_2$: Calcd.(%): C 37.77; H 5.21; N 12.59; I 28.51; Cl 15.92. Found (%): C 37.53; H 5.19; N 12.71; I 28.68; Cl 15.89.

EXAMPLE 28

The same procedures as described in Example 27 were repeated except that 3-amino-7-iodoindazole was employed instead of the 3-amino-5-iodoindazole. 1-(3-Diethylaminoproyl)-3-amino-5-iodoindazole having the following analytical values was obtained in a yield of 51%.

IR absorption spectrum ($\nu_{max}$, cm$^{-1}$): 3310, 3210, 2950, 2870, 1610 and 1570.

NMR spectrum [δ,CDCl$_3$]: 0.99(t, 6H), 2.33(m, 4H), 2.49(q, 4H), 5.20(bs,2H), 7.01(d, 1H), 7.32(d, 1H) and 7.69(d, 1H).

Mass spectrum (m/e): 373(M+), 301(M-72), 273(M-102), 259(M-114) and 239(M-134).

In 50 ml of absolute ethyl alcohol was dissolved 4.0 g of 1-(3-diethylaminopropyl)-3-amino-7-iodoindazole, and into the solution was introduced dried hydrogen chloride gas under cooling with ice. To the solution was added anhydrous diethyl ether to separate crystals. Then the crystals were obtained by filtration and dried to give 1-(3-diethylaminopropyl)-3-amino-7-iodoindazole dihydrochloride having the following analytical value.

Elemental Analysis Value: $C_{14}H_{23}N_4ICl_2$: Calcd.(%): C 37.77; H 5.21; N 12.59; I 28.51; Cl 15.92. Found (%): C 37.61; H 5.15; N 12.73; I 28.70; Cl 15.81.

EXAMPLE 29

In 30 ml of sulfuric acid was dissolved 40 g of 1-(3-diethylaminopropyl)-3-aminoindazole obtained by the same method as described in Example 5. To the solution were added dropwise 10.2 ml of nitric acid and 10.2 ml of sulfuric acid at 0° C. After stirring the solution for 1 hour, the pH of the solution was adjusted to 10.4 with an aqueous ammonia solution. Then the solution was extracted three times with 50 ml of chloroform. The chloroform layer was washed with water and dried over anhydrous sodium sulfate, and chloroform was removed under reduced pressure. The residue thus obtained was subjected to an alumina-column chromatography(alumina: 200 g) using chloroform as the developing solvent to give 10.56 g of 1-(3-diethylaminopropyl)-3-amino-5,7-dinitroindazole having the following analytical values in a yield of 21%.

IR absorption spectrum ($\nu_{max}$, cm$^{-1}$): 3460, 3350, 3680, 1610 and 1520.

NMR spectrum [δ,d$_6$-DMSO]: 0.97(t, 6H), 2.34(m, 4H), 2.46(q, 4H), 4.23(t, 2H), 7.88(s, 1H) and 8.68(s, 1H).

Mass spectrum (m/e): 337(M+), 291(M-46) 245(M-92) and 229(M-108).

A mixture consisting of 9.0 g of 1-(3-diethylaminopropyl)-3-amino-5,7-dinitroindazole, 18 g of iron powder, 60 ml of methyl alcohol, 30 ml of water and 3 ml of hydrochloric acid was stirred for 1.5 hours at 70° C. After the reaction mixture was cooled, the mixture was filtered. The pH of the filtrate was adjusted to 11 with an aqueous potassium carbonate solution and the filtrate was extracted three times with 50 ml of ethyl acetate. The ethyl acetate layer was washed with water and dried over anhydrous sodium sulfate, and ethyl acetate was removed under reduced pressure. The residue thus obtained was subjected to an alumina-column chromatography(alumina: 200 g) using chloroform as the developing solvent to give 1.78 g of 1-(3-diethylaminopropyl)-3,5,7-triaminoindazole having the following analytical values in a yield of 23%.

IR absorption spectrum ($\nu_{max}$, cm$^{-1}$): 3480, 3320, 3180, 1640 and 1590.

NMR spectrum [δ,CD$_3$OD]: 0.97(t, 6H), 2.30(m, 4H), 2.46(q, 4H), 4.25(t, 2H) and 6.88(m, 2H).

Mass spectrum (m/e): 277(M+), 261(M-16), 245(M-32) and 229(M-48).

In 20 ml of absolute ethyl alcohol was dissolved 2.0 g of 1-(3-diethylaminopropyl)-3,5,7-triaminoindazole and into the solution was introduced dried hydrogen chloride gas under cooling with ice. To the solution was added anhydrous diethyl ether to separate crystals. Then the crystals were obtained by filtration and dried to give 1-(3-diethylaminopropyl)-3,5,7-triaminoindazole tetrahydrochloride having the following analytical value.

Elemental Analysis Value: $C_{14}H_{28}N_6Cl_4$: Calcd.(%): C 39.83; H 6.68; N 19.90; Cl 33.59. Found (%): C 39.79; H 6.51; N 20.10; Cl 33.60.

EXAMPLES 30-44

The same procedures as described in Example 24 were repeated except that ω-halogenoalkylamine hydrobromides as set forth in Table 14 were employed instead of the 4.83 g of 3-bromopropyldiethylamine hydrobromide. The results including the analytical values are shown in Tables 14 and 15.

TABLE 14

| Example No. | ω-Halogenoalkylamine Hydrobromide | (g) | Product | Form | Yield (%) |
|---|---|---|---|---|---|
| 30 | C$_4$H$_9$\N—(CH$_2$)$_3$Br·HBr / C$_4$H$_9$ | 5.76 | 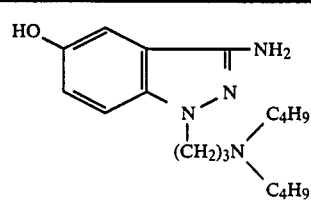 | Solid | 60 |

TABLE 14-continued

| Example No. | ω-Halogenoalkylamine Hydrobromide | (g) | Product | Form | Yield (%) |
|---|---|---|---|---|---|
| 31 | (CH$_3$)$_2$N—CH(CH$_3$)CH$_2$CH$_2$Br·HBr | 4.55 | 5-HO-1-[CH$_2$CH$_2$CH(CH$_3$)N(CH$_3$)$_2$]-3-amino-1H-indazole | Solid | 54 |
| 32 | (C$_2$H$_5$)$_2$N—CH(CH$_2$CH(CH$_3$)$_2$)CH$_2$CH$_2$Br·HBr | 5.77 | 5-HO-1-[CH$_2$CH$_2$CH(CH$_2$CH(CH$_3$)$_2$)N(C$_2$H$_5$)$_2$]-3-amino-1H-indazole | Solid | 50 |
| 33 | piperidino-CH$_2$CH$_2$CH$_2$Br·HBr | 5.00 | 5-HO-1-(CH$_2$CH$_2$CH$_2$-piperidino)-3-amino-1H-indazole | Solid | 48 |
| 34 | piperidino-(CH$_2$)$_6$Br·HBr | 5.74 | 5-HO-1-[(CH$_2$)$_6$-piperidino]-3-amino-1H-indazole | Solid | 62 |
| 35 | piperidino-CH(CH$_3$)CH$_2$CH$_2$Br·HBr | 5.24 | 5-HO-1-[CH$_2$CH$_2$CH(CH$_3$)-piperidino]-3-amino-1H-indazole | Solid | 57 |
| 36 | piperidino-CH(CH$_2$CH(CH$_3$)$_2$)CH$_2$CH$_2$Br·HBr | 5.98 | 5-HO-1-[CH$_2$CH$_2$CH(CH$_2$CH(CH$_3$)$_2$)-piperidino]-3-amino-1H-indazole | Solid | 52 |
| 37 | (2-methylpiperidino)-(CH$_2$)$_3$Br·HBr | 5.24 | 5-HO-1-[CH$_2$CH$_2$CH$_2$-(2-methylpiperidino)]-3-amino-1H-indazole | Solid | 54 |

TABLE 14-continued

| Example No. | ω-Halogenoalkylamine Hydrobromide | (g) | Product | Form | Yield (%) |
|---|---|---|---|---|---|
| 38 | 2,6-dimethylpiperidine-N—(CH$_2$)$_3$Br·HBr | 5.52 | 5-hydroxy-3-amino-1-[3-(2,6-dimethylpiperidin-1-yl)propyl]-1H-indazole | Solid | 59 |
| 39 | 4-hydroxypiperidine-N—(CH$_2$)$_3$Br·HBr | 5.30 | 5-hydroxy-3-amino-1-[3-(4-hydroxypiperidin-1-yl)propyl]-1H-indazole | Solid | 58 |
| 40 | 4-chloropiperidine-N—(CH$_2$)$_3$Br·HBr | 5.63 | 5-hydroxy-3-amino-1-[3-(4-chloropiperidin-1-yl)propyl]-1H-indazole | Solid | 59 |
| 41 | hexamethyleneimine-N—(CH$_2$)$_3$Br·HBr | 5.27 | 5-hydroxy-3-amino-1-[3-(hexamethyleneimin-1-yl)propyl]-1H-indazole | Solid | 57 |
| 42 | CH$_3$—N(piperazine)N—(CH$_2$)$_3$Br·HBr | 4.98 | 5-hydroxy-3-amino-1-[3-(4-methylpiperazin-1-yl)propyl]-1H-indazole | Solid | 58 |
| 43 | pyrrolidine-N—(CH$_2$)$_3$Br·HBr | 4.27 | 5-hydroxy-3-amino-1-[3-(pyrrolidin-1-yl)propyl]-1H-indazole | Solid | 49 |
| 44 | morpholine-N—(CH$_2$)$_3$Br·HBr | 5.03 | 5-hydroxy-3-amino-1-[3-(morpholin-4-yl)propyl]-1H-indazole | Solid | 56 |

TABLE 15

| Example No. | IR Spectrum (cm$^{-1}$) | NMR Spectrum (δ, CD$_3$OD) | Mass Spectrum (m/e) | Elemental Analysis Value Calcd.(%) | Found(%) |
|---|---|---|---|---|---|
| 30 | 3600, 3305 | 0.92(m, 6H), 1.27(m, 10H) | 319, 262, 205 | C$_{18}$H$_{32}$ON$_4$Cl$_2$ | |
| | 3210, 3050 | 2.31(m, 6H), 4.21(t, 2H) | 191 | C 55.24; H 8.24 | C 55.17; H 8.19 |
| | 2960, 1640 | 7.20(m, 3H) | | N 14.32; Cl 18.12 | N 14.44; Cl 18.31 |
| | 1605, 1580 | | | | |
| 31 | 3590, 3320 | 0.87(d, 3H), 1.33(m, 2H) | 249, 234, 219 | C$_{13}$H$_{22}$ON$_4$Cl$_2$ | |
| | 3140, 2970 | 2.24(s, 6H), 2.32(m, 1H) | 204 | C 48.61; H 6.90 | C 48.52; H 6.82 |
| | 1610, 1580 | 4.20(t, 2H), 7.22(m, 3H) | | N 17.44; Cl 22.07 | N 17.52; Cl 22.15 |
| 32 | 3610, 3310 | 0.96(m, 12H), 1.36(m, 5H) | 319, 262, 190 | C$_{18}$H$_{32}$ON$_4$Cl$_2$ | |
| | 3150, 2980 | 2.58(m, 5H), 4.21(t, 2H) | 177 | C 55.24; H 8.24 | C 55.31; H 8.20 |
| | 1610, 1570 | 7.21(m, 3H) | | N 14.31; Cl 18.12 | N 14.28; Cl 18.09 |
| 33 | 3600, 3320 | 1.42(m, 6H), 2.18(m, 8H) | 275, 190, 177 | C$_{15}$H$_{24}$ON$_4$Cl$_2$ | |
| | 3190, 2940 | 4.19(t, 2H), 7.20(m, 3H) | 163 | C 51.88; H 6.97 | C 51.81; H 6.93 |
| | 1640, 1600 | | | N 16.13; Cl 20.42 | N 16.23; Cl 20.51 |
| 34 | 3590, 3310 | 1.37(m, 14H), 2.26(m, 6H) | 317, 233, 219 | C$_{18}$H$_{36}$ON$_4$Cl$_2$ | |
| | 3200, 2950 | 4.11(t, 2H), 7.30(m, 3H) | 205 | C 54.68; H 9.18 | C 54.51; H 9.07 |
| | 1640, 1605 | | | N 14.17; Cl 17.93 | N 14.21; Cl 18.07 |
| 35 | 3610, 3300 | 0.85(d, 3H), 1.42(m, 8H) | 289, 274, 190 | C$_{16}$H$_{26}$ON$_4$Cl$_2$ | |
| | 3160, 2960 | 2.31(m, 5H), 4.21(t, 2H) | 177 | C 53.19; H 7.25 | C 53.07; H 7.19 |
| | 1625, 1570 | 7.19(m, 3H) | | N 15.51; Cl 19.62 | N 15.68; Cl 19.78 |
| 36 | 3590, 3300 | 0.91(t, 6H), 1.34(m, 11H) | 331, 274, 190 | C$_{19}$H$_{32}$ON$_4$Cl$_2$ | |
| | 3160, 2980 | 2.48(bs, 6H), 4.19(t, 2H) | 177 | C 56.57; H 8.00 | C 56.63; H 7.97 |
| | 1610, 1560 | 7.29(m, 3H) | | N 13.89; Cl 17.58 | N 13.91; Cl 17.43 |
| 37 | 3600, 3310 | 0.92(d, 3H), 1.51(m, 6H) | 289, 275, 193 | C$_{16}$H$_{26}$ON$_4$Cl$_2$ | |
| | 3200, 2940 | 2.33(m, 7H), 4.12(t, 2H) | 178 | C 53.19; H 7.25 | C 53.22; H 7.24 |
| | 1615, 1580 | 7.13(m, 3H) | | N 15.51; Cl 19.62 | N 15.48; Cl 19.71 |
| 38 | 3600, 3300 | 1.20(d, 6H), 1.38(m, 6H) | 303, 288, 191 | C$_{17}$H$_{28}$ON$_4$Cl$_2$ | |
| | 3220, 2940 | 2.29(m, 2H), 2.81(m, 2H) | 177 | C 54.40; H 7.52 | C 54.32; H 7.48 |
| | 1625, 1600 | 3.75(t, 2H), 4.21(t, 2H) | | N 14.93; Cl 18.89 | N 15.02; Cl 18.98 |
| | | 7.20(m, 3H) | | | |
| 39 | 3610, 3390 | 1.48(bs, 4H), 2.09(m, 3H) | 292, 275, 191 | C$_{15}$H$_{24}$ON$_4$Cl$_2$ | |
| | 3290, 2960 | 2.90(m, 6H), 4.22(t, 2H) | 177 | C 51.88; H 6.97 | C 52.01; H 7.01 |
| | 1625, 1570 | 7.19(m, 3H) | | N 16.13; Cl 20.42 | N 15.97; Cl 20.29 |
| 40 | 3615, 3340 | 1.45(bs, 4H), 2.10(m, 3H) | 309, 191, 177 | C$_{15}$H$_{23}$ON$_4$Cl$_3$ | |
| | 3260, 2950 | 2.88(m, 6H), 4.22(t, 2H) | 163 | C 47.20; H 6.07 | C 47.21; H 3.03 |
| | 1620, 1590 | 7.19(m, 3H) | | N 14.68; Cl 27.86 | N 14.65; Cl 27.91 |
| 41 | 3595, 3320 | 1.51(bs, 8H), 2.11(bs, 2H) | 289, 191, 177 | C$_{16}$H$_{26}$ON$_4$Cl$_2$ | |
| | 2940, 1630 | 2.48(bs, 6H), 4.21(t, 2H) | 163 | C 53.19; H 7.25 | C 53.21; H 7.27 |
| | 1590 | 7.22(m, 3H) | | N 15.51; Cl 19.62 | N 15.42; Cl 19.48 |
| 42 | 3590, 3320 | 2.31(m 15H), 4.15(t, 2H) | 290, 275, 260 | C$_{15}$H$_{26}$ON$_5$Cl$_3$ | |
| | 3210, 2930 | 7.19(m, 3H) | 204 | C 45.18; H 6.57 | C 45.20; H 6.51 |
| | 1630, 1590 | | | N 17.56; Cl 26.67 | N 17.61; Cl 26.55 |
| 43 | 3610, 3320 | 1.70(bm, 6H), 2.49(bm, 6H) | 260, 190, 176 | C$_{14}$H$_{22}$ON$_4$Cl$_2$ | |
| | 3170, 2920 | 4.23(t, 2H), 4.71(bs, 2H) | 162 | C 50.45; H 6.65 | C 50.42; H 6.68 |
| | 1640, 1610 | 7.21(m, 3H) | | N 16.81; Cl 21.28 | N 16.78; Cl 21.31 |
| 44 | 3600, 3170 | 1.60(m, 2H), 2.44(m, 6H) | 277, 191, 177 | C$_{14}$H$_{22}$O$_2$N$_4$Cl$_2$ | |
| | 2970, 1620 | 3.57(t, 4H), 4.20(t, 2H) | 163 | C 48.15; H 6.35 | C 48.11; H 6.39 |
| | 1605, 1570 | 7.30(m, 3H) | | N 16.04; Cl 20.30 | N 15.99; Cl 20.42 |

EXAMPLE 45

A mixture consisting of 5.04 g of 3-amino-4-chloroindazole, 8.30 g of 3-bromopropyldiethylamine hydrobromide, 8.3 g of anhydrous potassium carbonate and 80 ml of anhydrous N,N-dimethylformamide was stirred for 24 hours at 80° C. The reaction mixture was condensed under reduced pressure, the condensed residue was added with 100 ml of chloroform and 50 ml of water. The chloroform layer was separated and dried over anhydrous sodium sulfate, and then chloroform was removed under reduced pressure. The residue thus obtained was subjected to an alumina-column chromatography(alumina: 200 g) using chloroform as the developing solvent to give 5.16 g of 3-(3-diethylaminopropylamino)-4-chloroindazole having the following analytical values in a yield of 61%.

IR absorption spectrum ($\nu_{max}$, cm$^{-1}$): 3300, 3240, 2940, 2850, 1610 and 1590.

NMR spectrum [δ,CDCl$_3$]: 0.96(t, 6H), 2.35(m, 4H), 2.49(q, 4H), 4.21(t, 2H), 7.28(s, 2H) and 7.68(s, 1H).

Mass spectrum (m/e): 281(M$^+$), 283(M+2), 252(M-29), 223(M-58), 209(M-72) and 195(M-86).

In 50 ml of absolute ethyl alcohol was dissolved 4.0 g of 3-(diethylaminopropylamino)-4-chloroindazole and into the solution was introduced dried hydrogen chloride gas under cooling with ice. To the solution was added anhydrous diethyl ether to separate crystals. Then the crystals were obtained by filtration and dried to give 3-(3-diethylaminopropylamino)-4-chloroindazole hydrochloride having the following analytical value.

Elemental Analysis Value: C$_{14}$H$_{22}$N$_4$Cl$_2$: Calcd.(%): C 53.00; H 6.99; N 17.66; Cl 22.35. Found (%): C 52.91; H 7.05; N 17.57; Cl 22.47.

EXAMPLES 46–48

The same procedures as described in Example 45 were repeated except that 3-aminoindazoles as set forth in Table 16 were employed instead of the 5.04 g of 3-amino-4-chloroindazole. The results including the analytical values are shown in Tables 16 and 17.

TABLE 16

| Example No. | 3-Amino-chloroindazole | (g) | Product | Form | Yield (%) |
|---|---|---|---|---|---|
| 46 | 5-chloro-3-amino-1H-indazole | 5.04 | 5-chloro-3-[3-(diethylamino)propylamino]-1H-indazole | Solid | 51 |
| 47 | 6-chloro-3-amino-1H-indazole | 5.04 | 6-chloro-3-[3-(diethylamino)propylamino]-1H-indazole | Solid | 63 |
| 48 | 7-chloro-3-amino-1H-indazole | 5.04 | 7-chloro-3-[3-(diethylamino)propylamino]-1H-indazole | Solid | 59 |

TABLE 17

| Example No. | IR Spectrum (cm$^{-1}$) | NMR Spectrum ($\delta$, CDCl$_3$) | Mass Spectrum (m/e) | Elemental Analysis Value Calcd.(%) | Found(%) |
|---|---|---|---|---|---|
| 46 | 3310, 3210 | 0.98(t, 6H), 2.33(m, 4H) | 281, 283, 252 | C$_{14}$H$_{22}$N$_4$Cl$_2$ | |
|  | 2950, 2870 | 2.48(q, 4H), 4.23(t, 2H) | 223, 209, 195 | C 53.00; H 6.99 | C 53.15; H 7.02 |
|  | 1610, 1580 | 7.27(s, 2H), 7.69(s, 2H) |  | N 17.66; Cl 22.35 | N 17.41; Cl 22.42 |
| 47 | 3340, 3210 | 0.97(t, 6H), 2.35(m, 4H) | 281, 283, 252 | C$_{14}$H$_{22}$N$_4$Cl$_2$ | |
|  | 2950, 2890 | 2.49(q, 4H), 4.20(t, 2H) | 223, 209, 195 | C 53.00; H 6.99 | C 53.09; H 6.92 |
|  | 1615, 1580 | 6.87(d, 1H), 7.26(s, 1H) |  | N 17.66; Cl 22.35 | N 17.62; Cl 22.37 |
|  |  | 7.67(d, 1H) |  |  |  |
| 48 | 3320, 3240 | 0.96(t, 6H), 2.33(m, 4H) | 281, 283, 252 | C$_{14}$H$_{22}$N$_4$Cl$_2$ | |
|  | 2950, 2860 | 2.47(q, 4H), 4.23(t, 2H) | 224, 209, 195 | C 53.00; H 6.99 | C 52.89; H 7.18 |
|  | 1610, 1575 | 7.00(d, 1H), 7.30(d, 1H) |  | N 17.66; Cl 22.35 | N 17.65; Cl 22.28 |
|  |  | 7.63(d, 1H) |  |  |  |

EXAMPLE 49

To 80 ml of anhydrous N,N-dimethylformamide were added 4 g of 3-aminoindazole as prepared in accordance with the method described in C. E. Kwartler et al., J. Am. Chem. Soc., 65, 1804 (1943), 8.3 g of 3-bromopropyldiethylamine hydrobromide and 8.3 g of anhydrous potassium carbonate. The mixture was stirred for 24 hours at 80° C. and condensed under reduced pressure. To the condensed residue were added 100 ml of chloroform and 50 ml of water. The chloroform layer was dried over anhydrous sodium sulfate, and chloroform was removed under reduced pressure. The residue thus obtained was subjected to an alumina-column chromatography(alumina: 200 g) using chloroform as the developing solvent to give 3.85 g of 3-(3-diethylaminopropylamino)indazole having the following analytical values in a yield of 52%.

IR absorption spectrum ($\nu_{max}$, cm$^{-1}$): 3310, 3160, 2975, 1620 and 1550.

NMR spectrum [$\delta$,CDCL$_3$]: 0.99(t, 6H), 2.34(m, 4H), 2.47(q, 4H), 4.27(t, 2H), 5.06(bs, 1H) and 7.10(m, 4H).

Mass spectrum (m/e): 246(M$^+$), 174, 146, 132 and 112.

3-(3-Diethylaminopropylamino)-5-aminoindazole was prepared in accordance with the following method as described in R. Adam et al., "Laboratory Experiments in Organic Chemistry", 4th ed., pp.299, 301 and 303, Macmillan, New York, 1949 and S. E. Hazlet and C. A. Dornfeld, J. Am. Chem. Soc. 75, 4334 (1935).

In 2.58 ml of sulfuric acid was dissolved 1.5 g of 3-(3-diethylaminopropylamino)indazole. To the solution were added dropwise 0.41 ml of nitric acid(d=1.42) and 0.41 ml of sulfuric acid(sp. gr. 1.84) under cooling with ice, and the solution was stirred for 2 hours at 5°–10° C. To 12.1 ml of ice and water was added the solution, and the pH of the solution was adjusted to at least 11 with an aqueous ammonia solution. Then the solution was extracted with chloroform. The chloroform layer was dried over anhydrous sodium sulfate and chloroform was removed under reduced pressure. The residue was dissolved in 50 ml of anhydrous benzene. To the solution were added 10 g of iron powder and 2 ml of hydrochloric acid, and the solution was stirred for 30 minutes at 80° C. The reaction solution was added with 0.5 ml of water and stirred for 10 hours at 80° C. After cooling, the solution was filtered. The benzene layer of the filtrate was extracted three times with 20 ml of 1N hydrochloric acid. The pH of the hydrochloric acid layer was adjusted to at least 11 and the alkali layer was extracted with chloroform. The chloroform layer was dried over anhydrous sodium sulfate and chloroform was removed under reduced pressure. The residue thus obtained was subjected to an alumina-column chromatography(alumina: 100 g) using chloroform as the developing solvent to give 0.69 g of 3-(3-diethylaminopropylamino)-5-aminoindazole having the following analytical values in a yield of 44%.

IR absorption spectrum ($\nu_{max}$, cm$^{-1}$): 3340, 3210, 2940, 2870, 1615 and 1585.

NMR spectrum [δ,CD$_3$OD]: 0.97(t, 6H), 2.33(m, 4H), 2.47(q, 4H), 4.23(t, 2H) and 7.27(m, 3H).

Mass spectrum (m/e): 261(M+), 232(M-29), 203(M-58), 189(M-72) and 175(M-86).

Elemental Analysis Value: $C_{14}H_{25}N_5Cl_2$: Calcd.(%): C 50.30; H 7.54; N 20.95; Cl 21.21. Found (%): C 50.41; H 7.48; N 20.89; Cl 21.22.

EXAMPLES 50 and 51

The same procedures as described in Example 45 were repeated except that 3-aminoindazoles as set forth in Table 18 were employed instead of the 5.04 g of 3-amino-4-chloroindazole. The results including the analytical values are shown in Tables 18 and 19.

TABLE 18

| Example No. | 3-Aminoindazole | (g) | Product | Form | Yield (%) |
|---|---|---|---|---|---|
| 50 | CH$_3$O-[indazole]-NH$_2$ | 6.19 | CH$_3$O-[indazole]-NH(CH$_2$)$_3$N(C$_2$H$_5$)$_2$ | Solid | 59 |
| 51 | H$_3$C-[indazole]-NH$_2$ | 5.58 | H$_3$C-[indazole]-NH(CH$_2$)$_3$N(C$_2$H$_5$)$_2$ | Solid | 63 |

TABLE 19

| Example No. | IR Spectrum (cm$^{-1}$) | NMR Spectrum (δ, CDCl$_3$) | Mass Spectrum (m/e) | Elemental Analysis Value Calcd.(%) | Found(%) |
|---|---|---|---|---|---|
| 50 | 3310, 3200 2950, 2890 1620, 1590 | 0.97(t, 6H), 2.35(m, 4H) 2.48(q, 4H), 3.80(s, 3H) 4.21(t, 2H), 7.12(m, 3H) | 276, 247, 218 204, 190 | $C_{15}H_{25}ON_4Cl$ C 57.59; H 8.06 N 17.91; Cl 11.33 | C 57.54; H 8.14 N 17.89; Cl 11.41 |
| 51 | 3320, 3230 2970, 2860 1625, 1580 | 0.96(t, 6H), 2.33(s, 3H) 2.37(m, 4H), 2.47(q, 4H) 4.20(t, 2H), 7.08(s, 2H) 7.40(s, 1H) | 260, 231, 202 188, 174 | $C_{15}H_{25}N_4Cl$ C 60.69; H 8.49 N 18.88; Cl 11.94 | C 61.10; H 8.51 N 18.59; Cl 11.80 |

In 15 ml of absolute ethyl alcohol was dissolved 0.6 g of 3-(3-diethylaminopropylamino)-5-aminoindazole, and into the solution was introduced dried hydrogen chloride gas under cooling with ice. To the solution was added anhydrous diethyl ether to separate crystals. Then the crystals were obtained by filtration and dried to give 3-(3-diethylaminopropylamino)-5-aminoindazole dihydrochloride having the following analytical value.

EXAMPLES 52-66

The same procedures as described in Example 46 were repeated except that ω-halogenoalkylamine hydrobromides as set forth in Table 20 were employed instead of the 8.30 g of 3-bromopropyldiethylamine hydrobromide. The results including the analytical values are shown in Tables 20 and 21.

TABLE 20

| Example No. | ω-Halogenoalkylamine Hydrobromide | (g) | Product | Form | Yield (%) |
|---|---|---|---|---|---|
| 52 | (C$_4$H$_9$)$_2$N—(CH$_2$)$_3$Br·HBr | 9.90 | Cl-[indazole]-NH(CH$_2$)$_3$N(C$_4$H$_9$)$_2$ | Solid | 62 |
| 53 | (CH$_3$)$_2$N—CHCH$_2$CH$_2$Br·HBr (CH$_3$ branch) | 7.82 | Cl-[indazole]-NHCH$_2$CH$_2$CHN(CH$_3$)$_2$ (CH$_3$ branch) | Solid | 56 |

TABLE 20-continued

| Example No. | ω-Halogenoalkylamine Hydrobromide | (g) | Product | Form | Yield (%) |
|---|---|---|---|---|---|
| 54 | (C2H5)2N—CH(CH2CH(CH3)2)CH2CH2Br·HBr | 9.92 | 5-Cl-indazol-3-yl-NHCH2CH2CH(CH2CH(CH3)2)N(C2H5)2 | Solid | 52 |
| 55 | piperidino-CH2CH2CH2Br·HBr | 8.59 | 5-Cl-indazol-3-yl-NH(CH2)3N-piperidino | Solid | 50 |
| 56 | piperidino-(CH2)6Br·HBr | 9.87 | 5-Cl-indazol-3-yl-NH(CH2)6N-piperidino | Solid | 64 |
| 57 | piperidino-CH(CH3)CH2CH2Br·HBr | 9.00 | 5-Cl-indazol-3-yl-NHCH2CH2CH(CH3)N-piperidino | Solid | 59 |
| 58 | piperidino-CH(CH2CH(CH3)2)CH2CH2Br·HBr | 10.28 | 5-Cl-indazol-3-yl-NHCH2CH2CH(CH2CH(CH3)2)N-piperidino | Solid | 54 |
| 59 | 2-methylpiperidino-(CH2)3Br·HBr | 9.00 | 5-Cl-indazol-3-yl-NH(CH2)3N-(2-methylpiperidino) | Solid | 56 |
| 60 | 2,6-dimethylpiperidino-(CH2)3Br·HBr | 9.49 | 5-Cl-indazol-3-yl-NH(CH2)3N-(2,6-dimethylpiperidino) | Solid | 59 |
| 61 | 4-hydroxypiperidino-(CH2)3Br·HBr | 9.11 | 5-Cl-indazol-3-yl-NH(CH2)3N-(4-hydroxypiperidino) | Solid | 60 |

TABLE 20-continued

| Example No. | ω-Halogenoalkylamine Hydrobromide | (g) | Product | Form | Yield (%) |
|---|---|---|---|---|---|
| 62 | Cl—[piperidine]—N—(CH$_2$)$_3$Br·HBr | 9.67 | 5-Cl-indazol-3-yl—NH(CH$_2$)$_3$N—[piperidine]—Cl | Solid | 61 |
| 63 | [azocane]N—(CH$_2$)$_3$Br·HBr | 9.06 | 5-Cl-indazol-3-yl—NH(CH$_2$)$_3$N—[azocane] | Solid | 59 |
| 64 | CH$_3$—N[piperazine]N—(CH$_2$)$_3$Br·HBr | 8.56 | 5-Cl-indazol-3-yl—NH(CH$_2$)$_3$N[piperazine]N—CH$_3$ | Solid | 58 |
| 65 | [pyrrolidine]N—(CH$_2$)$_3$Br·HBr | 8.19 | 5-Cl-indazol-3-yl—NH(CH$_2$)$_3$N[pyrrolidine] | Solid | 54 |
| 66 | O[morpholine]N—(CH$_2$)$_3$Br·HBr | 8.64 | 5-Cl-indazol-3-yl—NH(CH$_2$)$_3$N[morpholine]O | Solid | 58 |

TABLE 21

| Example No. | IR Spectrum (cm$^{-1}$) | NMR Spectrum (δ, CDCl$_3$) | Mass Spectrum (m/e) | Elemental Analysis Value Calcd. (%) | Elemental Analysis Value Found (%) |
|---|---|---|---|---|---|
| 52 | 3320, 3220 | 0.92(m, 6H), 1.28(m, 10H) | 337, 339, 280 | C$_{18}$H$_{30}$N$_4$Cl$_2$ | |
|  | 3000, 2960 | 2.31(m, 6H), 4.21(t, 2H) | 223, 209 | C 57.9; H 8.10 | C 58.02; H 7.97 |
|  | 1640, 1600 1570 | 7.28(s, 2H), 7.71(s, 1H) |  | N 15.00; Cl 18.99 | N 14.98; Cl 19.03 |
| 53 | 3310, 3160 | 0.87(d, 3H), 1.34(m, 2H) | 267, 269, 252 | C$_{13}$H$_{20}$N$_4$Cl$_2$ | |
|  | 2970, 1610 | 2.25(s, 6H), 2.35(m, 1H) | 237, 222 | C 51.49; H 6.65 | C 51.30, H 6.49 |
|  | 1580 | 4.23(t, 2H), 7.26(s, 2H) 7.69(s, 1H) |  | N 18.48; Cl 23.38 | N 18.69; Cl 23.52 |
| 54 | 3320, 3140 | 0.95(m, 12H), 1.33(m, 5H) | 337, 339, 280 | C$_{18}$H$_{30}$N$_4$Cl$_2$ | |
|  | 2970, 1615 | 2.55(m, 5H), 4.21(t, 2H) | 208, 195 | C 57.91; H 8.10 | C 57.87; H 8.21 |
|  | 1580 | 7.26(s, 2H), 7.67(s, 1H) |  | N 15.00; Cl 18.00 | N 14.92; Cl 19.00 |
| 55 | 3310, 3215 | 1.43(m, 6H), 2.19(m, 8H) | 293, 295, 208 | C$_{13}$H$_{22}$N$_4$Cl$_2$ | |
|  | 2960, 1630 | 4.23(t, 2H), 7.27(s, 2H) | 195, 181 | C 51.15; H 7.27 | C 50.98; H 7.34 |
|  | 1605 | 7.68(s, 1H) |  | N 18.35; Cl 23.23 | N 189.41; Cl 23.27 |
| 56 | 3340, 3210 | 1.37(m, 14H), 2.28(m, 6H) | 335, 337, 251 | C$_{18}$H$_{28}$N$_4$Cl$_2$ | |
|  | 2950, 1640 | 4.13(t, 2H), 7.26(s, 2H) | 237, 223 | C 58.22; H 7.60 | C 58.27; H 7.71 |
|  | 1610 | 7.67(s, 1H) |  | N 15.09; Cl 19.09 | N 14.91; Cl 19.11 |
| 57 | 3310, 3160 | 0.86(d, 3H), 1.42(m, (8H) | 307, 309, 292 | C$_{16}$H$_{24}$N$_4$Cl$_2$ | |
|  | 2960, 1625 | 2.31(m, 5H), 4.21(t, 2H) | 208, 195 | C 55.98; H 7.05 | C 56.28; H 6.75 |
|  | 1600, 1575 | 7.27(s, 2H), 7.69(s, 1H) |  | N 16.32; Cl 20.65 | N 16.02; Cl 20.95 |
| 58 | 3320, 3160 | 0.90(t, 6H), 1.33(m, 11H) | 349, 351, 292 | C$_{19}$H$_{30}$N$_4$Cl$_2$ | |
|  | 2980, 1620 | 2.47(bs, 6H), 4.19(t, 2H) | 208, 195 | C 59.22; H 7.85 | C 58.92; H 8.15 |
|  | 1605, 1550 | 7.26(s, 2H), 7.67(s, 1H) |  | N 14.54; Cl 18.39 | N 14.24; Cl 18.69 |
| 59 | 3310, 3210 | 0.91(d, 3H), 1.50(m, 6H) | 307, 309, 293 | C$_{16}$H$_{24}$N$_4$Cl$_2$ | |
|  | 2950, 2880 | 2.32(m, 7H), 4.15(t, 2H) | 211, 196 | C 55.98; H 7.05 | C 55.68; H 7.35 |
|  | 1620, 1590 | 7.28(s, 2H), 7.67(s, 1H) |  | N 16.32; Cl 20.65 | N 16.62; Cl 20.35 |

TABLE 21-continued

| Example No. | IR Spectrum (cm$^{-1}$) | NMR Spectrum (δ, CDCl$_3$) | Mass Spectrum (m/e) | Elemental Analysis Value Calcd. (%) | Found (%) |
|---|---|---|---|---|---|
| 60 | 3315, 3210 | 1.20(d, 6H), 1.39(m, 6H) | 321, 323, 306 | \multicolumn{2}{c}{C$_{17}$H$_{26}$N$_4$Cl$_2$} |
|  | 2950, 2880 | 2.30(m, 2H), 2.81(m, 2H) | 209, 195 | C 57.14; H 7.33 | C 57.44; H 7.63 |
|  | 1625, 1600 | 3.75(t, 2H), 4.21(t, 2H) |  | N 15.68; Cl 19.85 | N 15.38; Cl 19.55 |
|  |  | 7.24(s, 2H), 7.67(s, 1H) |  |  |  |
| 61 | 3390, 3290 | 1.47(bs, 4H), 2.08(m, 3H) | 310, 312, 293 | \multicolumn{2}{c}{C$_{15}$H$_{22}$ON$_4$Cl$_2$} |
|  | 2960, 1620 | 2.88(m, 6H), 4.22(t, 2H) | 209, 195 | C 52.18; H 6.42 | C 52.48; H 6.12 |
|  | 1580 | 7.25(s, 2H), 7.71(s, 1H) |  | N 16.23; Cl 20.54 | N 16.53; Cl 20.24 |
| 62 | 3340, 3270 | 1.45(bs, 4H), 2.08(m, 3H) | 327, 292, 209 | \multicolumn{2}{c}{C$_{15}$H$_{21}$N$_4$Cl$_2$} |
|  | 2960, 2880 | 2.88(m, 6H), 4.20(t, 2H) | 195, 181 | C 49.53; H 5.82 | C 49.23; H 6.12 |
|  | 1620, 1590 | 7.25(s, 2H), 7.69(s, 1H) |  | N 15.40; Cl 29.25 | N 15.10; Cl 29.55 |
| 63 | 3310, 3150 | 1.52(bs, 8H), 2.11(bs, 2H) | 307(M$^+$), 309 | \multicolumn{2}{c}{C$_{16}$H$_{24}$N$_4$Cl$_2$} |
|  | 2950, 1630 | 2.47(bs, 6H), 4.21(t, 2H) | 209, 195, 181 | C 55.98; H 7.05 | C 56.28; H 6.75 |
|  | 1600 | 7.27(s, 2H), 7.70(s, 1H) |  | N 16.32; Cl 20.65 | N 16.85; Cl 20.12 |
| 64 | 3330, 3210 | 2.32(m, 15H), 4.20(t, 2H) | 309, 310, 293 | \multicolumn{2}{c}{C$_{15}$H$_{24}$N$_5$Cl$_3$} |
|  | 2950, 2810 | 7.27(s, 2H), 7.69(s, 1H) | 278, 222 | C 47.32; H 6.35 | C 47.62; H 6.65 |
|  | 1630, 1590 |  |  | N 18.39; Cl 27.94 | N 18.09; Cl 27.64 |
| 65 | 3310, 3190 | 1.68(bm, 6H), 2.49(bm, 6H) | 278, 280, 208 | \multicolumn{2}{c}{C$_{14}$H$_{20}$N$_4$Cl$_2$} |
|  | 2920, 1640 | 4.23(t, 2H), 4.70(bs, 2H) | 194, 180 | C 53.34; H 6.39 | C 53.31; H 6.42 |
|  | 1610 | 7.20(s, 2H), 7.69(s, 1H) |  | N 17.78; Cl 22.49 | N 17.75; Cl 22.53 |
| 66 | 3400, 3160 | 1.60(m, 2H), 2.44(m, 6H) | 295, 297, 209 | \multicolumn{2}{c}{C$_{14}$H$_{20}$ON$_4$Cl$_2$} |
|  | 2970, 1610 | 3.57(t, 4H), 4.20(t, 2H) | 195, 181 | C 50.76; H 6.09 | C 60.06; H 6.39 |
|  | 1600 | 7.29(s, 2H), 7.68(s, 1H) |  | N 10.91; Cl 21.41 | N 16.61; Cl 21.11 |

EXAMPLE 67

To 80 ml of anhydrous N,N-dimethylformamide were added 5.04 g of 3-amino-4-chloroindazole prepared by the same method as in Example 1, 8.30 g of 3-bromopropyldiethylamine hydrobromide and 8.3 g of anhydrous potassium carbonate. The mixture was stirred for 24 hours at 80° C. and condensed under reduced pressure. The condensed residue was added with 100 ml of chloroform and 50 ml of water. The chloroform layer was dried over anhydrous sodium sulfate, and chloroform was removed under reduced pressure. The residue thus obtained was subjected to an alumina-column chromatography(alumina: 200 g) using chloroform as the developing solvent to give 5.16 g of 3-(3-diethylaminopropylamino)-4-chloroindazole having the following analytical values in a yield of 61%.

IR absorption spectrum ($\nu_{max}$, cm$^{-1}$): 3300, 3240, 2940, 2850, 1610 and 1590.

NMR spectrum [δ,CDCl$_3$]: 0.96(t, 6H), 2.35(m, 4H), 2.49(q, 4H), 4.21(t, 2H), 7.28(s, 2H) and 7.68(s, 1H).

Mass spectrum (m/e): 281(M+), 283(M+2), 252(M-29), 223(M-58), 209(M-72) and 195(M-86).

To 20 ml of diethyl ether solution containing 600 mg of magnesium powder was added dropwise a mixed solution consisting of 2.81 g of the 3-(3-diethylaminopropylamino)-4-chloroindazole, 2.06 g of isopropyl bromide and 20 ml of diethyl ether. Into the solution were introduced dried oxygen gas and dried carbon dioxide gas for 10 hours so as to reflux the solution, and the solution was left to stand for 12 hours. The pH of the solution was adjusted to 4.0 by adding dropwise sulfuric acid to the solution at 0° C. The solution was added with 50 ml of water and filtered. To the aqueous layer of the filtrate was added an aqueous potassium carbonate solution to separate crystals. The crystals were obtained by filtration and dried to give 1.08 g of 3-(3-diethylaminopropylamino)-4-hydroxyindazole having the following analytical values in a yield of 41%.

IR absorption spectrum ($\nu_{max}$, cm$^{-1}$): 3600, 3320, 2980, 1615 and 1570.

NMR spectrum [δ,CD$_3$OD]: 0.96(t, 6H), 2.36(m, 4H), 2.47(g, 4H), 4.19(t, 2H) and 7.17(m, 3H).

Mass spectrum (m/e): 264(M+), 234(M-29), 205(M-53), 191(M-72) and 177(M-88).

In 50 ml of absolute ethyl alcohol was dissolved 3.0 g of the 3-(3-diethylaminopropylamino)-4-hydroxyindazole, and into the solution was introduced dried hydrogen chloride gas under cooling with ice. To the solution was added anhydrous diethyl ether to separate crystals. Then the crystals were obtained by filtration and dried to give 3-(3-diethylaminopropylamino)-4-hydroxyindazole hydrochloride having the following analytical value.

Elemental Analysis Value: C$_{14}$H$_{23}$ON$_4$Cl: Calcd.(%): C 56.27; H 7.76; N 18.75; Cl 11.86. Found (%): C 56.22; H 7.74; N 18.86; Cl 11.84.

EXAMPLE 68

To 80 ml of anhydrous N,N-dimethylformamide were added 5.0 g of 3-aminoindazole, 8.30 g of 3-bromopropyldiethylamine hydrobromide and 8.3 g of anhydrous potassium carbonate. The mixture was stirred for 24 hours at 80° C. and condensed under reduced pressure. The condensed residue was added with 100 ml of chloroform and 50 ml of water. The chloroform layer was dried over anhydrous sodium sulfate, and chloroform was removed under reduced pressure. The residue thus obtained was subjected to an alumina-column chromatography(alumina: 200 g) using chloroform as the development solvent to give 4.81 g of 3-(3-diethylaminopropylamino)indazole having the following analytical values in a yield of 52%.

IR absorption spectrum ($\nu_{max}$, cm$^{-1}$): 3310, 3160, 2975, 1620 and 1550.

NMR spectrum [δ,CDCl$_3$]: 0.99(t, 6H), 2.34(m, 4H), 2.47(q, 4H), 4.27(t, 2H), 5.06(bs, 1H) and 7.10(m, 4H).

Mass spectrum (m/e): 246(M+), 174(M-72), 146(M-100), 132(M-114) and 112(M-134).

To 4.3 g of 95% sulfuric acid was added 9.25 g of the 3-(3-diethylaminopropylamino)indazole, and the mixture was stirred for 3 hours at 80° C. To the mixture was added 13 ml of water, and the pH of the mixture was adjusted to 14 with potassium hydroxide. The mixture was washed twice with 20 ml of chloroform, and water was removed under reduced pressure. To the residue thus obtained were added 12.5 g of potassium hydroxide and 0.6 ml of water, and the mixture was stirred for 8 hours at 250° C. After cooling, to the mixture was added hydrochloric acid to separate crystals. Then the crystals were obtained by filtration and dried to give 4.39 g of 3-(3-diethylaminopropylamino)-5-hydroxyindazole having the following analytical values in a yield of 40%.

IR absorption spectrum ($\nu_{max}$, cm$^{-1}$): 3590, 3340, 3010, 2980, 1610 and 1580.

NMR spectrum [$\delta$,CD$_3$OD]: 0.95(t, 6H), 2.33(m, 4H), 2.49(q, 4H), 4.22(t, 2H) and 7.13(m, 3H).

Mass spectrum (m/e): 262(M$^+$), 164(M-98), 150(M-112) and 136(M-126).

In 50 ml of absolute ethyl alcohol was dissolved 4.0 g of the 3-(3-diethylaminopropylamino)-5-hydroxyindazole, and into the solution was introduced dried hydrogen chloride gas under cooling with ice. To the solution was added anhydrous diethyl ether to separate crystals. Then the crystals were obtained by filtration and dried to give 3-(3-diethylaminopropylamino)-5-hydroxyindazole hydrochloride.

Elemental Analysis Value: C$_{14}$H$_{23}$ON$_4$Cl: Calcd.(%): C 56.27; H 7.76; N 18.75; Cl 11.86. Found (%): C 56.18, H 7.68; N 18.86; Cl 11.91.

EXAMPLES 69 and 70

The same procedures as described in Example 67 were repeated except that 3-amino-6-chloroindazole and 3-amino-7-chloroindazole were employed, respectively, instead of the 3-amino-4-chloroindazole. The results including the analytical values are shown in Tables 22 and 23.

in accordance with the method described in C. E. Kwartler et el., J. Am. Chem. Soc., 65 1804(1943), 8.3 g of 3-bromopropyldiethylamine hydrobromide and 8.3 g of anhydrous potassium carbonate. The mixture was stirred for 24 hours at 80° C. and condensed under reduced pressure. The condensed residue was added with 100 ml of chloroform and 50 ml of water. The chloroform layer was dried over anhydrous sodium sulfate, and chloroform was removed under reduced pressure. The residue thus obtained was subjected to an alumina-column chromatography(alumina: 200 g) using chloroform as the developing solvent to give 7.15 g of 3-(3-diethylaminopropylamino)-5-iodoindazole having the following analytical values in a yield of 51%.

IR absorption spectrum ($\nu_{max}$, cm$^{-1}$): 3300, 3165, 2970, 1610 and 1540.

NMR spectrum [$\delta$, CDCl$_3$]: 0.98(t, 6H), 2.36(m, 4H), 2.49(q, 4H), 4.26(t, 2H), 7.02(d, 1H), 7.35(d, 1H) and 8.01(s, 1H).

Mass spectrum (m/e): 373(M$^+$), 301, 273, 259 and 239.

In 50 ml of absolute ethyl alcohol was dissolved 4.0 g of the 3-(3-diethylaminopropylamino)-5-iodoindazole, and into the solution was introduced dried hydrogen chloride gas under cooling with ice. Then to the solution was added anhydrous diethyl ether to separate crystals. The crystals were obtained by filtration and dried to give 3-(3-diethylaminopropylamino)-5-iodoindazole hydrochloride having the following analytical value.

Elemental Analysis Value: C$_{41}$H$_{22}$N$_4$ICl: Calcd. (%): C 41.14; H 5.43; N 13.71, I 31.05; Cl 8.67. Found (%): C 40.98; H 5.39; N 13.93; I 30.99; Cl 8.71.

EXAMPLE 72

The same procedures for preparing 3-(3-die-

TABLE 22

| Example No. | 3-Amino-chloroindazole | (g) | Product | Form | Yield (%) |
|---|---|---|---|---|---|
| 69 | (Cl-substituted indazole with NH$_2$) | 5.04 | (OH-substituted indazole with NH(CH$_2$)$_3$N(C$_2$H$_5$)$_2$) | Solid | 48 |
| 70 | (Cl-substituted indazole with NH$_2$) | 5.04 | (OH-substituted indazole with NH(CH$_2$)$_3$N(C$_2$H$_5$)$_2$) | Solid | 38 |

TABLE 23

| Example No. | IR Spectrum (cm$^{-1}$) | NMR Spectrum ($\delta$, CD$_3$OD) | Mass Spectrum (m/e) | Elemental Analysis Value Calcd. (%) | Elemental Analysis Value Found (%) |
|---|---|---|---|---|---|
| 69 | 3600, 3320 2980, 1615 1580 | 0.97(t, 6H), 2.34(m, 4H) 2.49(q, 4H), 4.20(t, 2H) 7.20(m, 3H) | 263(M$^+$), 234 205, 191, 177 | C$_{14}$H$_{23}$ON$_4$Cl C 56.27; H 7.76 N 18.75; Cl 11.86 | C 56.20; H 7.68 N 18.86; Cl 11.90 |
| 70 | 3590, 3310 2970, 1610 1570 | 0.98(t, 6H), 2.35(m, 4H) 2.46(q, 4H), 4.19(t, 2H) 7.21(m, 3H) | 263(M$^+$), 234 205, 191, 177 | C$_{14}$H$_{23}$ON$_4$Cl C 56.27; H 7.76 N 18.75; Cl 11.86 | C 56.12; H 7.68 N 18.88; Cl 11.91 |

EXAMPLE 71

To 80 ml of anhydrous N,N-dimethylformamide were added 9.7 g of 3-amino-5-iodoindazole as prepared thylaminopropylamino)-5-iodoindazole as described in Example 71 were repeated except that 3-amino-7- iodoindazole was employed instead of the 3-amino-5-iodoindazole. As a result, 7.57 g of 3-(3-diethylaminopropylamino)-7-iodoindazole having the following analytical values was obtained in a yield of 54%.

IR absorption spectrum ($\nu_{max}$, cm$^-$): 3320, 3170, 2980, 1605 and 1550.

NMR spectrum [δ, CDCl$_3$]: 0.99(t, 6H), 2.37(m, 4H), 2.48(q, 4H), 4.20(t, 2H), 7.02(d, 1H), 7.32(d, 1H) and 7.70(d, 1H).

Mass spectrum (m/e): 373(M+), 301, 273, 259 and 239.

In 50 ml of absolute ethyl alcohol was dissolved 4.0 g of the 3-(3-diethylaminopropylamino)-7-iodoindazole, and into the solution was introduced dried hydrogen chloride gas under cooling with ice. Then to the solution was added anhydrous diethyl ether to separate crystals. The crystals were obtained by filtration and dried to give 3-(3-diethylaminopropylamino)-7-iodoindazole hydrochloride having the following analytical value.

Elemental Analysis Value: C$_{14}$H$_{22}$N$_4$ICl: Calcd.(%): C 41.14; H 5.43; N 13.71; I 31.05; Cl 8.67. Found (%): C 40.93; H 5.39; N 13.99; I 31.17; Cl 8.52.

EXAMPLE 73

The same procedures for preparing 3-(3-diethylaminopropylamino)-5-iodoindazole as described in Example 71 were repeated except that 4.0 g of 3-aminoindazole was employed instead of the 9.7 g of 3-amino-5-iodoindazole. As a result, 4.0 g of 3-(3-diethylaminopropylamino)indazole having the following analytical values was obtained in a yield of 54 %.

IR absorption spectrum ($\nu_{max}$, cm$^{-1}$): 3310, 3160, 2975, 1620 and 1550.

NMR spectrum [δ, CDCl$_3$: 0.99(t, 6H), 2.34(m, 4H), 2.47(q, 9H), 4.27(t, 2H) and 7.10(m, 4H).

Mass spectrum (m/e): 246(M+), 174(M-72), 146(M-100), 132(M-114) and 112(M-134).

In 30 ml of sulfuric acid was dissolved 40 g of the 3-(3-diethylaminopropylamino)indazole. To the solution were added dropwise 10.2 ml of nitric acid and 10.2 ml of sulfuric acid at 0° C., and the solution was stirred for 1 hour. The pH of the solution was adjusted to 10.4 with an aqueous ammonia solution, and the solution was extracted three times with 50 ml of chloroform. The chloroform layer was washed with water and dried over anhydrous sodium sulfate, and then chloroform was removed under reduced pressure. The residue thus obtained was subjected to an alumina-column chromatography(alumina: 200 g) using chloroform as the developing solvent to give 9.55 g of 3-(3-diethylaminopropylamino)-5,7-dinitroindazole having the following analytical values in a yield of 19%.

IR absorption spectrum ($\nu_{max}$, cm$^-$) 3470, 3360, 3090 and 1610.

NMR spectrum [6, ds-DMSO]: 0.98(t, 6H), 2.34(m, 4H), 2.48(q. 4H), 4.20(t, 2H) and 7.87(s. 1H) and 8.10(s, 1H).

Mass spectrum (m/e): 337(M+), 291(M-46), 245(M-92) and 229(M-108).

A mixture consisting of 9.0 g of the 3-(3-diethylaminopropylamino)-5,7-dinitroindazole, 18 g of iron powder, 60 ml of methyl alcohol, 30 ml of water and 3 ml of hydrochloric acid was stirred for 1.5 hours at 70° C. After cooling, the mixture was filtered, and the pH of the filtrate was adjusted to 11 with an aqueous potassium carbonate solution. The filtrate was extracted three times with 50 ml of ethyl acetate. The ethyl acetate layer was washed with water and dried over anhydrous sodium sulfate. Then, ethyl acetate was removed under reduced pressure. The residue thus obtained was subjected to an alumina-column chromatography(alumina: 200 g) using chloroform as the developing solvent to give 1.67 g of 3-(3-diethylaminopropylamino)-5,7-diaminoindazole having the following analytical values in a yield of 22%.

IR absorption spectrum ($\nu_{max}$, cm$^{-1}$): 3470, 3330, 3170, 1630 and 1600.

NMR spectrum [6, CD$_3$OD]: 0.98(t, 6H), 2.34(m, 4H), 2.48(q. 4H), 4.20(t, 2H) and 6.92(m, 2H).

Mass spectrum (m/e): 277(M+), 261(M-16), 245(M-32) and 229(M-48).

In 20 ml of absolute ethyl alcohol was dissolved 2.0 g of the 3-(3-diethylaminopropylamino)-5,7-diaminoindazole, and into the solution was introduced dried hydrogen chloride gas under cooling with ice. Then to the solution was added anhydrous diethyl ether to separate crystals. The crystals were obtained by filtration and dried to give 3-(3-diethylaminopropylamino)-5,7-diaminoindazole trihydrochloride having the following analytical value.

Elemental Analysis Value: C$_4$H$_{27}$N$_6$C$_3$: Calcd.(%): C 43.59; H 7.05; N 21.79; Cl 27.57. Found (%): C 43.51; H 6.98; N 21.98; Cl 27.53.

EXAMPLES 74-88

The same procedures as described in Example 68 were repeated except that ω-halogenoalkylamine hydrobromides as set forth in Table 24 were employed instead of the 8.30 g of 3-bromopropyldiethylamine hydrobromide. The results including the analytical values are shown in Tables 24 and 25.

TABLE 24

| Example No. | ω-Halogenoalkylamine Hydrobromide | (g) | Product | Form | Yield (%) |
|---|---|---|---|---|---|
| 74 | C$_4$H$_9$\N—(CH$_2$)$_3$Br.HBr / C$_4$H$_9$ | 9.90 | HO-[indazole]-NH(CH$_2$)$_3$N(C$_4$H$_9$)$_2$ | Solid | 63 |
| 75 | CH$_3$\N—CHCH$_2$CH$_2$Br.HBr / CH$_3$  CH$_3$ | 7.82 | HO-[indazole]-NHCH$_2$CH$_2$CHN(CH$_3$)$_2$ with CH$_3$ | Solid | 57 |

TABLE 24-continued

| Example No. | ω-Halogenoalkylamine Hydrobromide | (g) | Product | Form | Yield (%) |
|---|---|---|---|---|---|
| 76 | (C$_2$H$_5$)$_2$N—CHCH$_2$CH$_2$Br·HBr with CH(CH$_3$)$_2$ branch | 9.92 | 5-HO-indazole-3-NHCH$_2$CH$_2$CH[N(C$_2$H$_5$)$_2$]—CH(CH$_3$)$_2$ | Solid | 53 |
| 77 | Piperidinyl-N—CH$_2$CH$_2$CH$_2$Br·HBr | 8.59 | 5-HO-indazole-3-NH(CH$_2$)$_3$N(piperidinyl) | Solid | 51 |
| 78 | Piperidinyl-N—(CH$_2$)$_6$Br·HBr | 9.87 | 5-HO-indazole-3-NH(CH$_2$)$_6$N(piperidinyl) | Solid | 66 |
| 79 | Piperidinyl-N—CHCH$_2$CH$_2$Br·HBr with CH$_3$ | 9.00 | 5-HO-indazole-3-NHCH$_2$CH$_2$CH(CH$_3$)N(piperidinyl) | Solid | 60 |
| 80 | Piperidinyl-N—CHCH$_2$CH$_2$Br·HBr with CH(CH$_3$)$_2$ branch | 10.28 | 5-HO-indazole-3-NHCH$_2$CH$_2$CH[N(piperidinyl)]CH(CH$_3$)$_2$ | Solid | 55 |
| 81 | 2-methylpiperidinyl-N(CH$_2$)$_3$Br·HBr | 9.00 | 5-HO-indazole-3-NH(CH$_2$)$_3$N(2-methylpiperidinyl) | Solid | 57 |
| 82 | 2,6-dimethylpiperidinyl-N—(CH$_2$)$_3$Br·HBr | 9.49 | 5-HO-indazole-3-NH(CH$_2$)$_3$N(2,6-dimethylpiperidinyl) | Solid | 60 |
| 83 | 4-hydroxypiperidinyl-N—(CH$_2$)$_3$Br·HBr | 9.11 | 5-HO-indazole-3-NH(CH$_2$)$_3$N(4-hydroxypiperidinyl) | Solid | 61 |

TABLE 24-continued

| Example No. | ω-Halogenoalkylamine Hydrobromide | (g) | Product | Form | Yield (%) |
|---|---|---|---|---|---|
| 84 | 4-chloropiperidine-N—(CH$_2$)$_3$Br·HBr | 9.67 | 5-hydroxy-3-[NH(CH$_2$)$_3$N(4-chloropiperidinyl)]-1H-indazole | Solid | 62 |
| 85 | azocane-N—(CH$_2$)$_3$Br·HBr | 9.06 | 5-hydroxy-3-[NH(CH$_2$)$_3$N(azocanyl)]-1H-indazole | Solid | 60 |
| 86 | H$_3$C—N(piperazine)N(CH$_2$)$_3$Br·HBr | 8.56 | 5-hydroxy-3-[NH(CH$_2$)$_3$N(4-methylpiperazinyl)]-1H-indazole | Solid | 59 |
| 87 | pyrrolidine-N—(CH$_2$)$_3$Br·HBr | 8.22 | 5-hydroxy-3-[NH(CH$_2$)$_3$N(pyrrolidinyl)]-1H-indazole | Solid | 53 |
| 88 | morpholine-N—(CH$_2$)$_3$Br·HBr | 8.64 | 5-hydroxy-3-[NH(CH$_2$)$_3$N(morpholinyl)]-1H-indazole | Solid | 59 |

TABLE 25

| Example No. | IR Spectrum (cm$^{-1}$) | NMR Spectrum (δ, CD$_3$OD) | Mass Spectrum (m/e) | Elemental Analysis Value Calcd. (%) | Found (%) |
|---|---|---|---|---|---|
| 74 | 3600, 3310 3200, 3000 2950, 1640 | 0.92(m, 6H), 1.27(m, 10H) 2.32(m, 6H), 4.21(t, 2H) 7.20(m, 3H) | 319, 262, 205 191 | C$_{19}$H$_{31}$ON$_4$Cl C 60.91; H 8.80 N 15.79; Cl 9.99 | C 60.89; H 8.71 N 15.88; Cl 10.02 |
| 75 | 3610, 3315 3150, 2965 1605, 1570 | 0.88(d, 3H), 1.35(m, 2H) 2.26(s, 6H), 2.34(m, 1H) 4.23(t, 2H), 7.18(m, 3H) | 249, 234, 219 204 | C$_{13}$H$_{21}$ON$_4$Cl C 54.83; H 7.43 N 19.67; Cl 12.45 | C 54.91; H 7.51 N 19.52; Cl 12.41 |
| 76 | 3590, 3330 3150, 2975 1620, 1590 | 0.96(m, 12H), 1.31(m, 5H) 2.54(m, 5H), 4.23(t, 2H) 7.21 (m, 3H) | 319, 262, 190 177 | C$_{18}$H$_{31}$ON$_4$Cl C 60.91; H 8.80 N 15.79; Cl 9.99 | C 60.99; H 8.81 N 15.57; Cl 10.03 |
| 77 | 3605, 3315 3220, 2950 1640, 1610 | 1.45(m, 6H), 2.17(m, 8H) 4.21(t, 2H), 7.22(m, 3H) | 275, 190, 177 163 | C$_{13}$H$_{23}$ON$_4$Cl C 54.44; H 8.08 N 19.53; Cl 12.36 | C 54.51; H 7.98 N 19.49; Cl 12.44 |
| 78 | 3595, 3330 3200, 2945 1630, 1600 | 1.35(m, 14H), 2.26(m, 6H) 4.14(t, 2H), 7.18(m, 3H) | 307, 233, 219 205 | C$_{18}$H$_{29}$ON$_4$Cl C 61.26; H 8.28 N 15.88; Cl 10.05 | C 61.29; H 8.31 N 15.71; Cl 9.98 |
| 79 | 3600, 3315 3160, 2965 1620, 1605 1580 | 0.85(d, 3H), 1.41(m, 8H) 2.30(m, 5H), 4.21(t, 2H) 7.21(m, 3H) | 289, 274, 190 177 | C$_{16}$H$_{25}$ON$_4$Cl C 59.16; H 7.76 N 17.25; Cl 10.91 | C 58.99; H 7.91 N 17.29; Cl 10.93 |
| 80 | 3605, 3325 3195, 2970 1630, 1600 | 0.90(t, 6H), 1.32(m, 11H) 2.46(bs, 6H), 4.18(t, 2H) 7.22(m, 3H) | 331, 274, 190 177 | C$_{19}$H$_{31}$ON$_4$Cl C 62.19; H 8.52 N 15.27; Cl 9.66 | C 62.21; H 8.61 N 15.20; Cl 9.51 |
| 81 | 3610, 3305 3200, 2940 2870, 1615 1595 | 0.90(d, 3H), 1.51(m, 6H) 2.31(m, 7H), 4.15(t, 2H) 7.18(m, 3H) | 289, 275, 193 178 | C$_{16}$H$_{25}$ON$_4$Cl C 59.11; H 7.75 N 17.23; Cl 10.91 | C 59.23; H 7.81 N 17.11; Cl 10.83 |

TABLE 25-continued

| Example No. | IR Spectrum (cm$^{-1}$) | NMR Spectrum (δ, CD$_3$OD) | Mass Spectrum (m/e) | Elemental Analysis Value | |
|---|---|---|---|---|---|
| | | | | Calcd. (%) | Found (%) |
| 82 | 3590, 3320 | 1.22(d, 6H), 1.38(m, 6H) | 303, 288, 191 | C$_{17}$H$_{27}$ON$_4$Cl | |
| | 3220, 2955 | 2.31(m, 2H), 2.80(m, 2H) | 177 | C 60.25; H 8.03 | C 60.13; H 7.97 |
| | 2870, 1630 | 3.74(t, 2H), 4.20(t, 2H) | | N 16.53; Cl 10.46 | N 16.71; Cl 10.49 |
| | 1610 | 7.19(m, 3H) | | N 17.14; Cl 10.85 | N 17.21; Cl 10.99 |
| 84 | 3605, 3330 | 1.47(bs, 4H), 2.07(m, 3H) | 309, 191, 177 | C$_{15}$H$_{22}$ON$_4$Cl | |
| | 3260, 2970 | 2.86(m, 6H), 4.18(t, 2H) | 163 | C 52.18; H 6.42 | C 52.21; H 6.51 |
| | 2890, 1615 | 7.21(m, 3H) | | N 16.22; Cl 20.34 | N 16.28; Cl 20.38 |
| | 1585 | | | | |
| 85 | 3610, 3303 | 1.52(bs, 8H), 2.10(bs, 2H) | 289, 191, 177 | C$_{16}$H$_{25}$ON$_4$Cl | |
| | 3155, 2960 | 2.45(bs, 6H), 4.20(t, 2H) | 163 | C 59.16; H 7.76 | C 58.98; H 7.81 |
| | 1635, 1610 | 7.20(m, 3H) | | N 17.25; Cl 10.91 | N 17.32; Cl 10.88 |
| 86 | 3600, 3330 | 2.33(m, 15H), 4.22(t, 2H) | 290, 275, 260 | C$_{15}$H$_{25}$ON$_5$Cl | |
| | 3205, 2940 | 7.21(m, 3H) | 204 | C 49.73; H 6.96 | C 49.71; H 6.94 |
| | 2815, 1620 | | | N 19.33; Cl 19.57 | N 19.42; Cl 19.63 |
| | 1580 | | | | |
| 87 | 3600, 3315 | 1.68(bm, 6H), 2.48(bm, 8H) | 260, 190, 176 | C$_{14}$H$_{21}$ON$_4$Cl | |
| | 3160, 2915 | 4.24(t, 2H), 4.72(bs, 2H) | 162 | C 56.66; H 7.13 | C 56.63; H 7.16 |
| | 1630, 1620 | 7.22(m, 3H) | | N 18.88; Cl 11.94 | N 18.85; Cl 11.98 |
| 88 | 3580, 3410 | 1.58(m, 2H), 2.42(m, 6H) | 277, 191, 177 | C$_{14}$H$_{21}$O$_2$N$_4$Cl | |
| | 3170, 2975 | 3.55(t, 4H), 4.18(t, 2H) | 163 | C 53.76; H 6.77 | C 53.74; H 6.68 |
| | 1600, 1595 | 7.18(m, 3H) | | N 17.91; Cl 11.33 | N 18.03; Cl 11.34 |

EXAMPLE 89

To 60 ml of anhydrous N,N-dimethylformamide were added 4.54 g of 3-phthalimido-4-chloroindazole obtained in the same method as described in Example 1, 4.83 g of 3-bromopropyldiethylamine hydrobromide and 6.3 g of anhydrous potassium for 12 hours at 80° C. After cooling, the mixture was added with 80 ml of water and extracted with diethyl ether. The diethyl ether layer was extracted three times with 2N hydrochloric acid, and the hydrochloric acid layer was washed with diethyl ether. After the pH of the layer was adjusted to 14 with potassium carbonate, the layer was extracted with chloroform. The chloroform layer was dried over anhydrous sodium sulfate and chloroform was removed under reduced pressure to give 3.70 g of 1-(3-diethylaminopropyl)-3-phthalimido-4-chloroindazole having the following analytical values in a yield of 59 %.

IR absorption spectrum ($\nu_{max}$, cm$^{-1}$): 3040, 2960, 1780 and 1615.

NMR spectrum [δ, CDCl$_3$]: 0.96(t, 6H), 2.34(m, 4H), 2.47(q, 4H), 4.25(t, 2H) and 7.18(m, 7H).

Mass spectrum (m/e): 410(M+), 412(M+2), 326(M-84), 312(M-98) and 298(M-112).

To 70 ml of ethyl alcohol was added 3.50 g of the 1-(3-diethylaminopropyl)-3-phthalimido-4-chloroindazole. The mixture was added with 85% hydrazine hydrate under cooling with ice and stirred for 3 hours under cooling with ice. The reaction mixture was filtered and the filtrate was removed under reduced pressure. The residue thus obtained was added with 20 ml of water and extracted with chloroform. The chloroform layer was extracted with 2N hydrochloric acid. The pH of the hydrochloric acid layer was adjusted to 10 with potassium carbonate, and the alkali layer was extracted with chloroform. The chloroform layer was dried over anhydrous sodium sulfate and filtered. The filtrate was removed under reduced pressure to give 2.03 g of 1-(3-diethylaminopropyl)-3-amino-4-chloroindazole having the following analytical values in a yield of 85%.

IR absorption spectrum ($\nu_{max}$, cm$^{-1}$): 3310, 3230, 2940, 2850, 1615 and 1580.

NMR spectrum [δCDCl$_3$]: 0.97(t, 6H), 2.35(m, 4H), 2.48(q, 4H), 4.20(t, 2H), 5.30(bs, 2H), 7.27(s, 2H) and 7.69(s, 1H).

Mass spectrum (m/e): 281(M+), 283(M+2), 252(M-29), 223(M-58), 209(M-72) and 195(M-86).

To 60 ml of anhydrous N,N-dimethylformamide were added 9.2 g of the 1-(3-diethylaminopropyl)-3-amino-4 -chloroindazole, 3-bromopropyldiethylamine hydrobromide and 7.9 g of anhydrous potassium carbonate, and the mixture was stirred for 12 hours at 80° C. After cooling, the mixture was added with 80 ml of water and extracted with diethyl ether. The diethyl ether layer was extracted three times with 2N hydrochloric acid, and the hydrochloric acid layer was washed with diethyl ether. The pH of the layer was adjusted to at least 11 with potassium carbonate and the alkali layer was extracted three times with chloroform. The chloroform layer was dried with anhydrous sodium sulfate, and chloroform was removed under reduced pressure. The residue thus obtained was subjected to an alumina-column chromatography(alumina: 200 g) using chloroform as the developing solvent to give 6.81 g of 1-(3-diethylaminopropyl)-3-(3-diethylaminopropylamino)-4-chloroindazole having the following analytical values in a yield of 53%.

IR absorption spectrum ($\nu_{max}$, cm$^{-1}$): 3300, 3210, 2970, 2810 and 1610.

NMR spectrum [δ, CDCl$_3$]: 0.92(t, 12H), 1.98(m, 4H), 2.51(m, 8H), 4.14(t, 4H), 7.27(s, 2H) and 7.70(s, 1H).

Mass spectrum (m/e) : 393(M+), 395(M+2), 364(M-29), 335(M-58) and 294(M-99).

In 50 ml of absolute ethyl alcohol was dissolved 3.2 g of the 1-(3-diethylaminopropyl)-3-(3-diethylaminopropylamino)-4 -chloroindazole, and into the solution was introduced dried hydrogen chloride gas under cooling with ice. Then to the solution was added anhydrous diethyl ether to separate crystals. The crystals were obtained by filtration and dried to give 1-(3-diethylaminopropyl)-3-diethylaminopropylamino)-4-chloroindazole dihydrochloride having the following analytical value.

Elemental Analysis Value: $C_{21}H_{38}N_5Cl_3$: Calcd.(%): C 54.02; H 8.20; N 15.00; Cl 22.78. Found (%): C 53.98, H 8.18; N 15.13; CZ 22.71.

EXAMPLES 90–92

The same procedures as described in Example 89 were repeated except that 3-aminoindazoles as set forth in Table 26 were employed instead of the 5.66 g of 3-amino-4-chloroindazole. The results including the analytical values are shown in Tables 26 and 27.

extracted three times with chloroform. The chloroform layer was dried over anhydrous sodium sulfate, and chloroform was removed under reduced pressure. The residue thus obtained was subjected to an alumina-column chromatography(alumina: 200 g) using chloroform as the developing solvent to give 6.99 g of 1-(3-diethylaminopropyl)-3-(3-diethylaminopropylamino)indazole having the following analytical values in a yield of 54%.

IR absorption spectrum ($v_{max}$, cm$^{-1}$): 3310, 3200,

TABLE 26

| Example No. | 3-Amino-chloroindazole | (g) | Product | Form | Yield (%) |
|---|---|---|---|---|---|
| 90 | [structure: 4-Cl-indazole-3-NH$_2$] | 5.66 | [structure: product] | Oily Substance | 57 |
| 91 | [structure: 5-Cl-indazole-3-NH$_2$] | 5.66 | [structure: product] | Oily Substance | 58 |
| 92 | [structure: 7-Cl-indazole-3-NH$_2$] | 5.66 | [structure: product] | Oily Substance | 51 |

TABLE 27

| Example No. | IR Spectrum (cm$^{-1}$) | NMR Spectrum ($\delta$, CDCl$_3$) | Mass Spectrum (m/e) | Elemental Analysis Value Calcd. (%) | Found (%) |
|---|---|---|---|---|---|
| 90 | 3310, 3230 | 0.93(t, 12H), 1.96(m, 4H) | 393, 395, 364 | $C_{21}H_{38}N_5Cl_3$ | |
|  | 2980, 2850 | 2.52(m, 8H), 4.20(t, 4H) | 335, 294 | C 54.02; H 8.20 | C 53.87; H 8.17 |
|  | 1615, 1580 | 7.28(s, 2H), 7.69(d, 1H) |  | N 15.00; Cl 22.78 | N 15.21; Cl 22.75 |
| 91 | 3300, 3230 | 0.94(t, 12H), 1.97(m, 4H) | 393, 395, 364 | $C_{21}H_{38}N_5Cl_3$ | |
|  | 2980, 2860 | 2.51(m, 8H), 4.19(t, 4H) | 335, 294 | C 54.02; H 8.20 | C 54.11; H 8.23 |
|  | 1610, 1570 | 6.88(d, 1H), 7.27(s, 1H) 7.68(s, 1H) |  | N 15.00; Cl 22.78 | N 14.83, Cl 22.80 |
| 92 | 3333, 3250 | 0.92(t, 12H), 1.98(m, 4H) | 393, 395, 364 | $C_{21}H_{38}N_5Cl_3$ | |
|  | 2960, 2850 | 2.50(m, 8H), 4.23(t, 4H) | 335, 294 | C 54.02; H 8.20 | C 54.08; H 8.15 |
|  | 1610, 1580 | 7.00(d, 1H), 7.29(d, 1H) 7.63(d, 1H) |  | N 15.00; Cl 22.78 | N 14.88; Cl 22.89 |

EXAMPLE 93

To 60 ml of anhydrous N,N-dimethylformamide were added 8.1 g of 1-(3-diethylaminopropyl)-3-aminoindazole obtained by the same method as described in Example 5, 9.0 g of 3-bromopropyldiethylamine hydrobromide and 7.9 g of anhydrous potassium carbonate. The mixture was stirred for 12 hours at 80° C. After cooling, the mixture was added with 80 ml of water and extracted with diethyl ether. The diethyl ether layer was extracted three times with 2N hydrochloric acid, and the hydrochloric acid layer was washed with diethyl ether. The pH of the layer was adjusted to at least 11 with potassium carbonate, and the alkali layer was 2980, 2800 and 1615.

NMR spectrum [$\delta$, CDCl$_3$]: 0.91(t, 12H), 1.98(m, 4H), 2.52(m, 8H), 4.15(t, 4H) and 7.20(m, 4H).

Mass spectrum (m/e): 393(M$^+$), 395, 364, 335, 294 and 280.

1-(3-Diethylaminopropyl)-3-(3-diethylaminopropylamino)-5-aminoindazole was prepared by the following method as described in R. Adam et al., "Laboratory Experiments in Organic Chemistry" 4th ed., pp.299, 301 and 303, Macmillan, New York, 1949, and S. E. Halet and C. A. Dornfeld, J. Am. Chem. Soc., 75 4334(1935).

In 2.58 ml of sulfuric acid was dissolved 1.7 g of the 1-(3-diethylaminopropyl)-3-(3-diethylaminopropyl-amino)indazole. To the solution were added dropwise 0.41 ml of nitric acid(d =1.42) and 0.41 ml of sulfuric acid (specific gravity 1.84) under cooling with ice. The solution was stirred for 2 hours at 5°-10° C. and added to 12.1 ml of ice and water. The pH of the solution was adjusted to at least 11 with an aqueous ammonia solution, and the solution was extracted with chloroform. The chloroform layer was dried over anhydrous sodium sulfate and chloroform was removed under reduced pressure. The residue thus obtained was dissolved in 50 ml of dried benzene. To the solution were added 10 g of iron powder and 2 ml of hydrochloric acid, and the mixture was stirred for 30 minutes at 80° C. To the mixture was added 0.5 ml of water, and the mixture was stirred for 10 hours at 80° C. After cooling, the mixture was filtered, and the benzene layer was extracted three times with 20 ml of 1N hydrochloric acid. The pH of the hydrochloric acid layer was adjusted to at least 11 with potassium carbonate, and the alkali layer was extracted with chloroform. The chloroform layer was dried over anhydrous sodium sulfate, and chloroform was removed under reduced pressure.

Mass spectrum (m/e): 374, 345, 316, 275 and 261.

In 15 ml of absolute ethyl alcohol was dissolved 0.7 g of the 1-(3-diethylaminopropyl)-3-(3-diethylamino-propylamino)-5-aminoindazole, and into the solution was introduced dried hydrogen chloride gas under cooling with ice. Then to the solution was added anhydrous diethyl ether to separate crystals. The crystals were obtained by filtration and dried to give 1-(3-diethylaminopropyl)-3-(3-diethylaminopropylamino)-5-aminoindazole trihydrochloride having the following analytical value.

Elemental Analysis Value: $C_{21}H_{41}N_6Cl_3$: Calcd.(%): C 52.12; H 8.54; N 17.87; Cl 21.97. Found (%): C 51.98; H 8.67; N 17.43; Cl 21.92.

EXAMPLES 94 AND 95

The same procedures as described in Example 89 were repeated except that 3-amino-5-methoxyindazole and 3-amino-5-methylindazole were employed, respectively, instead of the 5.66 g of 3-amino-4-chloroindazole. 3-Amino-5-methoxyindazole and 3-amino-5-methylindazole were obtained by the same methods as described in Examples 6 and 7, respectively. The results including the analytical values are shown in Tables 28 and 29.

TABLE 28

| Example No. | 3-Aminoindazole | (g) | Product | Form | Yield (%) |
|---|---|---|---|---|---|
| 94 | CH₃O-[indazole]-NH₂ | 5.51 | CH₃O-[indazole with NH(CH₂)₃N(C₂H₅)₂ and (CH₂)₃N(C₂H₅)₂ substituents] | Oily Substance | 47 |
| 95 | CH₃-[indazole]-NH₂ | 4.97 | CH₃-[indazole with NH(CH₂)₃N(C₂H₅)₂ and (CH₂)₃N(C₂H₅)₂ substituents] | Oily Substance | 49 |

TABLE 29

| Example No. | IR Spectrum (cm⁻¹) | NMR Spectrum (δ, CDCl₃) | Mass Spectrum (m/e) | Elemental Analysis Value Calcd. (%) | Found (%) |
|---|---|---|---|---|---|
| 94 | 3340, 3190 2980, 2870 1620, 1580 | 0.93(t, 12H), 1.98(m, 4H) 2.51(m, 8H), 3.80(s, 3H) 4.15(t, 4H), 7.13(m, 3H) | 373, 344, 386 187 | $C_{22}H_{41}ON_5Cl_2$ C 57.13; H 8.94 N 15.14; Cl 15.38 | C 57.21 H 8.95 N 15.01; Cl 15.30 |
| 95 | 3320, 3210 2980, 2880 1625, 1575 | 0.95(t, 12H), 1.96(m, 4H) 2.33(s, 3H), 2.50(m, 8H) 4.20(t, 4H), 7.09(s, 2H) 7.42(s, 1H) | 357, 328, 270 171 | $C_{22}H_{41}N_5Cl_2$ C 59.18; H 9.25 N 15.69; Cl 15.88 | C 59.01; H 9.21 N 15.81; Cl 15.97 |

The residue thus obtained was subjected to an alumina-column chromatography(alumina: 100 g) using chloroform as the developing solvent to give 0.87 g of 1-(3-diethylaminopropyl)-3-(3-diethylaminopropylamino)-5-aminoindazole having the following analytical values in a yield of 49%.

IR absorption spectrum ($\delta_{max}$, cm⁻¹): 3400, 3250, 2950, 2890, 1610 and 1580.

NMR spectrum [, CD₃OD]: 0.93(t, 12H), 1.97(m, 4H), 2.52(m, 8H), 4.20(t, 4H) and 7.17(m, 3H).

EXAMPLES 96–99

The same procedures as described in Example 89 were repeated that 5.66 g of 3-amino-5-chloroindazole and an ω-halogenoalkylamine hydrobromide as set forth in Table 30 were employed instead of the 5.66 g of 3-amino-4-chloroindazole and the 9.0 g of 3-bromo-propyldiethylamine hydrobromide, respectively. The results including the analytical values are shown in Tables 30 and 31.

chloroindazole, respectively. As a result, 1-(3-piperidinopropyl)-3-amino-5-chloroindazole was ob-

TABLE 30

| Example No. | ω-Halogenoalkylamine Hydrobromide | (g) | Product | Form | Yield (%) |
|---|---|---|---|---|---|
| 96 | piperidine-N—(CH$_2$)$_3$Br·HBr | 9.30 | 5-Cl-indazole with 3-NH(CH$_2$)$_3$N(piperidine), 1-(CH$_2$)$_3$N(C$_2$H$_5$)$_2$ | Oily Substance | 53 |
| 97 | piperidine-N—(CH$_2$)$_6$Br·HBr | 10.68 | 5-Cl-indazole with 3-NH(CH$_2$)$_6$N(piperidine), 1-(CH$_2$)$_3$N(C$_2$H$_5$)$_2$ | Oily Substance | 46 |
| 98 | (C$_4$H$_9$)$_2$N—(CH$_2$)$_3$Br·HBr | 10.70 | 5-Cl-indazole with 3-NH(CH$_2$)$_3$N(C$_4$H$_9$)$_2$, 1-(CH$_2$)$_3$N(C$_2$H$_5$)$_2$ | Oily Substance | 56 |
| 99 | piperidine-N—CH(CH$_3$)CH$_2$CH$_2$Br·HBr | 9.74 | 5-Cl-indazole with 3-NHCH$_2$CH$_2$CH(CH$_3$)N(piperidine), 1-(CH$_2$)$_3$N(C$_2$H$_5$)$_2$ | Oily Substance | 54 |

TABLE 31

| Example No. | IR Spectrum (cm$^{-1}$) | NMR Spectrum (δ, CDCl$_3$) | Mass Spectrum (m/e) | Elemental Analysis Value Calcd. (%) | Found (%) |
|---|---|---|---|---|---|
| 96 | 3310, 3210 2970, 2820 1620 | 0.96(t, 6H), 1.51(m, 8H) 2.30(m, 8H), 2.47(q, 4H) 4.20(t, 2H), 7.27(s, 2H) 7.70(s, 1H) | 406, 408, 377 348, 292 | C$_{22}$H$_{38}$N$_5$Cl$_3$ C 55.17; H 8.00 N 14.62; Cl 22.21 | C 55.21; H 7.87 N 14.57; Cl 22.35 |
| 97 | 3320, 3200 2970, 2810 1615 | 0.98(t, 6H), 1.88(bm, 14H) 2.32(m, 10H), 2.49(q, 4H) 2.19(t, 2H), 7.26(s, 2H) 7.69(s, 1H) | 448, 450, 419 390, 334 | C$_{25}$H$_{44}$N$_5$Cl$_3$ C 57.63; H 8.51 N 13.44; Cl 20.42 | C 57.47; H 8.63 N 13.49; Cl 20.41 |
| 98 | 3320, 3210 2960, 2820 1615 | 0.95(m, 12H), 1.28(m, 10H) 2.30(m, 10H), 2.47(q, 4H) 4.11(t, 4H), 7.27(s, 2H) 7.68(s, 1H) | 450, 452, 421 392, 336 | C$_{25}$H$_{46}$N$_5$Cl$_3$ C 57.41; H 8.87 N 13.89; Cl 20.33 | C 57.39; H 8.93 N 13.21; Cl 20.47 |
| 99 | 3310, 3210 2970, 2810 1610 | 0.91(m, 9H), 1.40(m, 8H) 2.30(m, 9H), 2.48(q, 4H) 4.28(t, 4H), 7.29(s, 2H) 7.69(s, 1H) | 420, 422, 391 362, 306 | C$_{23}$H$_{40}$N$_5$Cl$_3$ C 56.04; H 8.18 N 14.20; Cl 21.58 | C 55.98; H 8.25 N 14.23; Cl 21.54 |

EXAMPLE 100

The same procedures for preparing 1-(3-diethylaminopropyl)-3-amino-4-chloroindazole as described in Example 89 were repeated except that 3-bromopropylpiperidine hydrobromide and 3-amino-5-chloroindazole were employed instead of the 3-bromopropyldiethylamine hydrobromide and the 3-amino-4-chloroindazole, respectively. As a result, 1-(3-piperidinopropyl)-3-amino-5-chloroindazole was obtained.

To 60 ml of anhydrous N,N-dimethylformamide were added 9.59 g of 1-(3-piperidinopropyl)-3-amino-5-chloroindazole, 8.98 g of 3-bromopropyldiethylamine hydrobromide and 7.89 g of anhydrous potassium carbonate, and the mixture was stirred for 12 hours at 80°

C. After cooling, the mixture was added with 80 ml of water and extracted with diethyl ether. The diethyl ether layer was extracted three times with 2N hydrochloric acid, and the hydrochloric acid layer was washed with diethyl ether. The pH of the layer was adjusted to at least 11 with potassium carbonate, and the alkali layer was extracted three times with chloroform. The chloroform layer was dried over anhydrous sodium sulfate, and chloroform was removed under reduced pressure. The residue thus obtained was subjected to an alumina-column chromatography (alumina: 200 g) using chloroform as the developing solvent to give 7.18 g of 1-(3-piperidinopropyl)-3-(3-diethylaminopropylamino)-5-chloroindazole having the following analytical values in a yield of 54%.

IR absorption spectrum (νhd max, cm$^{-1}$): 3310, 3220, 2970, 2830 and 1610.

NMR spectrum [δCDCl$_3$]: 0.96(t, 6H), 1.48(m, 8H), 2.33(m, 10H), 2.42(q, 4H), 4.20(t, 4H), 7.28(s, 2H) and propylamino)-5-chloroindazole, and into the solution was introduced dried hydrogen chloride gas under cooling with ice. Then to the solution was added anhydrous diethyl ether to separate crystals. The crystals were obtained by filtration and dried to give 1-(3-piperidinopropyl)-3-(3-diethylaminopropylamino)-5-chloroindazole dihydrochloride having the following analytical value.

Elemental Analysis Value: $C_{22}H_{38}N_5Cl_3$: Calcd.(%): C 55.17; H 8.00; N 14.62; Cl 22.21. Found (%): C 55.20; H 7.92, N 14.64; Cl 22.24.

EXAMPLES 101–103

The same procedures as described in Example 100 were repeated except that ω-halogenoalkylamine hydrobromides as set forth in Table 32 were employed instead of the 8.98 g of 3-bromopropyldiethylamine hydrobromide. The results including the analytical values are shown in Tables 32 and 33.

TABLE 32

| Example No. | ω-Halogenoalkylamine Hydrobromide | (g) | Product | Form | Yield (%) |
|---|---|---|---|---|---|
| 101 | piperidine-N—(CH$_2$)$_3$Br·HBr | 9.30 | 5-Cl-indazole with NH(CH$_2$)$_3$N-piperidine and N-(CH$_2$)$_3$N-piperidine | Oily Substance | 58 |
| 102 | piperidine-N—(CH$_2$)$_6$Br·HBr | 10.63 | 5-Cl-indazole with NH(CH$_2$)$_6$N-piperidine and N-(CH$_2$)$_3$N-piperidine | Oily Substance | 48 |
| 103 | piperidine-N—CH(CH$_3$)CH$_2$CH$_2$Br·HBr | 9.74 | 5-Cl-indazole with NHCH$_2$CH$_2$CH(CH$_3$)N-piperidine and N-(CH$_2$)$_3$N-piperidine | Oily Substance | 50 |

TABLE 33

| Example No. | IR Spectrum (cm$^{-1}$) | NMR Spectrum (δ, CDCl$_3$) | Mass Spectrum (m/e) | Elemental Analysis Value Calcd. (%) | Found (%) |
|---|---|---|---|---|---|
| 101 | 3320, 3210 2970, 2830 1620 | 1.56(m, 16H), 2.20(m, 12H) 4.20(t, 4H), 7.29(s, 2H) 7.69(s, 1H) | 418, 420, 404 390, 376 | $C_{23}H_{38}N_5Cl_3$ C 56.27; H 7.80 N 14.26; Cl 21.67 | C 56.57; H 7.50 N 14.56; Cl 21.37 |
| 102 | 3310, 3210 2980, 2830 1615 | 1.41(m, 20H), 2.30(m, 14H) 4.19(t, 4H), 7.28(s, 2H) 7.68(s, 1H) | 460, 462, 446 418, 404, 390 | $C_{26}H_{44}N_5Cl_3$ C 58.59; H 8.32 N 13.14; Cl 19.95 | C 58.29; H 8.02 N 13.44; Cl 20.25 |
| 103 | 3310, 3200 2980, 2320 1630 | 0.88(d, 3H), 1.40(m, 14H) 2.20(m, 18H), 4.23(t, 4H) 7.27(s, 2H), 7.67(s, 1H) | 432, 434, 418 404, 390, 376 | $C_{24}H_{40}H_5Cl_3$ C 57.09; H 7.98 N 13.87; Cl 21.06 | C 57.39; H 8.28 N 13.57; Cl 20.76 |

7.68(s, 1H).

Mass spectrum (m/e): 409(M$^+$), 411, 377, 348, 292 and 208.

In 50 ml of absolute ethyl alcohol was dissolved 3.2 g of the 1-(3-piperidinopropyl)-3-(3-diethylamino-

EXAMPLE 104

The same procedures for preparing 1-(3-piperidinopropyl)-3-amino-5-chloroindazole as described in Example 100 were repeated except that 1-(1-methyl-3-bromopropyl)piperidine was employed instead of the 3-bromopropylpiperidine. As a result, 1-(3-piperidinobutyl)-3-amino-5-chloroindazole was obtained.

To 60 ml of anhydrous N,N-dimethylformamide were added 9.90 g of the 1-(3-piperidinobutyl)-3-amino-5-chloroindazole, 8.98 g of 3-bromopropyldieth hydrobromide and 7.89 g of anhydrous potassium carbonate, and the mixture was stirred for 12 hours at 180° C. After cooling, the mixture was added with 80 ml of water and extracted with diethyl ether. The diethyl ether layer was extracted three times with 2N hydrochloric acid, and the hydrochloric acid layer was washed with diethyl ether. The pH of the layer was adjusted to at least 11 with potassium carbonate, and the alkali layer was extracted three times with chloroform. The chloroform layer was dried with anhydrous sodium sulfate, and chloroform was removed under reduced pressure. The residue thus obtained was subjected to an alumina-column chromatography (alumina: 200 g) using chloroform as the developing solvent to give 6.90 g of 1-(3-piperidinobutyl)-3-(3-diaminopropylamino)-5-chloroindazole having the following analytical values in a yield of 51%.

IR absorption spectrum ($\delta_{max}$, cm$^{-1}$): 3320, 3200, 2970, 2820 and 1610.

NMR spectrum [, CDCl$_3$]: 0.88(m, 9H), 1.41(m, 8H), 2.30(m, 9H), 247(q, 4H), 4.20(t, 2H), 7.27(s, 2H) and 7.69(s, 1H).

Mass spectrum (m/e): 420, 422, 391, 362, 306 and 222.

In 50 ml of absolute ethyl alcohol was dissolved 3.2 g of the 1-(3-piperidinobutyl)-3-(3-diethylaminopropylamino)-5-chloroindazole, and into the solution was introduced dried hydrogen chloride under cooling with ice. Then to the solution was added anhydrous diethyl ether to separate crystals. The crystals were obtained by filtration and dried to give 1-(3-piperidinobutyl)-3-(3-diethylaminopropylamino)-5-chloroindazole dihydrochloride having the following analytical value.

Elemental Analysis Value: C$_{23}$H$_{40}$N$_5$Cl$_3$: Calcd.(%): C 56.03; H 8.18; N 14.21; Cl 21.58. Found (%): C 56.11; H 8.01; N 14.15; Cl 21.73.

EXAMPLES 105–107

The same procedures as described in Example 104 were repeated except that ω-halogenoalkylamine hydrobromides as set forth in Table 34 were employed instead of the 8.98 g of 3-bromopropyldiethylamine hydrobromide. The results including the analytical values are shown in Tables 34 and 35.

TABLE 34

| Example No. | ω-Halogenoalkylamine Hydrobromide | (g) | Product | Form | Yield (%) |
|---|---|---|---|---|---|
| 105 | 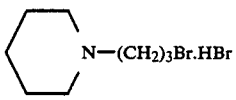 | 9.30 | 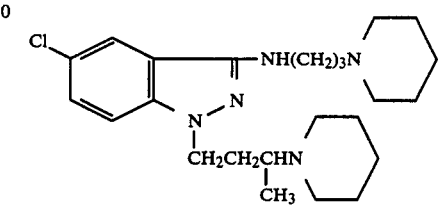 | Oily Substance | 47 |
| 106 | 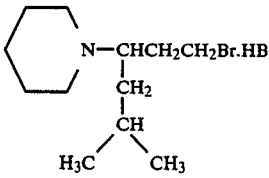 | 11.11 | 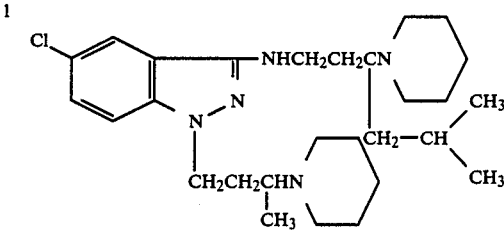 | Oily Substance | 50 |
| 107 | 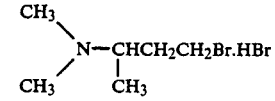 | 8.46 | 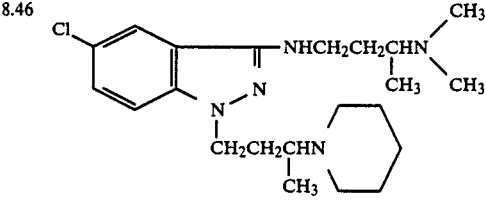 | Oily Substance | 44 |

TABLE 35

| Example No. | IR Spectrum (cm$^{-1}$) | NMR Spectrum (δ, CDCl$_3$) | Mass Spectrum (m/e) | Elemental Analysis Value Calcd. (%) | Found (%) |
|---|---|---|---|---|---|
| 105 | 3320, 3210 2970, 2820 1620 | 0.90(d, 3H), 1.41(m, 14H) 2.22(m, 13H), 4.21(t, 4H) 7.28(s, 2H), 7.68(s, 1H) | 432, 434, 418 404, 390 | C$_{24}$H$_{40}$N$_5$Cl$_3$ C 57.09; H 7.98 N 13.87; Cl 21.06 | C 57.39; H 7.68 N 13.57; Cl 21.36 |
| 106 | 3300, 3200 2970, 2850 | 0.92(m, 9H), 1.49(m, 19H) 2.24(m, 10H), 4.30(t, 4H) | 488, 490, 474 458, 443 | C$_{28}$H$_{48}$N$_5$Cl$_3$ C 59.94; H 8.62 | C 59.64; H 8.92 |

TABLE 35-continued

| Example No. | IR Spectrum (cm$^{-1}$) | NMR Spectrum ($\delta$, CDCl$_3$) | Mass Spectrum (m/e) | Elemental Analysis Value | |
|---|---|---|---|---|---|
| | | | | Calcd. (%) | Found (%) |
| 107 | 1610 3330, 3210 | 7.27(s, 2H), 7.70(s, 1H) 0.92(m, 6H), 1.82(m, 10H) | 406, 408, 391 | N 12.48; Cl 18.96 $C_{22}H_{38}N_5Cl_3$ | N 12.78; Cl 18.66 |
| | 2960, 2850 1610 | 2.30(m, 12H), 4.20(t, 4H) 7.28(s, 2H), 7.68(s, 1H) | 376, 361, 277 | C 55.17; H 8.00 N 14.62; Cl 22.21 | C 55.47; H 8.30 N 14.32; Cl 21.91 |

EXAMPLE 108

The same procedures for preparing 1-(3-diethylaminopropyl)-3-amino-4-chloroindazole as described in Example 89 were repeated except that 1-(1-methyl-3-bromopropyl)-dimethylamine hydrobromide and 3-amino-5-chloroindazole were employed instead of the 3-bromopropyldiethylamine hydrobromide and the 3-amino-4-chloroindazole, respectively. As a result, 1-(3-dimethylaminobutyl)-3-amino-5-chloroindazole was obtained.

To 60 ml of anhydrous N,N-dimethylformamide were added 8.71 g of the 1-(3-dimethylaminobutyl)-3-amino-5-chloroindazole, 8.98 g of 3-bromopropyldiethylamine hydrobromide and 7.89 g of anhydrous potassium carbonate, and the mixture was atirred for 12 hours at 80° C. After cooling, the mixture was added with 80 ml of water and extracted with diethyl ether. The diethyl ether layer was extracted three times with 2N hydrochloric acid, and the hydrochloric acid layer was washed with diethyl ether. The pH of the layer was adjusted to at least 11 with potassium carbonate, and the alkali layer was extracted three times with chloroform. The chloroform layer was dried over anhydrous sodium sulfate, and chloroform was removed under reduced pressure. The residue thus obtained was subjected to an alumina-column chromatography (alumina: 200 g) using chloroform as the developing solvent to give 7.23 g of 1-(3-dimethylaminobutyl)-3-(3-diethylaminopropylamino)-5-chloroindazole having the following analytical values in a yield of 58%.

IR absorption spectrum ($\nu_{max}$, cm$^{-1}$): 3320, 3200, 2960, 2820 and 1620.

NMR spectrum [$\delta$, CDCl$_3$]: 0.96(m, 9H), 2.30(m, 13H), 2.46(q, 4H), 4.20(t, 4H), 7.27(s, 2H) and 7.67(s, 1H).

Mass spectrum (m/e): 380, 382, 322 and 308.

In 50 ml of absolute ethyl alcohol was dissolved 3.10 g of the 1-(3-dimethylaminobutyl)-3-(3-diethylaminopropylamino)-5-chloroindazole, and into the solution was introduced dried hydrogen chloride gas under cooling with ice. Then to the solution was added anhydrous diethyl ether to separate crystals. The crystals were obtained by filtration and dried to give 1-(3-dimethylaminobutyl)-3-(3-diethylaminopropylamino)5-chloroindazole dihydrochloric acid having the following analytical value.

Elemental Analysis Value: $C_{20}H_{36}N_5Cl_3$: Calcd.(%): C 53.04; H 8.01; N 15.46; Cl 23.49. Found (%): C 52.96; H 7.99; N 15.58; Cl 23.47.

EXAMPLES 109-111

The same procedures as described in Example 108 were repeated except that $\omega$-halogenoalkylamine hydrobromides as set forth in Table 36 were employed instead of the 8.98 g of 3-bromopropyldiethylamine hydrobromide. The results including the analytical values are shown in Tables 36 and 37.

TABLE 36

| Example No. | $\omega$-Halogenoalkylamine Hydrobromide | (g) | Product | Form | Yield (%) |
|---|---|---|---|---|---|
| 109 | ⟨N⟩—(CH$_2$)$_3$Br·HBr | 9.30 | Cl-indazole-NH(CH$_2$)$_3$N⟨⟩ with N-CH$_2$CH$_2$CHN(CH$_3$)$_2$ with CH$_3$ | Oily Substance | 43 |
| 110 | ⟨N⟩—CHCH$_2$CH$_2$Br·HBr with CH$_3$ | 9.74 | Cl-indazole-NHCH$_2$CH$_2$CHN⟨⟩ with CH$_3$; N-CH$_2$CH$_2$CHN(CH$_3$)$_2$ with CH$_3$ | Oily Substance | 47 |

TABLE 36-continued

| Example No. | ω-Halogenoalkylamine Hydrobromide | (g) | Product | Form | Yield (%) |
|---|---|---|---|---|---|
| 111 | $C_2H_5$<br>    \<br>     N—CH—$CH_2CH_2Br$·HBr<br>    /    \|<br>$C_2H_5$   $CH_2$  $CH_3$<br>         \|<br>         CH<br>          \<br>           $CH_3$ | 10.73 | Cl—[indazole]—$NHCH_2CH_2CHN(C_2H_5)_2$ with $CH_2CH(CH_3)_2$ substituent and $N$-$CH_2CH_2CHN(CH_3)_2$ with $CH_3$ branch | Oily Substance | 41 |

TABLE 37

| Example No. | IR Spectrum (cm$^{-1}$) | NMR Spectrum (δ, $CDCl_3$) | Mass Spectrum (m/e) | Elemental Analysis Value | |
|---|---|---|---|---|---|
| | | | | Calcd. (%) | Found (%) |
| 109 | 3340, 3210 | 0.90(d, H), 1.59(m, 10H) | 392, 394, 377 | $C_{21}H_{36}N_5Cl_3$ | |
| | 2980, 2850<br>1620 | 2.25(m, 18H), 4.19(t, 4H)<br>7.27(s, 2H), 7.70(s, 1H) | 362, 348 | C 54.25; H 7.81<br>N 15.06; Cl 22.88 | C 54.55; H 7.51<br>N 15.36; Cl 22.58 |
| 110 | 3310, 3240 | 0.92(m, 6H), 1.56(m, 10H) | 406, 408, 391 | $C_{22}H_{38}N_5Cl_3$ | |
| | 2790, 2840<br>1620 | 2.34(m, 12H), 4.21(t, 4H)<br>7.28(s, 2H), 7.68(s, 1H) | 376, 362 | C 55.17; H 8.00<br>N 14.62; Cl 22.21 | C 55.47; H 7.70<br>N 14.92; Cl 21.91 |
| 111 | 3320, 3210 | 0.94(m, 15H), 1.51(m, 7H) | 436, 438, 421 | $C_{24}H_{44}N_5Cl_3$ | |
| | 2970, 2840<br>1620 | 2.24(m, 12H), 4.21 (t, 2H)<br>7.27(s, 2H), 7.69(s, 1H) | 406, 392 | C 56.68; H 8.71<br>N 13.76; Cl 20.90 | C 56.33; H 9.01<br>N 14.06; Cl 20.60 |

EXAMPLE 112

The same procedures for preparing 1-(3-diethylaminopropyl)-3-amino-4-chloroindazole as described in Example 89 were repeated except that 4.78 g of 3-bromopropylpyrrolidine hydrobromide and 5.66 g of 3-amino-5-chloroindazole were employed instead of the 3-bromopropyldiethylamine hydrobromide and the 3-amino-4-chloroindazole, respectively. As a result, 4.98 g of 1-(3-pyrrolidinopropyl)-3-amino-5-chloroindazole was obtained.

To 60 ml of anhydrous N,N-dimethylformamide were added 9.12 g of the 1-(3-pyrrolidinopropyl)-3-amino-5-chloroindazole, 9.94 g of 3-bromopropylhomopiperidine hydrobromide and 7.89 g of anhydrous potassium carbonate, and the mixture was stirred for 12 hours at 80° C. After cooling, the mixture was added with 80 ml of water and extracted with diethyl ether. The diethyl ether layer was extracted three times with 2N hydrochloric acid, and the hydrochloric acid layer was washed with diethyl ether. The pH of the layer was adjusted to at least 11 with potassium carbonate, and the alkali layer was extracted three times with chloroform. The chloroform layer was dried over anhydrous sodium sulfate, and chloroform was removed under reduced pressure. The residue thus obtained was subjected to an alumina-column chromatography(alumina: 200 g) using chloroform as the developing solvent to give 6.84 g of 1-(3-pyrrolidinopropyl)-3-(3-homopiperidinopropylamino)-5-chloroindazole having the following analytical values in a yield of 53%.

IR absorption spectrum ($\nu_{max}$, cm$^{-1}$): 3310, 3240, 2980, 2870 and 1620.

NMR spectrum [δ, $CDCl_3$]: 1.61(m, 14H), 2.13(bs, 2H), 2.51(m, 12H), 4.19(t, 4H), 7.27(s, 2H), 7.70(s, 1H).

Mass spectrum (m/e): 417(M+), 419(M+2), 347(M-70), 333(M-84), 319(M-98) and 305(M-112).

In 50 ml of absolute ethyl alcohol was dissolved 3.0 g of the 1-(3-pyrrolidinopropyl)-3-(3-homopiperidinopropylamino)-5-chloroindazole, and into the solution was introduced dried hydrogen chloride gas under cooling with ice. Then to the solution was added anhydrous diethyl ether to separate crystals. The crystals were obtained by filtration and dried to give 1-(3-pyrrolidinopropyl)-3-(3-homopiperidinopropylamino)-5-chloroindazole dihydrochloride having the following analytical value.

Elemental Analysis Value: $C_{23}H_{38}N_5Cl_3$: Calcd.(%): C 56.27; H 7.80; N 14.27; Cl 21.66. Found (%): C 56.31; H 7.83; N 14.09; Cl 21.77.

EXAMPLES 113 AND 114

The same procedures as described in Example 112 were repeated except that ω-halogenoalkylamine hydrobromides as set forth in Table 38 were employed instead of the 3-bromopropylhomopiperidine hydrobromide. The results including the analytical values are shown in Tables 38 and 39.

TABLE 38

| Example No. | ω-Halogenoalkylamine Hydrobromide | (g) | Product | Form | Yield (%) |
|---|---|---|---|---|---|
| 113 | 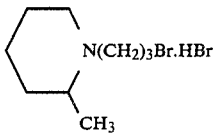 | 9.94 | 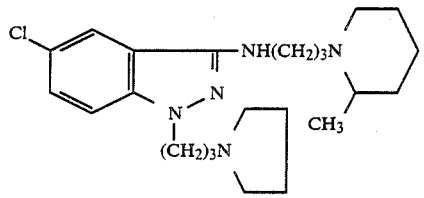 | Oily Substance | 49 |
| 114 | 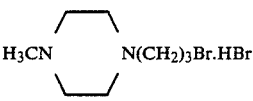 | 9.97 | 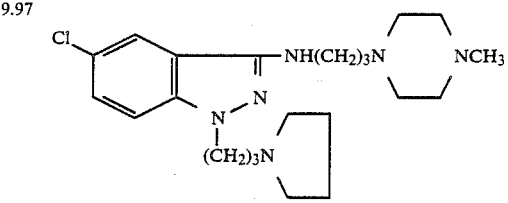 | Oily Substance | 51 |

TABLE 39

| Example No. | IR Spectrum (cm$^{-1}$) | NMR Spectrum (δ, CDCl$_3$) | Mass Spectrum (m/e) | Elemental Analysis Value | |
|---|---|---|---|---|---|
| | | | | Calcd. (%) | Found (%) |
| 113 | 3300, 3200 2990, 2880 1620 | 1.00(d, 3H), 1.65(m, 14H) 2.43(m, 6H), 2.74(m, 5H) 4.21(t, 4H), 7.22(m, 3H) | 417, 419, 347 333, 319, 305 | C$_{23}$H$_{38}$N$_5$Cl$_3$ C 56.27; H 7.81 N 14.26; Cl 21.66 | C 56.30; H 7.84 N 14.23; Cl 21.63 |
| 114 | 3300, 3215 2975, 2870 1615 | 1.71(m, 6H), 2.50(m, 21H) 4.21(t, 4H), 7.21(m, 3H) | 418, 420, 348 334, 320, 306 | C$_{22}$H$_{37}$N$_6$Cl$_3$ C 53.72; H 7.58 N 17.08; Cl 21.62 | C 53.75; H 7.55 N 17.05; Cl 21.65 |

EXAMPLE 115

The same procedures for preparing 1-(3-diethylaminopropyl)-3-amino-4-chloroindazole as described in Example 89 were repeated except that 5.03 g of 3-bromopropylmorpholine hydrobromide and 5.66 g of 3-amino-5-chloroindazole were employed instead of the 3-bromopropyldiethylamine hydrobromide and the 3-amino-4-chloroindazole, respectively. As a result, 5.68 g of 1-(3-morpholinopropyl)-3-amino-5-chloroindazole was obtained.

To 60 ml of anhydrous N,N-dimethylformamide were added 9.63 g of the 1-(3-morpholinopropyl)-3-amino-5-chloroindazole, 8.98 g of 3-bromopropyldiethylamine hydrobromide and 7.89 g of anhydrous potassium carbonate, and the mixture was stirred for 12 hours at 80° C. After cooling, the mixture was added with 80 ml of water and extracted with diethyl ether. The diethyl ether layer was extracted three times with 2N hydrochloric acid, and the hydrochloric acid layer was washed with diethyl ether. The pH of the layer was adjusted to at least 11 with potassium carbonate, and the alkali layer was extracted three times with chloroform. The chloroform layer was dried over anhydrous sodium sulfate, and chloroform was removed under reduced pressure. The residue thus obtained was subjected to an alumina-column chromatography (alumina: 200 g) using chloroform as the developing solvent to give 7.87 g of 1-(3-morpholinopropyl)-3-(3-diethylaminopropylamino)-5-chloroindazole having the following analytical values in a yield of 59%.

IR absorption spectrum ($\omega_{max}$, cm$^{-1}$): 3400, 3230, 2960, 2980 and 1625.

NMR spectrum [δ, CDCl$_3$]: 0.98(t, 6H), 1.59(m, 2H), 2.43(m, 14H), 3.58(5, 4H), 4.24(t, 4H), 7.28(s, 2H) and 7.68(s, 1H).

Mass spectrum (m/e): 407, 409, 335, 321, 307 and 293.

In 50 ml of absolute ethyl alcohol was dissolved 3.2 g of the 1-(3-morpholinopropyl)-3-(3-diethylaminopropylamino)-5-chloroindazole, and into the solution was introduced dried hydrogen chloride gas under cooling with ice. Then to the solution was added anhydrous diethyl ether to separate crystals. The crystals were obtained by filtration and dried to give 1-(3-morpholinopropyl)-3-(3-diethylaminopropylamino)-5-chloroindazole dihydrochloride having the following analytical value.

Elemental Analysis Value: C$_{21}$H$_{36}$ON$_5$Cl$_3$ Calcd.(%): C 52.45; H 7.55; N 14.56; Cl 22.12. Found (%) C 52.49; H 7.49; N 14.51; Cl 22.11.

EXAMPLES 116–118

The same procedures as described in Example 115 were repeated except that ω-halogenoalkylamine hydrobromides as set forth in Table 40 were employed instead of the 8.98 g of 3-bromopropyldiethylamine hydrobromide. The results including the analytical values are shown in Tables 40 and 41.

TABLE 40

| Example No. | ω-Halogenoalkylamine Hydrobromide | (g) | Product | Form | Yield (%) |
|---|---|---|---|---|---|
| 116 | [structure: 2,6-dimethylpiperidine-N—(CH₂)₃Br·HBr] | 10.26 | [structure: 5-chloro-indazole with NH(CH₂)₃—N(2,6-dimethylpiperidine) and N(CH₂)₃N(morpholine)] | Oily Substance | 47 |
| 117 | [structure: 4-chloropiperidine-N—(CH₂)₃Br·HBr] | 10.46 | [structure: 5-chloro-indazole with NH(CH₂)₃—N(4-chloropiperidine) and N(CH₂)₃N(morpholine)] | Oily Substance | 50 |
| 118 | [structure: 4-hydroxypiperidine-N—(CH₂)₃Br·HBr] | 9.86 | [structure: 5-chloro-indazole with NH(CH₂)₃—N(4-hydroxypiperidine) and N(CH₂)₃N(morpholine)] | Oily Substance | 44 |

TABLE 41

| Example No. | IR Spectrum (cm⁻¹) | NMR Spectrum (δ, CDCl₃) | Mass Spectrum (m/e) | Elemental Analysis Value | |
|---|---|---|---|---|---|
| | | | | Calcd. (%) | Found (%) |
| 116 | 3400, 3210 2980, 1620 1590 | 1.21(d, 6H), 1.38(m, 6H) 1.59(m, 2H), 2.38(m, 8H) 2.79(m, 2H), 3.57(t, 4H) 3.81(t, 2H), 4.20(t, 4H) 7.27(s, 2H), 7.67(s, 1H) | 448, 450, 376 362, 348, 334 | $C_{24}H_{40}ON_5Cl_3$ C 55.33; H 7.74 N 13.44; Cl 20.42 | C 55.03; H 8.04 N 13.14; Cl 20.72 |
| 117 | 3380, 3210 2970, 1630 1570 | 1.55(m, 6H), 2.19(m, 9H) 2.94(m, 6H), 3.56(t, 4H) 4.20(t, 4H), 7.23(s, 2H) 7.70(s, 1H) | 454, 456, 382 368, 354, 340 | $C_{22}H_{35}ON_5Cl_4$ C 50.11; H 6.69 N 13.28; Cl 26.89 | C 50.41; H 6.39 N 13.58; Cl 26.59 |
| 118 | 3410, 3250 2980, 1620 1580 | 1.54(m, 6H), 2.21(m, 9H) 2.97(m, 6H), 3.58(t, 4H) 4.21(t, 4H), 7.26(s, 2H) 7.69(s, 1H) | 436, 438, 364 350, 336, 322 | $C_{22}H_{36}O_2N_5Cl_3$ C 51.19; H 7.13 N 13.76; Cl 20.90 | C 51.49; H 7.43 N 13.46; Cl 20.60 |

EXAMPLE 119

To 60 ml of anhydrous N,N-dimethylformamide were added 9.2 g of 1-(3-diethylaminopropyl)-3-amino-4-chloroindazole prepared by the same method as described in Example 1, 9.0 g of 3-bromopropyldiethylamine hydrobromide and 7.9 g of anhydrous potassium carbonate. The mixture was stirred for 12 hours at 80° C. After cooling, the mixture was added with 80 ml of water and extracted with diethyl ether. The diethyl ether layer was extracted three times with 2N hydrochloric acid, and the hydrochloric acid layer was washed with diethyl ether. The pH of the layer was adjusted to at least 11 with potassium carbonate, and the alkali layer was extracted three times with chloroform. The chloroform layer was dried over anhydrous sodium sulfate, and chloroform was removed under reduced pressure. The residue thus obtained was subjected to an alumina-column chromatography (alumina: 200 g) using chloroform as the developing solvent to give 6.81 g of 1-(3-diethylaminopropyl)-3-(3-diethylaminopropylamino)-4-chloroindazole having the following analytical values in a yield of 53%.

IR absorption spectrum ($\nu_{max}$, cm⁻¹): 3300, 3210, 2970, 2810 and 1610.

NMR spectrum [δ, CDCl₃]: 0.92(t, 12H), 1.98(m, 4H), 2.51(m, 8H), 4.14(t, 4H), 7.27(s, 2H) and 7.70(s, 1H).

Mass spectrum (m/e): 393(M+), 395(M+2), 364(M-29), 335(M-58) and 294(M-99).

To 20 ml of diethyl ether containing 600 mg of magnesium powder was added dropwise a mixed solution consisting of 3.92 g of the 1-(3-diethylaminopropyl)-3-(3-diethylaminopropylamino)-4-chloroindazole, 2.0 g of isopropyl bromide and 20 ml of diethyl ether. Into the mixed solution were introduced dried oxygen gas and dried carbon dioxide gas for 12 hours so as to reflux the solution, and the solution was left to stand for 12 hours. The pH of the solution was adjusted to 4.0 by adding dropwise sulfuric acid to the solution at 0° C. The solution was added with 50 ml of water and filtered. To the aqueous layer of the filtrate was added an aqueous potassium carbonate solution to separate crystals. The crystals were obtained by filtration and dried to give 1.46 g of 1-(3-diethylaminopropyl)-3-(3-diethylaminopropylamino)-4-hydroxyindazole having the following analytical values in a yield of 39%.

IR absorption spectrum ($\nu_{max}$, cm$^{-1}$): 3590, 3310, 3210, 2960, 2820 and 1620.

NMR spectrum [$\delta$, CD$_3$OD]: 0.93(t, 12H), 1.97(m, 4H), 2.5l(m, 8H), 4.15(t, 4H) and 7.17(m, 3H).

Mass spectrum (m/e): 375(M$^+$), 346(M-29), 317(M-58) and 276(M-99).

In 50 ml of absolute ethyl alcohol was dissolved 3.1 g of the 1-(3-diethylaminopropyl)-3-(3-diethylaminopropylamino)-4-hydroxyindazole, and into the solution was introduced dried hydrogen chloride gas under cooling with ice. Then to the solution was added anhydrous diethyl ether to separate crystals. The crystals were obtained by filtration and dried to give 1-(3-diethylaminopropyl)-3-(3-diethylaminopropylamino)-4-hydroxyindazole dihydrochloride having the following analytical value.

Elemental Analysis Value: C$_{21}$H$_{39}$ON$_5$Cl$_2$: Calcd.(%): C 56.24; H 8.77; N 15.62; Cl 15.81. Found (%): C 56.13; H 8.72; N 15.68; Cl 15.93.

EXAMPLE 120

The same procedures as described in Example 89 were repeated except that 4.5 g of 3-aminoindazole was employed instead of the 3-amino-4-chloroindazole. As a result, 5.97 g of 1-(3-diethylaminopropyl)-3-(3-diethylaminopropylamino)indazole was obtained in a yield of 51%.

A mixture consisting of 14.1 g of the 1-(3-diethylaminopropyl)-3-(3-diethylaminopropylamino)indazole and 4.3 g of 95% by weight sulfuric acid was stirred for 3 hours at 80° C. To the mixture was added 13 ml of water, and the pH of the mixture was adjusted to 14 with potassium hydroxide. After the mixture was washed twice with 20 ml of chloroform, water was removed under reduced pressure. To the residue were added 12.5 g of potassium hydroxide and 0.6 ml of water, and the mixture was stirred for 8 hours at 250° C. After cooling, to the mixture was added hydrochloric acid to separate crystals. The crystals were obtained by filtration and dried to give 6.28 g of 1-(3-diethylaminopropyl)-3-(3-diethylaminopropylamino)-5-hydroxyindazole having the following analytical values in a yield of 40%.

IR absorption spectrum ($\nu_{max}$, cm$^{-1}$): 3610, 3320, 3210, 2960, 2830 and 1610.

NMR spectrum [$\delta$, CD$_3$OD]: 0.94(t, 12H), 1.98(m, 4H), 2.52(m, 8H), 4.11(t, 4H) and 7.10(m, 3H).

Mass spectrum (m/e): 375(M$^+$), 346(M-29), 317(M-58) and 276(M-99).

In 50 ml of absolute ethyl alcohol was dissolved 4.5 g of the 1-(3-diethylaminopropyl)-3-(3-diethylaminopropylamino)-5-hydroxyindazole, and into the solution was introduced dried hydrogen chloride gas under cooling with ice. Then to the solution was added anhydrous diethyl ether to separate crystals. The crystals were obtained by filtration and dried to give 1-(3-diethylaminopropyl)-3-(3-diethylaminopropylamino)-5-hydroxyindazole dihydrochloride having the following analytical value.

Elemental Analysis Value: C$_{21}$H$_{39}$ON$_5$Cl$_2$: Calcd.(%): C 56.24; H 8.77; N 15.62; Cl 15.81. Found (%): C 56.32; H 8.81; N 15.54; Cl 15.69.

EXAMPLES 121 and 122

The same procedures as described in Example 119 were repeated except that 3-amino-chloroindazoles as set forth in Table 42 were employed instead of the 3-amino-4-chloroindazole. The results including the analytical values are shown in Tables 42 and 43.

TABLE 42

| Example No. | 3-Amino-chloroindazole | (g) | Product | Form | Yield (%) |
|---|---|---|---|---|---|
| 121 | Cl-substituted 3-aminoindazole (structure) | 5.66 | HO-substituted indazole with NH(CH$_2$)$_3$N(C$_2$H$_5$)$_2$ and (CH$_2$)$_3$N(C$_2$H$_5$)$_2$ | Oily Substance | 47 |
| 122 | Cl-substituted 3-aminoindazole (structure) | 5.66 | OH-substituted indazole with NH(CH$_2$)$_3$N(C$_2$H$_5$)$_2$ and (CH$_2$)$_3$N(C$_2$H$_5$)$_2$ | Oily Substance | 37 |

TABLE 43

| Example No. | IR Spectrum (cm$^{-1}$) | NMR Spectrum ($\delta$, CD$_3$OD) | Mass Spectrum (m/e) | Elemental Analysis Value Calcd. (%) | Found (%) |
|---|---|---|---|---|---|
| 121 | 3610, 3300 3230, 2980 2860, 1620 | 0.94(t, 12H), 1.97(m, 4H) 2.51(m, 8H), 4.19(t, 4H) 7.17(m, 3H) | 375, 346, 317 276 | C$_{21}$H$_{39}$ON$_5$Cl$_2$ C 56.24; H 8.77 N 15.62; Cl 15.81 | C 56.33; H 8.81 N 15.58; Cl 15.68 |
| 122 | 3600, 3320 | 0.92(t, 12H), 1.98(m, 4H) | 375, 346, 317 | C$_{21}$H$_{39}$ON$_5$Cl$_2$ | |

TABLE 43-continued

| Example No. | IR Spectrum (cm$^{-1}$) | NMR Spectrum (δ, CD$_3$OD) | Mass Spectrum (m/e) | Elemental Analysis Value Calcd. (%) | Found (%) |
| --- | --- | --- | --- | --- | --- |
| | 3240, 2960 2860, 1610 | 2.52(m, 8H), 4.20(t, 4H) 7.20(m, 3H) | 276 | C 56.24; H 8.77 N 15.62; Cl 15.81 | C 56.11; H 8.69 N 15.81; Cl 15.97 |

EXAMPLE 123

The same procedures as described in Example 119 were repeated except that 8.75 g of 3-amino-5-iodoindazole was employed instead of the 5.66 g of 3-amino-4-chloroindazole. As a result, 8.40 g of 1-(3-diethylaminopropyl)3-(3-diethylaminopropylamino)-5-iodoindazole having the following analytical values was obtained in a yield of 53%

IR absorption spectrum ($\nu_{max}$, cm$^{-1}$): 3300, 3160, 2980, 1615 and 1540.

NMR spectrum [δ, CDCl$_3$]: 0.93(t, 12H), 1.98(m, 4H), 2.51(m, 8H), 4.20(t, 4H), 7.01(d, 1H), 7.35(d, 1H) and 8.02(s, 1H).

Mass spectrum (m/e): 485(M$^+$), 456(M-29), 427(M-58) and 386(M-99).

In 50 ml of absolute ethyl alcohol was dissolved 4.0 g of the 1-(3-diethylaminopropyl)-3-(3-diethylaminopropylamino)-5-iodoindazole, and into the solution was introduced dried hydrogen chloride gas under cooling with ice. Then to the solution was added anhydrous diethyl ether to separate crystals. The crystals were obtained by filtration and dried to give 1-(3-diethylaminopropyl)-3-(3-diethylaminopropylamino)-5-iodoindazole dihydrochloride having the following analytical value.

Elemental Analysis Value: C$_{21}$H$_{38}$N$_5$ICl$_2$: Calcd.(%): C 45.17; H 6.86; N 12.54; I 22.73: Cl 12.70. Found (%): C 44.99; H 6.75; N 12.71; I 22.82; Cl 12.73.

EXAMPLE 124

The same procedures as described in Example 123 were repeated except that 8.75 g of 3-amino-7-iodoindazole was employed instead of the 3-amino-5-iodoindazole. As a result, 7.77 g of 1-(3-diethylaminopropyl)-3-(3-diethylaminopropylamino)-7-iodoindazole having the following analytical values was obtained in a yield of 49%.

IR absorption spectrum ($\delta_{max}$, cm$^{-1}$): 3310, 3170, 2970, 1610 and 1550.

NMR spectrum [δ, CDCl$_3$]: 0.94(t, 12H), 1.97(m, 4H), 2.50(m, 8H), 4.25(t, 4H), 7.03(d, 1H), 7.31(d, 1H) and 7.69(d, 1H).

Mass spectrum (m/e): 485(M$^+$), 456(M-29), 427(M-58) and 386(M-99).

In 50 ml of absolute ethyl alcohol was dissolved 4.0 g of the 1-(3-diethylaminopropyl)-3-(3-diethylaminopropylamino)-7-iodoindazole, and into the solution was introduced dried hydrogen chloride gas under cooling with ice. Then to the solution was added anhydrous diethyl ether to separate crystals. The crystals were obtained by filtration and dried to give 1-(3-diethylaminopropyl)-3-(3-diethylaminopropylamino)-7-iodoindazole dihydrochloride having the following analytical value.

Elemental Analysis Value: C$_{21}$H$_{38}$N$_5$ICl$_2$: Calcd.(%): C 45.17; H 6.86; N 12.54; I 22.73; Cl 12.70. Found (%): C 45.32; H 6.91; N 12.21; I 22.68; Cl 12.88.

EXAMPLE 125

In 30 ml of sulfuric acid was dissolved 58.5 g of 1-(3-diethylaminopropyl)-3-(3-diethylaminopropylamino)indazole prepared by the same method as described in Example 120. To the solution were added dropwise 10.2 ml of nitric acid and 10.2 ml of sulfuric acid at 0° C. The solution was stirred for 1 hour, and the pH of the solution was adjusted to 10.4 with an aqueous ammonia solution. The solution was extracted three times with 50 ml of chloroform. The chloroform layer was washed with water and dried over anhydrous sodium sulfate, and then chloroform was removed under reduced pressure. The residue thus obtained was subjected to an alumina-column chromatography (alumina: 200 g) using chloroform as the developing solvent to give 13.45 g of 1-(3-diethylaminopropyl)-3-(3-diethylaminopropylamino)-5,7-dinitroindazole having the following analytical values in a yield of 20%.

IR absorption spectrum ($\delta_{max}$, cm$^{-1}$): 3480, 3350, 3080 and 1610.

NMR spectrum [δ, d$_6$-DMSO]: 0.96(t, 12H)., 1.97(m, 4H), 2.51(m, 8H), 4.12(t, 4H), 7.88(s, 1H) and 8.10(s, 1H).

Mass spectrum (m/e): 451(M$^{30}$), 405(M-46), 359(M-92) and 343(M-108).

A mixture consisting of 12.0 g of the 1-(3-diethylaminopropyl)-3-(3-diethylaminopropylamino)-5,7-dinitroindazole, 18 g of iron powder, 60 ml of methyl alcohol, 30 ml of water and 3 ml of hydrochloric acid was stirred for 1.5 hours at 70° C. After cooling, the mixture was filtered, and the pH of the filtrate was adjusted to 11 with an aqueous potassium carbonate solution. The filtrate was extracted three times with 50 ml of ethyl acetate, and the ethyl acetate layer was washed with water. The layer was dried over anhydrous sodium sulfate, and ethyl acetate was removed under reduced pressure. The residue thus obtained was subjected to an alumina-column chromatography(alumina: 200 g) using chloroform as the developing solvent to give 2.46 g of 1-(3-diethylaminopropyl)-3-(3-diethylaminopropylamino)-5,7-diaminoindazole having the following analytical values in a yield of 23%.

IR absorption spectrum ($\nu$max, cm$^{-1}$): 3470, 3340, 3160, 1610 and 1590.

NMR spectrum [δ, CD$_3$OD]: 0.97(t, 12H), 1.98(m, 4H), 2.49(m, 8H), 4.21(t, 4H) and 6.98(m, 2H).

Mass spectrum (m/e): 391(M$^+$), 375(M-16), 359(M-32) and 343(M-48).

In 20 ml of absolute ethyl alcohol was dissolved 2.5 g of the 1-(3-diethylaminopropyl)-3-(3-diethylaminopropylamino)-5,7-diaminoindazole, and into the solut was introduced dried hydrogen chloride gas under cooling with ice. Then to the solution was added anhydrous diethyl ether to separate crystals. The crystals were obtained by filtration and dried to give 1-(3-diethylaminopropyl)-3-(3-diethylaminopropylamino)-5,7-diaminoi tetrahydrochloride having the following analytical value.

Elemental Analysis Value: $C_{21}H_{43}N_7Cl_4$: Calcd.(%): C 47.11; H 8.09; N 18.31; Cl 26.49. Found (%): C 46.98; H 7.98; N 18.58; Cl 26.46.

EXAMPLES 126–129

The same procedures as described in Example 120 were repeated except that 1-(3-diethylaminopropyl)-3-(aminoalkylamino)indazoles as obtained in the following method were employed instead of the 1-(3-diethylaminopropyl)-3-(3-diethylaminopropylamino)indazole.

The 1-(3-diethylaminopropyl)-3-(aminoalkylamino)indazoles were obtained by repeating the procedures as described in Example 89 except that 3-phthalimido-indazole and an ω-halogenoalkylamine hydrobromide a set forth in Table 44 were employed instead of the 3-phthalimido-4-chloroindazole and the 9.0 g of 3-bromopropyldiethylamine hydrobromide, respectively.

The results including the analytical values are shown in Tables 44 and 45.

TABLE 44

| Example No. | ω-Halogenoalkylamine Hydrobromide | (g) | Product | Form | Yield (%) |
|---|---|---|---|---|---|
| 126 | piperidino-N—(CH$_2$)$_3$Br.HBr | 9.30 | HO-indazole-NH(CH$_2$)$_3$N(piperidino); N1-(CH$_2$)$_3$N(C$_2$H$_5$)$_2$ | Oily Substance | 52 |
| 127 | piperidino-N—(CH$_2$)$_6$Br.HBr | 10.68 | HO-indazole-NH(CH$_2$)$_6$N(piperidino); N1-(CH$_2$)$_3$N(C$_2$H$_5$)$_2$ | Oily Substance | 45 |
| 128 | (C$_4$H$_9$)$_2$N—(CH$_2$)$_3$Br.HBr | 10.70 | HO-indazole-NH(CH$_2$)$_3$N(C$_4$H$_9$)$_2$; N1-(CH$_2$)$_3$N(C$_2$H$_5$)$_2$ | Oily Substance | 55 |
| 129 | piperidino-N—CHCH$_2$CH$_2$Br.HBr; CH$_3$ | 9.74 | HO-indazole-NHCH$_2$CH$_2$CH(CH$_3$)N(piperidino); N1-(CH$_2$)$_3$N(C$_2$H$_5$)$_2$ | Oily Substance | 53 |

TABLE 45

| Example No. | IR Spectrum (cm$^{-1}$) | NMR Spectrum (δ, CD$_3$OD) | Mass Spectrum (m/e) | Elemental Analysis Value Calcd. (%) | Found (%) |
|---|---|---|---|---|---|
| 126 | 3610, 3320 3200, 2960 2810, 1610 | 0.95(t, 6H), 1.50(m, 8H) 2.28(m, 8H), 2.46(q, 4H) 4.21(t, 4H), 7.25(m, 3H) | 388, 359, 330 274 | $C_{22}H_{30}ON_5Cl_2$ C 57.38; H 8.54 N 15.21; Cl 15.40 | C 57.41; H 8.51 N 15.24; Cl 15.43 |
| 127 | 3600, 3330 3210, 2980 2820, 1620 | 0.97(t, 6H), 1.37(bm, 14H) 2.32(m, 10H), 2.48(q, 4H) 4.20(t, 4H), 7.23(m, 3H) | 430, 401, 372 3.6 | $C_{25}H_{43}ON_5Cl_2$ C 59.75; H 9.03 N 12.93; Cl 14.11 | C 59.78; H 9.00 N 13.90; Cl 14.14 |
| 128 | 3590, 3315 3205, 2970 2805, 1610 | 2.31(m, 10H), 2.48(q, 4H) 0.96(m, 12H), 1.29(m, 10H) 4.12(t, 4H), 7.24(m, 3H) | 432, 413, 374 318 | $C_{25}H_{47}ON_5Cl_2$ C 59.51; H 9.39 N 13.88; Cl 14.05 | C 59.54; H 9.36 N 13.91; Cl 14.02 |
| 129 | 3610, 3300 3205, 2980 2800, 1600 | 0.90(m, 9H), 1.40(m, 8H) 2.30(m, 9H), 2.47(q, 4H) 4.22(t, 4H), 7.26(m, 3H) | 402, 373, 344 288 | $C_{23}H_{41}ON_5Cl_2$ C 58.22; H 8.71 N 14.76; Cl 14.94 | C 58.25; H 8.74 N 14.73; Cl 14.91 |

EXAMPLE 130

The same procedures for preparing 1-(3-diethylaminopropyl)-3-amino-4-chloroindazole as described in Example 89 were repeated except that 8 g of 3-phthalimidoindazole and 10 g of 3-bromopropylpiperidine hydrobromide were employed instead of the 3-phthalimido-4-chloroindazole and the 3-bromopropyldiethylamine hydrobromide, respectively. As a result, 12.3 g of 1-(3-piperidinopropyl)-3-aminoindazole was obtained.

To 60 ml of anhydrous N,N-dimethylformamide were added 8.4 g of the 1-(3-piperidinopropyl)-3-aminoindazole, 8.98 g of 3-bromopropyldiethylamine hydrobromide and 7.89 g of anhydrous potassium carbonate, and the mixture was stirred for 12 hours at 80° C. After cooling, the mixture was added with 80 ml of water and extracted with diethyl ether. The diethyl ether layer was extracted three times with 2N hydrochloric acid, and the hydrochloric acid layer was washed with diethyl ether. The pH of the layer was adjusted to at least 11 with potassium carbonate, and the alkali layer was extracted three times with chloroform. The chloroform layer was dried over anhydrous sodium sulfate, and chloroform was removed under reduced pressure. The residue thus obtained was subjected to an alumina-column chromatography(alumina: 200 g) using chloroform as the developing solvent to give 6.22 g of 1-(3-piperidinopropyl)-3-(3-diethylaminopropylamino)indazole having the following analytical values in a yield of 53%.

IR absorption spectrum ($\nu_{max}$, cm$^{-1}$): 3320, 3210, 2960, 2820 and 1615.

NMR spectrum [δ, CDCl$_3$]: 0.97(t, 6H), 1.49(m, 8H), 2.32(m, 10H), 2.41(p, 4H). 4.15(t, 4H) and 7.20(m, 4H).

Mass spectrum (m/e): 372(M+, 100), 343(M-29, 61), 314(M-58, 79), 258(M-114, 132) and 174(M-198, 140).

The same procedures as described in Example 120 were repeated except that 14.6 g of the 1-(3-piperidinopropyl)-3-(3-diethylaminopropylamino)indazole was employed instead of the 14.1 g of 1-(3-diethylaminopropyl)-3-(3-diethylaminopropylamino)indazole. As a result, 6.66 g of 1-(3-piperidinopropyl)-3-(3-diethylaminopropylamino)-5-hydroxyindazole having the following analytical values was obtained in a yield of 41%.

IR absorption spectrum ($\nu_{max}$, cm$^{-1}$): 3600, 3310, 3210, 2970, 2820 and 1610.

NMR spectrum [δ, CD$_3$OD]: 0.97(t, 6H), 1.47(m, 8H), 2.34(m, 10H), 2.43(q, 4H), 4.21(t, 4H) and 7.21(m, 3H).

Mass spectrum (m/e): 388(M+), 359(M-29), 330(M-58), 274(M-114) and 190(M-198).

In 50 ml of absolute ethyl alcohol was dissolved 4.0 g of the 1-(3-piperidinopropyl)-3-(3-diethylaminopropylamino)-5-hydroxyindazole, and into the solution was introduced dried hydrogen chloride gas under cooling with ice. Then to the solution was added anhydrous diethyl ether to separate crystals. The crystals were obtained by filtration and dried to give 1-(3-piperidinopropyl)-3-(3-diethylaminopropylamino)-5-hydroxyindazole dihydrochloride having the following analytical value.

Elemental Analysis Value: $C_{22}H_{39}ON_5Cl_2$: Calcd.(%): C 57.38; H 8.54; N 15.21; Cl 15.40. Found (%): C 57.36; H 8.51; N 15.24; Cl 15.42.

EXAMPLES 131-133

The same procedures as described in Example 130 were repeated except that ω-halogenoalkylamine hydrobromides as set forth in Table 46 were employed instead of the 8.98 g of 3-bromopropyldiethylamine hydrobromide. The results including the analytical values are shown in Tables 46 and 47.

TABLE 46

| Example No. | ω-Halogenoalkylamine Hydrobromide | (g) | Product | Form | Yield (%) |
|---|---|---|---|---|---|
| 131 | ⟨N—(CH$_2$)$_3$Br.HBr⟩ (piperidine) | 9.30 | HO-[indazole]-NH(CH$_2$)$_3$N⟨piperidine⟩, N1-(CH$_2$)$_3$N⟨piperidine⟩ | Oily Substance | 57 |
| 132 | ⟨N—(CH$_2$)$_6$Br.HBr⟩ (piperidine) | 10.68 | HO-[indazole]-NH(CH$_2$)$_6$N⟨piperidine⟩, N1-(CH$_2$)$_3$N⟨piperidine⟩ | Oily Substance | 47 |
| 133 | ⟨N—CHCH$_2$CH$_2$Br.HBr, CH$_3$⟩ (piperidine) | 9.74 | HO-[indazole]-NHCH$_2$CH$_2$CHN⟨piperidine⟩, CH$_3$; N1-(CH$_2$)$_3$N⟨piperidine⟩ | Oily Substance | 49 |

TABLE 47

| Example No. | IR Spectrum (cm$^{-1}$) | NMR Spectrum (δ, CD$_3$OD) | Mass Spectrum (m/e) | Elemental Analysis Value Calcd. (%) | Found (%) |
|---|---|---|---|---|---|
| 131 | 3610, 3310 | 1.56(m, 16H), 2.21(m, 12H) | 401, 386, 372 | C$_{23}$N$_{39}$ON$_5$Cl$_2$ | |
| | 3220, 2980 | 4.21(t, 4H), 7.26(m, 3H) | 358 | C 58.47; H 8.32 | C 58.44; H 8.35 |
| | 2840, 1610 | | | N 14.82; Cl 15.01 | N 14.85; Cl 14.98 |
| 132 | 3620, 3310 | 1.40(m, 20H), 2.29(m, 14H) | 442, 428, 400 | C$_{26}$H$_{45}$ON$_5$Cl$_2$ | |
| | 3200, 2975 | 4.18(t, 4H), 7.27(m, 3H) | 386, 372 | C 60.69; H 8.81 | C 60.66; H 8.84 |
| | 2820, 1605 | | | N 13.61; Cl 13.78 | N 13.64; Cl 13.75 |
| 133 | 3615, 3300 | 0.87(d, 3H), 1.41(m, 14H) | 414, 400, 386 | C$_{24}$H$_{41}$ON$_5$Cl$_2$ | |
| | 3190, 2975 | 2.21(m, 13H), 4.22(t, 4H) | 372, 358 | C 59.25; H 8.49 | C 59.22; H 8.46 |
| | 2805, 1620 | 7.18(m, 3H) | | N 14.39; Cl 14.57 | N 14.42; Cl 14.59 |

EXAMPLE 134

The same procedures for preparing 1-(3-diethylaminopropyl)-3-amino-4-chloroindazole as described in Example 89 were repeated except that 8 g of 3-phthalimidoindazole and 10.5 g of 1-(1-methyl-3-bromopropyl)-piperidine hydrobromide were employed instead of the 3-phthalimido-4-chloroindazole and the 3-bromopropyldiethylamine hydrobromide, respectively. As a result, 12.5 g of 1-(3-piperidinobutyl)-3-aminoindazole was obtained.

To 60 ml of anhydrous N,N-dimethylformamide were added 8.30 g of the 1-(3-piperidinobutyl)-3-aminoindazole, 8.07 g of 3-bromopropyldimethylamine hydrobromide and 7.89 g anhydrous potassium carbonate, and the mixture was stirred for 12 hours at 80° C. After cooling, the mixture was added with 80 ml of water and extracted with diethyl ether. The diethyl ether layer was extracted three times with 2N hydrochloric acid, and the hydrochloric acid layer was washed with diethyl ether. The pH of the layer was adjusted to at least 11 with potassium carbonate, and the alkali layer was extracted three times with chloroform. The chloroform layer was dried over anhydrous sodium sulfate, and chloroform was removed under reduced pressure. The residue thus obtained was subjected to an alumina-column chromatography(alumina: 200 g) using chloroform as the developing solvent to give 6.22 g of 1-(3-piperidinobutyl)-3-(3-diethylaminopropylamino)indazole having the following analytical values in a yield of 50%.

IR absorption spectrum ($\nu_{max}$, cm$^{-1}$): 3330, 3200, 2970, 2830 and 1610.

NMR spectrum [δ, CDCl$_3$]: 0.89(m, 9H), 1.40(m, 8H), 2.30(m, 9H), 2.46(q, 4H), 4.19(t, 4H) and 7.25(m, 4H).

Mass spectrum (m/e): 386(M+), 357(M-29), 328(M-58) and 272(M-114).

The same procedures as described in Example 120 were repeated except that 15.2 g of the 1-(3-piperidinobutyl)-3-(3-diethylaminopropylamino)indazole was employed instead of the 14.1 g of 1-(3-diethylaminopropyl)-3-(3-diethylaminopropylamino) indazole. As a result, 6.56 g of 1-(3-piperidinobutyl)-3-(3-diethylaminopropylamino)-5-hydroxyindazole having the following analytical values was obtained in a yield of 39%.

IR absorption spectrum ($\nu_{max}$, cm$^{-1}$): 3590, 3310, 3200, 2970, 2840 and 1610.

NMR spectrum [δ, CD$_3$OD]: 0.89(m, 9H), 1.41(m, 8H), 2.31(m, 9H), 2.47(q, 4H), 4.20(t, 4H) and 7.19(m, 3H).

Mass spectrum (m/e): 402(M+), 373(M-29), 344(M-58), 288(M-144) and 204(M-198).

In 50 ml of absolute ethyl alcohol was dissolved 4.0 g of the 1-(3-piperidinobutyl)-3-(3-diethylaminopropylamino)-5-hydroxyindazole, and into the solution was introduced dried hydrogen chloride gas under cooling with ice. Then to the solution was added anhydrous diethyl ether to separate crystals. The crystals were obtained by filtration and dried to give 1-(3-piperidinobutyl)-3-(3-diethylaminopropylamino)-5-hydroxyindazole dihydrochloride having the following analytical value.

Elemental Analysis Value: C$_{23}$H$_{41}$ON$_5$Cl$_2$: Calcd.(%): C 58.22; H 8.71; N 14.76; Cl 14.94. Found (%): C 58.20; H 8.68; N 14.79; Cl 14.96.

EXAMPLES 135–137

The same procedures as described in Example 134 were repeated except that ω-halogenoalkylamine hydrobromides as set forth in Table 48 were employed instead of the 8.07 g of 3-bromopropyldiethylamine hydrobromide. The results including the analytical values are shown in Tables 48 and 49.

TABLE 48

| Example No. | ω-Halogenoalkylamine Hydrobromide | (g) | Product | Form | Yield (%) |
|---|---|---|---|---|---|
| 135 | 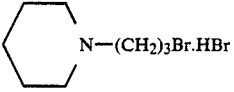 | 9.30 | 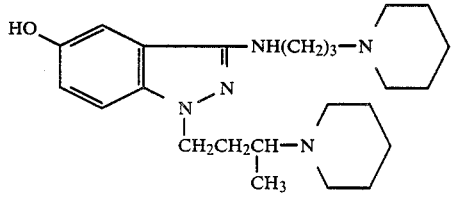 | Oily Substance | 46 |

TABLE 48-continued

| Example No. | ω-Halogenoalkylamine Hydrobromide | (g) | Product | Form | Yield (%) |
|---|---|---|---|---|---|
| 136 | (piperidine)N—CHCH$_2$CH$_2$Br·HBr with CH$_2$–CH(CH$_3$)$_2$ substituent | 11.11 | HO-indazole-NHCH$_2$CH$_2$CH–N(piperidine) with CH$_2$–CH(CH$_3$)$_2$; N-substituted with CH$_2$CH$_2$CHN(piperidine)CH$_3$ | Oily Substance | 49 |
| 137 | (CH$_3$)$_2$N—CHCH$_2$CH$_2$Br·HBr with CH$_3$ | 8.46 | HO-indazole-NHCH$_2$CH$_2$CHN(CH$_3$)$_2$ with CH$_3$; N-substituted with CH$_2$CH$_2$CHN(piperidine)CH$_3$ | Oily Substance | 43 |

TABLE 49

| Example No. | IR Spectrum (cm$^{-1}$) | NMR Spectrum (δ, CD$_3$OD) | Mass Spectrum (m/e) | Elemental Analysis Value Calcd. (%) | Elemental Analysis Value Found (%) |
|---|---|---|---|---|---|
| 135 | 3610, 3330 3220, 2980 2830, 1630 | 0.91(d, 3H), 1.40(m, 14H) 2.23(m, 13H), 4.20(t, 4H) 7.18(m, 3H) | 414, 400, 386 372 | C$_{24}$H$_{41}$ON$_5$Cl$_2$ C 59.25; H 8.49 N 14.39; Cl 14.97 | C 59.28; H 8.46 N 14.36; Cl 14.60 |
| 136 | 2600, 3310 3210, 2980 2860, 1600 | 0.92(m, 9H), 1.48(m, 19H) 2.23(m, 10H), 4.30(t, 4H) 7.25(m, 3H) | 470, 456, 440 425 | C$_{28}$H$_{49}$ON$_5$Cl$_2$ C 61.98; H 9.10 N 12.91; Cl 13.07 | C 61.95; H 9.13 N 12.94; Cl 13.04 |
| 137 | 2615, 3320 3200, 2970 2860, 1620 | 0.91(m, 6H), 1.33(m, 10H) 2.31(m, 12H), 4.21(t, 4H) 7.24(m, 3H) | 388, 373, 358 343, 259 | C$_{22}$H$_{39}$ON$_5$Cl$_2$ C 57.38; H 8.54 N 15.21; Cl 15.40 | C 57.35; H 8.51 N 15.24; Cl 15.43 |

EXAMPLE 138

The same procedures for preparing 1-(3-diethylaminopropyl)-3-amino-4-chloroindazole as described in Example 89 were repeated except that 8 g of 3-phthalimidoindazole and 8.6 g of (1-methyl-3-bromopropyl)dimethylamine hydrobromide were employed instead of the 3-phthalimido-4-chloroindazole and the 3-bromopropyldiethylamine hydrobromide, respectively. As a result, 9.2 g of 1-(3-dimethylaminobutyl)-3-aminoindazole was obtained.

To 60 ml of anhydrous N,N-dimethylformamide were added 7.50 g of the 1-(3-dimethylaminobutyl)-3-aminoindazole, 8.98 g of 3-bromopropyldiethylamine hydr bromide and 7.89 g of anhydrous potassium carbonate, and the mixture was stirred for 12 hours at 80° C. After cooling, the mixture was added with 80 ml of water and extracted with diethyl ether. The diethyl ether layer was extracted three times with 2N hydrochloric acid, and the hydrochlor.ic acid layer was washed with diethyl ether. The pH of the layer was adjusted to at least 11 with potassium carbonate, and the alkali layer was extracted three times with chloroform. The chloroform layer was dried over anhydrous sodium sulfate, and chloroform was removed under reduced pressure. The residue thus obtained was subjected to an alumina-column chromatography (alumina: 200 g) using chloroform as the developing solvent to give 6.18 g of 1-(3-dimethylaminobutyl)-3-(3-diethylaminopropylamino)indazole having the following analytical values in a yield of 52%.

IR absorption spectrum ($v_{max}$, cm$^{-1}$): 3310, 3200, 2950, 2810 and 1620.

NMR spectrum [δ, CDCl$_3$]: 0.95(m, 9H), 2.90(m, 13H), 2.44(q, 4H), 4.17(t, 4H) and 7.15(m, 4H).

Mass spectrum (m/e): 346(M$^+$, 100), 317(M-29, 76), 288(M-58, 49), 274(M-72, 110) and 260(M-96, 130).

The same procedures as described in Example 120 were repeated except that 13.6 g of the 1-(3-dimethylaminobutyl)-3-(3-diethylaminopropylamino)indazole was employed instead of the 14.1 g of 1-(3-diethylaminopropyl)-3-(3-diethylaminopropylamino)indazole. As a result, 6.36 g of 1-(3-dimethylaminobutyl)-3-(3-diethylaminopropylamino)-5-hydroxyindazole having the following analytical values was obtained in a yield of 42%.

IR absorption spectrum ($v_{max}$, cm$^{-1}$): 3600, 3310, 3200, 2950, 2810 and 1610.

NMR spectrum [δ, CD$_3$OD]: 0.95(m, 9H), 2.29(m, 13H), 2.49(q, 4H), 4.17(t, 4H) and 7.20(m, 3H).

Mass spectrum (m/e): 362(M$^+$), 333(M-29), 304(M-58), 290(M-72) and 276(M-96).

In 50 ml of absolute ethyl alcohol was dissolved 3.8 g of the 1-(3-dimethylaminobutyl)-3-(3-diethylaminopropylamino)-5-hydroxyindazole, and into the solution was introduced dried hydrogen chloride gas under cooling with ice. Then to the solution was added anhydrous diethyl ether to separate crystals. The crystals were obtained by filtration and dried to give 1-(3-dimethylaminobutyl)-3-(3-diethylaminopropylamino)-5-hydroxyindazole dihydrochloride having the following analytical value.

Elemental Analysis Value: $C_{29}H_{37}ON_5Cl_2$: Calcd.(%): C 55.29; H 8.58; N 16.12; Cl 16.32. Found (%): C 55.32; H 8.55; N 10.14; Cl 16.30.

EXAMPLES 139–141

The same procedures as described in Example 138 were repeated except that w-halogenoalkylamine hydrobromides as set forth in Table 50 were employed instead of the 8.98 g of 3-bromopropyldiethylamine hydrobromide. The results including the analytical values are shown in Tables 50 and 51.

EXAMPLE 142

The same procedures for preparing 1-(3-diethylaminopropyl)-3-amino-4-chloroindazole as described in Example 89 were repeated except that 8 g of 3-phthalimidoindazole and 9.5 g of 3-bromopropylpyrrolidine hydrobromide were employed instead of the 3-phthalimido-4-chloroindazole and the 3-bromopropyldiethylamine hydrobromide, respectively. As a result, 8.2 g of 1-(3-pyrrolidinopropyl)-3-aminoindazole was obtained.

To 60 ml of anhydrous N,N-dimethylformamide were added 7.92 g of the 1-(3-pyrrolidinopropyl)-3-aminoindazole, 9.94 g of 3-bromopropylhomopiperidine hydrobromide and 7.89 g of anhydrous potassium carbonate, and the mixture was stirred for 12 hours at 80° C. After cooling, the mixture was added with 80 ml of water, and extracted with diethyl ether. The diethyl ether layer was extracted three times with 2N hydrochloric acid and the hydrochloric acid layer was washed with diethyl ether. The pH of the layer was

TABLE 50

| Example No. | ω-Halogenoalkylamine Hydrobromide | (g) | Product | Form | Yield (%) |
|---|---|---|---|---|---|
| 139 | ⟨N⟩—(CH₂)₃Br·HBr (piperidine) | 9.30 | HO-indazole-NH(CH₂)₃N⟨piperidine⟩ with N-CH₂CH₂CHN(CH₃)₂/CH₃ | Oily Substance | 42 |
| 140 | ⟨N⟩—CHCH₂CH₂Br·HBr, CH₃ (piperidine) | 9.74 | HO-indazole-NHCH₂CH₂CHN⟨piperidine⟩/CH₃ with N-CH₂CH₂CHN(CH₃)₂/CH₃ | Oily Substance | 46 |
| 141 | C₂H₅\N—CHCH₂CH₂Br·HBr, C₂H₅/ with CH₂/CH(CH₃)₂ | 10.73 | HO-indazole-NHCH₂CH₂CHN(C₂H₅)₂ with CH₂CH(CH₃)₂ and CH₂CH₂CHN(CH₃)₂/CH₃ | Oily Substance | 40 |

TABLE 51

| Example No. | IR Spectrum (cm⁻¹) | NMR Spectrum (δ, CD₃OD) | Mass Spectrum (m/e) | Elemental Analysis Value Calcd. (%) | Found (%) |
|---|---|---|---|---|---|
| 139 | 3610, 3330 | 0.91(d, 3H), 1.58(m, 10H) | 374, 359, 344 | $C_{21}H_{37}ON_5Cl_2$ | |
|  | 3200, 2970 | 2.24(m, 13H), 4.18(t, 4H) | 330 | C 56.50; H 8.35 | C 56.47; H 8.32 |
|  | 2840, 1610 | 7.15(m, 3H) |  | N 15.69; Cl 15.88 | N 15.72; Cl 15.91 |
| 140 | 3620, 3300 | 0.90(m, 6H), 1.55(m, 10H) | 388, 373, 358 | $C_{22}H_{39}ON_5Cl_2$ | |
|  | 3230, 2960 | 2.35(m, 12H), 4.21(t, 4H) | 344 | C 57.38; H 8.54 | C 57.33; H 8.51 |
|  | 2830, 1610 | 7.18(m, 3H) |  | N 15.20; Cl 15.40 | N 15.23; Cl 15.43 |
| 141 | 3600, 3320 | 0.93(m, 15H), 1.51(m, 7H) | 418, 403, 388 | $C_{24}H_{45}ON_5Cl_2$ | |
|  | 3215, 2960 | 2.23(m, 12H), 4.21(t, 2H) | 374 | C 58.76; H 9.25 | C 58.03; H 9.28 |
|  | 2850, 1610 | 7.26(m, 3H) |  | N 14.28; Cl 14.45 | N 14.32; Cl 14.42 | adjusted to at least 11 with potassium carbonate, and the alkali layer was extracted three times with chloroform. The chloroform layer was dried over anhydrous sodium sulfate, and chloroform was removed under reduced pressure. The residue thus obtained was subjected to an alumina-column chromatography(alumina: 200 g) using chloroform as the developing solvent to give 6.64 g of 1-(3-pyrrolidinopropyl)-3-(3-homopiperidinopropylamino)indazole having the following analytical values in a yield of 56%.

IR absorption spectrum ($\nu_{max}$, cm$^{-1}$): 3320, 3230, 2970 and 2860.

NMR spectrum [$\delta$, CDCl$_3$]: 1.63(m, 14H), 2.14(bs, 2H), 2.50(m, 12H), 4.25(t, 4H) and 7.20(m, 4H).

Mass spectrum (m/e): 383(M$^+$), 313(M-70), 299(M-84), 285(M-98) and 271(M-12).

The same procedures as described in Example 120 were repeated except that 14.6 g of the 1-(3-pyrrolidino-propyl)-3-(3-homopiperidinopropylamino)indazole was employed instead of the 14.1 g of 1-(3-diethylaminopropyl)-3-(3-diethylaminopropylamino)indazole. As a result, 7.35 g of 1-(3-pyrrolidinopropyl)-3-(3-homopiperidinopropylamino)-5-hydroxyindazole having the following analytical values was obtained in a yield of 44%.

IR absorption spectrum ($\nu_{max}$, cm$^{-1}$): 3610, 3310, 3240, 2960, 2870 and 1610.

NMR spectrum [$\delta$, CD$_3$OD]: 1.67(m, 14H), 2.17(bs, 2H), 2.51(m, 12H), 4.17(t, 4H) and 7.17(m, 3H).

Mass spectrum (m/e): 399(M$^+$), 329(M-70), 315(M-84), 301(M-98) and 287(M-112).

In 50 ml of absolute ethyl alcohol was dissolved 3.0 g of the 1-(3-pyrrolidinopropyl)-3-(3-homopiperidinopropylamino)-5-hydroxyindazole, and into the solution was introduced dried hydrogen chloride gas under cooling with ice. Then to the solution was added anhydrous diethyl ether to separate crystals. The crystals were obtained by filtration and dried to give 1-(3-pyrrolidinopropyl)-3-(3-homopiperidinopropylamino)-5-hydroxyindazole dihydrochloride having the following analytical value.

Elemental Analysis Value: C$_{23}$H$_{39}$ON$_5$Cl$_2$: Calcd.(%): C 58.47; H 8.32; N 14.82; Cl 15.01. Found (%): C 58.31; H 8.29; N 14.95; Cl 15.09.

EXAMPLES 143 AND 144

The same procedures as described in Example 142 were repeated except that ω-halogenoalkylamine hydrobromides as set forth in Table 52 were employed instead of the 3-bromopropylhomopiperidine hydrobromide. The results including the analytical values are shown in Tables 52 and 53.

TABLE 52

| Example No. | ω-Halogenoalkylamine Hydrobromide | (g) | Product | Form | Yield (%) |
|---|---|---|---|---|---|
| 143 | (2-methylpiperidine)-N—(CH$_2$)$_3$Br·HBr | 9.94 | 5-hydroxy-1-(3-pyrrolidinopropyl)-3-[(3-(2-methylpiperidino)propyl)amino]indazole | Oily Substance | 41 |
| 144 | H$_3$C—N(piperazine)N—(CH$_2$)$_3$Br·HBr | 9.97 | 5-hydroxy-1-(3-pyrrolidinopropyl)-3-[(3-(4-methylpiperazino)propyl)amino]indazole | Oily Substance | 40 |

TABLE 53

| Example No. | IR Spectrum (cm$^{-1}$) | NMR Spectrum ($\delta$, CD$_3$OD) | Mass Spectrum (m/e) | Elemental Analysis Value | |
|---|---|---|---|---|---|
| | | | | Calcd. (%) | Found (%) |
| 143 | 3610, 3310 3220, 2980 2870, 1600 | 1.02(d, 3H), 1.66(m, 12H) 2.43(m, 8H), 2.75(m, 5H) 4.21(t, 4H), 7.21(m, 3H) | 399, 329, 315 301, 287 | C$_{23}$H$_{38}$ON$_5$Cl$_2$ C 58.47; H 8.32 N 14.82; Cl 15.01 | C 58.44; H 8.29 N 14.85; Cl 15.04 |
| 144 | 3615, 3315 3225, 2970 2855, 1610 | 1.71(m, 6H), 2.41(m, 21H) 4.20(t, 4H), 7.20(m, 3H) | 400, 330, 316 302, 288 | C$_{23}$H$_{38}$ON$_6$Cl$_2$ C 55.81; H 8.09 N 17.73; Cl 14.98 | C 55.84; H 8.06 N 17.72; Cl 15.02 |

EXAMPLE 145

The same procedures as described in Example 89 were repeated except that 8.0 g of 3-phthalimidoindazole and 10.1 g of 3-bromopropylmorpholine hydrobromide were employed instead of the 3-phthalimido-4-chloroindazole and the 4.83 g of 3-bromopropyldiethylamine hydrobromide, respectively. As a result, 8.7 g of 1-(3-morpholinopropyl)-3-(3-diethylaminopropylamino)indazole was obtained.

The same procedures as described in Example 120 were repeated except that 14.7 g of the 1-(3-morpholinopropyl)-3-(3-diethylaminopropylamino)indazole was employed instead of the 14.1 g of 1-(3-diethylaminopropyl)-3-(3-diethylaminopropylamino)indazole. As a result, 7.0 g of 1-(3-morpholinopropyl)-3-diethylaminopropylamino)-5-hydroxyindazole having the following analytical values was obtained in a yield of 43%.

IR absorption spectrum ($\nu_{max}$, cm$^{-1}$): 3610, 3400, 3220, 2960, 2870 and 1625.

NMR spectrum [$\delta$, CD$_3$OD]: 0.97(t, 6H), 1.58(m, 2H), 2.42(m, 14H), 3.57(t, 4H), 4.23(t, 4H) and 7.17(m, 3H).

Mass spectrum (m/e): 389(M$^+$), 317(M-72), 303(M-86), 289(M-100) and 275(M-114).

In 50 ml of absolute ethyl alcohol was dissolved 3.0 g of the 1-(3-morpholinopropyl)-3-(3-diethylaminopropylamino)-5-hydroxyindazole, and into the solution was introduced dried hydrogen chloride gas under cooling with ice. Then to the solution was added anhydrous diethyl ether to separate crystals. The crystals were obtained by filtration and dried to give 1-(3-morpholinopropyl)-3-(3-diethylaminopropylamino)-5-hydroxyindazole dihydrochloride having the following analytical value.

Elemental Analysis Value: $C_{21}H_{37}O_2N_5Cl_2$: Calcd.(%): C 54.54; H 8.06; N 15.14; Cl 15.33. Found (%): C 54.51; H 8.03; N 15.17; Cl 15.36

EXAMPLES 146–148

The same procedures as described in Example 145 were repeated except that g-halogenoalkylamine hydrobromides as set forth in Table 54 were employed instead of the 9.0 g of 3-bromopropyldiethylamine hydrobromide in Example 89. The results including the analytical values are shown in Tables 54 and 55.

TABLE 54

| Example No. | ω-Halogenoalkylamine Hydrobromide | (g) | Product | Form | Yield (%) |
|---|---|---|---|---|---|
| 146 | (2,6-dimethylpiperidine)-N—(CH$_2$)$_3$Br·HBr | 10.26 | 5-HO-indazole-3-NH(CH$_2$)$_3$-N(2,6-dimethylpiperidine); 1-(CH$_2$)$_3$N-morpholine | Oily Substance | 46 |
| 147 | (4-chloropiperidine)-N—(CH$_2$)$_3$Br·HBr | 10.46 | 5-HO-indazole-3-NH(CH$_2$)$_3$-N(4-chloropiperidine); 1-(CH$_2$)$_3$N-morpholine | Oily Substance | 49 |
| 148 | (4-hydroxypiperidine)-N—(CH$_2$)$_3$Br·HBr | 9.86 | 5-HO-indazole-3-NH(CH$_2$)$_3$-N(4-hydroxypiperidine); 1-(CH$_2$)$_3$N-morpholine | Oily Substance | 43 |

TABLE 55

| Example No. | IR Spectrum (cm$^{-1}$) | NMR Spectrum ($\delta$, CD$_3$OD) | Mass Spectrum (m/e) | Elemental Analysis Value Calcd. (%) | Found (%) |
|---|---|---|---|---|---|
| 146 | 3610, 3410 3220, 2990 1630, 1600 | 1.20(d, 6H), 1.37(m, 6H) 1.58(m, 2H), 2.37(m, 8H) 2.78(m, 2H), 3.56(t, 4H) 3.81(t, 2H), 4.21(t, 4H) 7.25(m, 3H) | 430, 358, 344 330, 316 | $C_{24}H_{41}O_2N_5Cl_2$ C 57.36; H 8.22 N 13.94; Cl 14.11 | C 57.33; H 8.19 N 13.97; Cl 14.14 |
| 147 | 2600, 3200 2960, 1620 1620, 1560 | 1.54(m, 6H), 2.18(m, 9H) 2.94(m, 6H), 3.55(t, 4H) 4.21(t, 4H), 7.26(m, 3H) | 436, 364, 350 336, 322 | $C_{22}H_{36}O_2N_5Cl_3$ C 51.92; H 7.13 N 13.76; Cl 20.90 | C 15.95; H 7.10 N 13.73; Cl 20.93 |
| 148 | 3610, 3420 3240, 2970 1630, 1575 | 1.55(m, 6H), 2.20(m, 9H) 2.96(m, 6H), 3.57(t, 4H) 4.19(t, 4H), 7.25(m, 3H) | 418, 346, 332 318, 304 | $C_{22}H_{37}O_3N_5Cl_2$ C 53.88; H 7.60 N 14.28; Cl 14.46 | C 53.85; H 7.63 N 14.25; Cl 14.49 |

EXAMPLE 149

The same procedures as described in Example 22 were repeated except that 4.50 g of 3-aminoindazole was employed instead of the 5.66 g of 3-amino-5-chloroindazole. As a result, 1-(3-morpholinopropyl)-3-aminoindazole having the following analytical values was obtained.

IR absorption spectrum ($\nu_{max}$, cm$^{-1}$): 3400, 3150, 2980, 1640 and 1610.

NMR spectrum [δ, CDCl$_3$]: 2.29(m, 8H), 3.59(m, 8H), 4.21(t, 2H) and 7.29(m, 4H).

Mass spectrum (m/e): 260(M+), 174, 146, 132 and 112.

Elemental Analysis Value: C$_{14}$H$_{22}$ON$_4$Cl$_2$: Calcd. (%): C 50.46; H 6.65; N 16.81; Cl 21.28. Found (%): C 50.41; H 6.59; N 16.98; Cl 21.23.

EXAMPLE 150

The same procedures as described in Example 1 were repeated except that 4.50 g of 3-aminoindazole and 5.03 g of (1-methyl-3-bromopropyl)-morpholine hydrobromide were employed instead of the 5.66 g of 3-amino-4-chloroindazole and the 4.83 g of 3-bromopropyldiethylamine hydrobromide, respectively. As a result, 1-(3-morpholinobutyl)-3-aminoindazole having the following analytical values was obtained in a yield of 48 %.

IR absorption spectrum ($\nu_{max}$, cm$^{-1}$): 3390, 3290, 2950, 1620 and 1590.

NMR spectrum [δCDCl$_3$]: 0.87(d, 3H), 1.61(m, 2H), 2.43(m, 5H), 3.57(t, 4H), 4.25(t, 2H), 5.10(bs, 2H) and 7.18(m, 4H).

Mass spectrum (m/e): 274(M+), 259, 173, 160 and 146.

Elemental Analysis Value: C$_{15}$H$_{24}$ON$_4$Cl$_4$: Calcd. (%): C 51.88; H 6.97; N 16.13; Cl 20.42. Found (%): C 52.03; H 6.78; N 16.07; Cl 20.45.

EXAMPLE 151

The same procedures as described in Example 150 were repeated except that 8.3 g of 2-bromoethylmorpholine hydrobromide was employed instead of the (1-methyl-3-bromopropyl)-morpholine hydrobromide. As a result, 1-(2-morpholinoethyl)-3-aminoindazole having the following analytical values was obtained in a yield of 59%.

IR absorption spectrum ($\nu_{max}$, cm$^{-1}$): 3390, 3200, 2950, 1635 and 1605.

NMR spectrum [δCDCl$_3$]: 2.43(m, 6H), 3.50(t, 4H), 4.20(t, 2H), 4.70(bs, 2H) and 7.09(m, 4H).

Mass spectrum (m/e): 246(M+), 174, 160 and 146.

Elemental Analysis Value: C$_{13}$H$_2$ON$_4$Cl$_2$: Calcd. (%): C 48.91; H 6.32; N 17.55; Cl 22.21. Found (%): C 49.02; L 6.35; N 17.31; Cl 22.28.

EXAMPLE 152

Morpholinoacrylamide having a boiling point of 125°~127°/1 mmHg was prepared by reacting morpholine with 3-chloropropionyl chloride in accordance with Ciba Ltd. Brit., 746 and 747, Mar. 21, 1956.

A mixture consisting of 9.43 g of 3-aminoindazole and 10 g of the morpholinoacrylamide was stirred for 2 days at 80° C. After the reaction mixture was cooled, to the mixture was added 15 ml of methyl alcohol to separate crystals. The crystals were obtained by filtration and dried under reduced pressure to give 15 g of 3-(3-morpholino-3-propionylamino)indazole having the following analytical values was obtained in a yield of 77%.

IR absorption spectrum ($\nu_{max}$, cm$^{-1}$): 3350, 3150, 1640, 1620 and 1550.

NMR spectrum [δ(CD$_3$)$_2$SO]: 3.00(t, 2H, J=6 Hz), 3.50(bs, 8H), 4.30(t, 2H, J=6 Hz) and 7.30(m, 4H).

To 60 ml of dioxane were added 1 g of the 3-(3-morpholino-3-propionylamino)indazole and 0.44 g of lithium aluminum hydride, and the mixture was stirred for 5 hours at 80° C. After the reaction mixture was cooled, to the mixture was added 0.5 ml of methyl alcohol. The pH of the aqueous layer of the mixture was adjusted to 10 with an aqueous sodium carbonate solution, and the alkali layer was extracted three times with 30 ml of chloroform. The chloroform layer was dried over anhydrous sodium sulfate and condensed so as to give 10 ml of a condensate. The condensate was left to stand for 12 hours to separate crystals. The crystals were obtained by filtration and dried under reduced pressure to give 0.80 g of 3-(3-morpholinopropylamino)indazole having the following analytic values in a yield of 85%.

IR absorption spectrum ($\nu_{max}$, cm$^{-1}$): 3225, 3070, 1650, 1615 and 1545.

NMR spectrum [δ, CDCl$_3$]: 2.26(m, 8H), 3.66(m, 8H), 4.23(t, 2H) and 7.31(m, 4HO.

Mass spectrum (m/e): 260(M+), 174, 146, 132 and 112.

In 15 ml of absolute ethyl alcohol was dissolved 1.0 g of the 3-(3-morpholinopropylamino)indazole, and into the solution was introduced dried hydrogen chloride gas under cooling with ice. Then to the solution was added anhydrous diethyl ether to separate crystals. The crystals were obtained by filtration and dried to give 3-(3-morpholinopropylamino)indazole hydrochloride having the following analytical value.

Elemental Analysis Value: C$_{14}$H$_{21}$ON$_4$Cl: Calcd. (%): C 56.66; H 7.13; N 18.88; Cl 11.94. Found (%): C 56.52; H 7.08; N 18.99; Cl 12.02.

EXAMPLES 153 and 154

The same procedures for preparing 3-(3-diethylaminopropylamino)indazole as described in Example 49 were repeated except that ω-halogenoalkylamine hydrobromides as set forth in Table 56 were employed instead of the 8.3 g of 3-bromopropyldiethylamine hydrobromide. The results including the analytical values are shown in Tables 56 and 57.

TABLE 56

| Example No. | ω-Halogenoalkylamine Hydrobromide | (g) | Product | Form | Yield (%) |
|---|---|---|---|---|---|
| 153 | 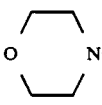 | 9.1 | 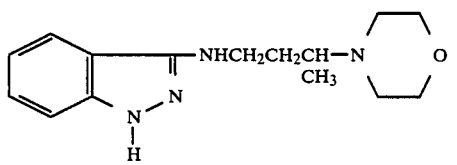 | Solid | 52 |

TABLE 56-continued

| Example No. | ω-Halogenoalkylamine Hydrobromide | (g) | Product | Form | Yield (%) |
|---|---|---|---|---|---|
| 154 | O⟨  ⟩N—CH₂CH₂Br·HBr | 8.3 | (indazole)—NHCH₂CH₂—N⟨  ⟩O with NH | Solid | 63 |

TABLE 57

| Example No. | IR Spectrum (cm⁻¹) | NMR Spectrum (δ, CDCl₃) | Mass Spectrum (m/e) | Elemental Analysis Value Calcd. (%) | Found (%) |
|---|---|---|---|---|---|
| 153 | 3400, 3310 | 0.87(d, 3H), 1.60(m, 2H) | 274(M⁺), 259 | C₁₅H₂₈N₄Cl | |
|  | 2940, 1620 | 2.43(m, 5H), 3.58(t, 4H) | 173, 160, 146 | C 57.96; H 7.46 | C 58.02; H 7.50 |
|  | 1580 | 4.25(t, 2H), 7.25(m, 4H) | | N 18.02; Cl 11.41 | N 17.79; Cl 11.38 |
| 154 | 3410, 3300 | 2.43(m, 6H), 3.52(t, 4H) | 246(M⁺), 160 | C₁₃H₁₉ON₄Cl | |
|  | 2940, 1620 | 4.20(t, 2H), 7.11(m, 4H) | 146, 132, 112 | C 55.22; H 6.77 | C 55.17; H 6.51 |
|  | 1580 | | | N 19.81; Cl 12.54 | N 20.02; Cl 12.64 |

EXAMPLE 155

To 60 ml of anhydrous N,N-dimethylformamide were added 4.21 g of 1-(3-morpholinopropyl)-3-aminoindazole obtained by the same method as described in Example 149, 8.98 g of 3-bromopropyldiethylamine hydrobromide and 7.89 g of anhydrous potassium carbonate, and the mixture was stirred for 12 hours at 80° C. After cooling, the mixture was added with 80 ml of water and extracted with diethyl ether. The diethyl ether layer was extracted three times with 2N hydrochloric acid, and the hydrochloric acid layer was washed with diethyl ether. The pH of the layer was adjusted to at least 11 with potassium carbonate, and the alkali layer was extracted three times with chloroform. The chloroform layer was dried over anhydrous sodium sulfate, and chloroform was removed under reduced pressure. The residue thus obtained was subjected to an aluminacolumn chromatography(alumina: 200 g) using chloroform as the developing solvent to give 3.50 g of 1-(3-morpholinopropyl)-3-(3-diethylaminopropylamino)indazole having the following analytical values in a yield of 58%.

IR absorption spectrum ($\nu_{max}$, cm⁻¹): 3400, 3225, 2950, 2880 and 1630.

NMR spectrum [δ, CDCl₃]: 0.99(t, 6H), 1.60(m, 2H), 2.44(m, 14H), 3.59(t, 4H), 4.25(t, 4H) and 7.20(m, 4H).

Mass spectrum (m/e): 373(M⁺, 100), 301(M-72, 87), 287(M-86, 116), 273(M-100, 73) and 259(M-114, 57).

In 50 ml of absolute ethyl alcohol was dissolved 3.0 g of the 1-(3-morpholinopropyl)-3-(3-diethylaminopropylamino)indazole, and into the solution was introduced dried hydrogen chloride gas under cooling with ice. Then to the solution was added anhydrous diethyl ether to separate crystals. The crystals were obtained by filtration and dried to give 1-(3-morpholinopropyl)-3-(3-diethylaminopropylamino)indazole dihydrochloride having the following analytical value.

Elemental Analysis Value: C₂₁H₃₇ON₅Cl₂: Calcd. (%): C 56.50; H 8.35; N 15.69; Cl 15.88. Found (%): C 56.42; H 8.17; N 15.81; Cl 15.93.

EXAMPLES 156-158

The same procedures as described in Example 155 were repeated escept that ω-halogenoalkylamine hydrobromides were employed instead of the 8.98 g of 3-bromopropyldiethylamine hydrobromide. The results including the analytical values are shown in Tables 58 and 59.

TABLE 58

| Example No. | ω-Halogenoalkylamine Hydrobromide | (g) | Product | Form | Yield (%) |
|---|---|---|---|---|---|
| 156 | 2,6-dimethylpiperidine-N—(CH₂)₃Br·HBr | 10.26 | 1-(3-morpholinopropyl)-3-[NH(CH₂)₃—N(2,6-dimethylpiperidine)]indazole | Oily Substance | 51 |

TABLE 58-continued

| Example No. | ω-Halogenoalkylamine Hydrobromide | (g) | Product | Form | Yield (%) |
|---|---|---|---|---|---|
| 157 | Cl—⟨piperidine⟩—N—(CH₂)₃Br·HBr | 10.46 | indazole-3-NH(CH₂)₃—N⟨piperidine⟩—Cl with 1-(CH₂)₃N-morpholine | Oily Substance | 49 |
| 158 | HO—⟨piperidine⟩—N—(CH₂)₃Br·HBr | 9.86 | indazole-3-NH(CH₂)₃—N⟨piperidine⟩—OH with 1-(CH₂)₃N-morpholine | Oily Substance | 44 |

TABLE 59

| Example No. | IR Spectrum (cm⁻¹) | NMR Spectrum (δ, CDCl₃) | Mass Spectrum (m/e) | Elemental Analysis Value Calcd. (%) | Found (%) |
|---|---|---|---|---|---|
| 156 | 3410, 3200 2985, 1630 1595 | 1.20(d, 6H), 1.39(m, 6H) 1.60(m, 2H), 2.40(m, 8H) 2.80(m, 2H), 3.56(t, 4H) 3.80(t, 2H), 4.21(t, 4H) 7.20(m, 4H) | 414(M⁺), 342 328, 314, 300 | $C_{24}H_{41}ON_5Cl_2$ C 59.25; H 8.50 N 14.39; Cl 14.57 | C 58.99; H 8.46 N 14.51; Cl 14.63 |
| 157 | 3390, 3215 2980, 1620 1580 | 1.55(m, 6H), 2.20(m, 9H) 2.95(m, 6H), 3.55(t, 4H) 4.20(t, 4H), 7.23(m, 4H) | 420(M⁺, 100), 348 334, 320, 306 | $C_{22}H_{36}ON_5Cl_2$ C 53.61; H 7.36 N 14.21; Cl 21.57 | C 53.55; H 7.21 N 14.41; Cl 21.55 |
| 158 | 3420, 3250 2970, 1610 1570 | 1.53(m, 6H), 2.22(m, 9H) 2.98(m, 6H), 3.59(t, 4H) 4.25(t, 4H), 7.21(m, 4H) | 402(M⁺, 100), 330 316, 302, 288 | $C_{22}H_{37}O_2N_5Cl_2$ C 55.69; H 7.86 N 14.76; Cl 14.94 | C 55.61; H 7.79 N 14.89; Cl 14.93 |

EXAMPLES 159 and 160

The same procedures as described in Example 1 were repeated except that ω-halogenoalkylamine hydrobromides as set forth in Table 60 and 4.5 g of 3-aminoindazole were employed instead of the 4.83 g of 3-bromopropyldiethylamine hydrobromide and the 5.66 g of 3-amino-4-chloroindazole, respectively. As a result, 1-(aminoalkyl)-3-aminoindazoles wer obtained.

The same procedures as described in Example 155 were repeated except that the 1-(aminoalkyl)-3-aminoindazoles and 9.4 g of 3-bromopropylmorpholine hydrobromide were employed instead of the 4.21 g of 1-(3-morpholinopropyl)-3-aminoindazole and the 8.98 g of 3-bromopropyldiethylamine hydrobromide, respectively. The results including the analytical values are shown in Tables 60 and 61

TABLE 60

| Example No. | ω-Halogenoalkylamine Hydrobromide | (g) | Product | Form | Yield (%) |
|---|---|---|---|---|---|
| 159 | (C₄H₉)₂N—(CH₂)₃Br·HBr | 11.08 | indazole-3-NH(CH₂)₃N-morpholine, 1-(CH₂)₃N(C₄H₉)₂ | Oily Substance | 51 |

TABLE 60-continued

| Example No. | ω-Halogenoalkylamine Hydrobromide | (g) | Product | Form | Yield (%) |
|---|---|---|---|---|---|
| 160 | 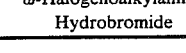 | 9.34 | 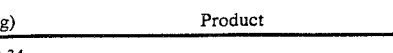 | Oily Substance | 52 |

TABLE 6

| Example No. | IR Spectrum (cm$^{-1}$) | NMR Spectrum (δ, CDCl$_3$) | Mass Spectrum (m/e) | Elemental Analysis Value Calcd. (%) | Found (%) |
|---|---|---|---|---|---|
| 159 | 3420, 3210 2980, 1615 1590 | 0.92(m, 6H), 1.28(m, 8H) 2.28(m, 12H), 3.67(m, 8H) 4.21(t, 4H), 7.27(m, 4H) | 430(M$^+$, 100), 358 344, 330, 316 | C$_{25}$H$_{45}$ON$_5$Cl$_2$ C 59.75; H 9.03 N 13.93; Cl 14.11 | C 59.59; H 9.11 N 13.82; Cl 14.05 |
| 160 | 3400, 3250 2970, 1610 1585 | 1.59(m, 6H), 2.29(m, 10H) 2.97(m, 6H), 3.58(t, 4H) 4.23(t, 4H), 7.27(m, 4H) | 386(M$^+$, 100), 314 300, 286, 272 | C$_{22}$H$_{37}$ON$_5$Cl$_2$ C 57.64; H 8.13 N 15.28; Cl 15.47 | C 57.56; H 7.97 N 15.35; Cl 15.59 |

EXAMPLE 161

3-Amino-4-hydroxyindazole was prepared in accordance with the following method as described in H. C. Brown and G. Zweifel, J. Am. Chem. Soc., 81 247(1959).

To 20 ml of diethyl ether solution containing 600 mg of magnesium powder was added dropwise a mixed solution consisting of 1.68 g of 3-amino-4-chloroindazole prepared by the method as described in Beck. Gunkther et al., Justus Liebigs Ann. Chem., 716, 47(1968), 2.06 g of isopropyl bromide and 20 ml of diethyl ether. Into the solution were introduced dried oxygen gas and dried carbon dioxide gas for 10 hours so as to reflux the solution, and the solution was left to stand for 12 hours. The pH of the solution was adjusted to 4.0 by adding dropwise sulfuric acid to the solution at 0° C. The solution was added with 50 ml of water and filtered. To the aqueous layer of the filtrate was added an aqueous potassium carbonate solution to separate crystals. The crystals were obtained by filtration and dried to give 0.626 g of 3-amino-4-hydroxyindazole having the following analytical values in a yield of 42%.

IR absorption spectrum ($\nu_{max}$, cm$^{-1}$): 3580, 2970, 1615 and 1580.

NMR spectrum [δ, CD$_3$OD]: 7.20(m, 3H).

Mass spectrum (m/e): 149(M+), 132(M-17), 71(M-78) and 58(M-91).

In 50 ml of absolute ethyl alcohol was dissolved 3.5 g of the 3-amino-4-hydroxyindazole, and into the solution was introduced dried hydrogen chloride gas under cooling with ice. Then to the solution was added anhydrous diethyl ether to separate crystals. The crystals were obtained by filtration and dried to give 3-amino-4-hydroxyindazole hydrochloride having the following analytical value.

Elemental Analysis Value: C$_7$H$_8$ON$_3$Cl: Calcd. (%): C 45.30; H 4.34; N 22.64; Cl 19.10. Found (%): C 45.21; H 4.38; N 22.61; Cl 19.18.

EXAMPLE 162

3-Amino-5-hydroxyindazole was prepared in accordance with the following method as described in R. L. Frank et al., J. Am. Chem. Soc., 71 3891(1949).

A mixture consisting of 5 g of 3-aminoindazole and 4.3 g of 95% sulfuric acid was stirred for 3 hours at 80° C. To the mixture was added 13 ml of water, and the pH of the mixture was adjusted to 14 with potassium hydroxide. The mixture was washed twice with 20 ml of chloroform, and water was removed under reduced pressure. The residue thus obtained was added with 12.5 g of potassium hydroxide and 0.6 ml of water, and the mixture was stirred for 8 hours at 250° C. After cooling, to the mixture was added hydrochloric acid to separate crystals. The crystals were obtained by filtration and dried to give 2.86 g of 3-amino-5-hydroxyindazole having the following analytical values.

IR absorption spectrum ($\nu_{max}$, cm$^{-1}$): 3600, 2980, 1620 and 1590.

NMR spectrum [δ, CD$_3$OD]: 7.19(m, 3H).

Mass spectrum (m/e): 149(M+), 132(M-17), 71(M-78) and 58(M-91).

In 50 ml of absolute ethyl alcohol was dissolved 3.5 g of the 3-amino-5-hydroxyindazole, and into the solution was introduced dried hydrogen chloride gas under cooling with ice. Then to the solution was added anhydrous diethyl ether to separate crystals. The crystals were obtained by filtration and dried to give 3-amino-5-hydroxyindazole hydrochloride having the following analytical value.

Elemental Analysis Value: C$_7$H$_8$ON$_3$Cl: Calcd. (%): C 45.30; H 4.34; N 22.64; Cl 19.10. Found (%): C 45.27; H 4.38; N 22.58; Cl 19.17.

Examples 163 and 164

The same procedures as described in Example 161 were repeated except that 3-amino-chloroindazoles as set forth in Table 62 were employed instead of the 1.68 g of 3-amino-4-chloroindazole. The 3-amino-chloroindazoles employed were prepared by the same methods as described in Examples 3 and 4.

TABLE 62

| Example No. | 3-Amino-chloroindazole | (g) | Product | Form | Yield (%) |
|---|---|---|---|---|---|
| 163 | 5-Cl-3-amino-indazole | 1.68 | 5-HO-3-amino-indazole | Solid | 49 |
| 164 | 7-Cl-3-amino-indazole | 1.68 | 7-HO-3-amino-indazole | Solid | 39 |

TABLE 63

| Example No. | IR Spectrum (cm$^{-1}$) | NMR Spectrum ($\delta$, CD$_3$OD) | Mass Spectrum (m/e) | Elemental Analysis Value Calcd. (%) | Found (%) |
|---|---|---|---|---|---|
| 163 | 3600, 2960<br>1610, 1570 | 7.18(m, 3H) | 149, 132, 71<br>58 | C$_7$H$_8$ON$_3$Cl<br>C 45.30; H 4.34<br>N 22.64; Cl 19.10 | <br>C 45.28; H 4.41<br>N 22.59; Cl 19.08 |
| 164 | 3590, 2980<br>1620, 1580 | 7.20(m, 3H) | 149, 132, 71<br>58 | C$_7$H$_8$ON$_3$Cl<br>C 45.30; H 4.34<br>N 22.64; Cl 19.10 | <br>C 45.21; H 4.43<br>N 22.61; Cl 18.98 |

EXAMPLE 165

3-Amino-5-iodoindazole was prepared in accordance with the following method as described in C. E. Kwartler et al., J. Am. Chem. Soc., 65 1804(1943).

A mixture consisting of 3.5 g of 5-iodoanthranilonitrile and 18 ml of hydrochloric acid was stirred for 1 hour at 0° C. To the reaction mixture was added dropwise 3 ml of water containing 1.95 g of sodium nitrile at 0° C. The mixture was added with 21.6 g of stannous chloride and 28 ml of hydrochloric acid and stirred for 4 hours at 0° C. After the mixture was rendered alkaline with 10N sodium hydroxide, the mixture was extracted three times with 30 ml of chloroform. The chloroform layer was dried over anhydrous sodium sulfate, and chloroform was removed under reduced pressure. The residue thus obtained was subjected to a silica gel-column chromatography(silica gel: 90 g) using chloroform as the developing solvent to give 2.02 g of 3-amino-5-indoindazole having the following analytical values in a yield of 54%.

IR absorption spectrum ($\nu_{max}$, cm$^{-1}$): 3400, 3260, 2950 and 1610.

NMR spectrum [$\delta$, D$_6$-DMSO]: 7.03(d, 1H), 7.36(d, 1H) and 8.06(s, 1H).

Mass spectrum (m/e): 259(M+), 258(M-1), 242(M-17), 228(M-31), 149(M-110) and 131(M-128).

In 50 ml of absolute ethyl alcohol was dissolved 3.6 g of the 3-amino-5-indoindazole, and into the solution was introduced dried hydrogen chloride gas under cooling with ice. Then to the solution was added anhydrous diethyl ether to separate crystals. The crystals were obtained by filtration and dried to give 3-amino-5-iodoindazole hydrochloride having the following analytical value.

Elemental Analysis Value: C$_7$H$_7$N$_3$ICl: Calcd. (%): C 28.45; H 2.39; N 14.22; I 42.94; Cl 12.00. Found (%): C 28.31; H 2.31; N 14.41; I 42.89; Cl 12.08.

EXAMPLE 166

The same procedures as described in Example 165 were repeated except that 3.5 g of 7-iodoanthranilonitrile was employed instead of the 3.5 g of 5-iodoanthranilonitrile. As a result, 2.12 g of 3-amino-7-iodoindazole having the following analytical values was obtained in a yield of 57%.

IR absorption spectrum ($\nu_{max}$, cm$^{-1}$): 3390, 3270, 2960 and 1620.

NMR spectrum [$\delta$, D$_6$-DMSO]: 7.0(d, 1H), 7.32(d, 1H) and 7.69(d, 1H).

Mass spectrum (m/e): 259(M+), 242(M-17), 228(M-31), 149(M-110) and 131(M-128).

In 50 ml of absolute ethyl alcohol was dissolved 3.6 g of the 3-amino-7-iodoindazole, and into the solution was introduced dried hydrogen chloride gas under cooling with ice. Then to the solution was added anhydrous diethyl ether to separate crystals. The crystals were obtained by filtration and dried to give 3-amino-7-iodoindazole hydrochloride having the following analytical value.

Elemental Analysis Value: C$_7$H$_7$N$_3$ICl: Calcd. (%): C 28.45; H 2.39; N 14.22; I 42.94; Cl 12.00. Found (%): C 28.51; H 2.42; N 13.99; I 42.98; Cl 12.10.

EXAMPLE 167

In 30 ml of sulfuric acid was dissolved 20 g of 3-aminoindazole prepared by the same method as described in Example 5. To the solution were added dropwise 10.2 ml of nitric acid and 10.2 ml of sulfuric acid at 0° C. After stirring the solution for 1 hour, the pH of the solution was adjusted to 10.4 with an aqueous ammonia solution. The reaction solution was extracted three times with 50 ml of chloroform. The chloroform layer was washed with water and dried over anhydrous sodium sulfate, and chloroform was removed under reduced pressure. The residue thus obtained was subjected to an alumina-column chromatography(alumina: 200 g) using chloroform as the developing solvent to give 3.66 g of 3-amino-5,7-dinitroindazole having the following analytical values in a yield of 11%.

IR absorption spectrum ($\nu_{max}$, cm$^{-1}$): 3460, 3370, 3100 and 1615.

NMR spectrum [δ, d$_6$-DMSO]: 7.86(s, 1H) and 8.10(s, 1H).

Mass spectrum (m/e): 223(M$^+$), 177(M-46), 131(M-92) and 115(M-108).

A mixture consisting of 6 g of the 3-amino-5,7-dinitroindazole, 18 g of iron powder, 60 ml of methyl alcohol, 30 ml of water and 3 ml of hydrochloric acid was stirred for 1.5 hours at 70° C. After cooling the reaction mixture, the mixture was filtered. The pH of the filtrate was adjusted to 11 with a potassium carbonate solution, and the filtrate was extracted three times with 50 ml of ethyl acetate. The ethyl acetate layer was washed with water and dried over anhydrous sodium sulfate, and ethyl acetate was removed under reduced pressure. The residue thus obtained was subjected to an alumina column chromatography(alumina: 200 g) using chloroform as the developing solvent to give 0.85 g of 3,5,7-triaminoindazole having the following analytical values in a yield of 19%.

IR absorption spectrum ($\nu_{max}$, cm$^{-1}$): 3460, 3370, 3180, 1635, 1610 and 1530.

NMR spectrum [δ, d$_6$-DMSO]: 3.38(bs, 6H) and 6.80(m, 2H).

Mass spectrum (m/e): 163(M$^{30}$), 147(M-16), 131(M-32) and 115(M-48).

In 20 ml of absolute ethyl alcohol was dissolved 1.0 g of the 3,5,7-triaminoindazole, and into the solution was introduced dried hydrogen chloride gas under cooling with ice. Then to the solution was added anhydrous diethyl ether to separate crystals. The crystals were obtained by filtration and dried to give 3,5,7-triaminoindazole trihydrochloride having the following analytical value.

Elemental Analysis Value: C$_7$H$_{12}$N$_5$Cl$_3$: Calcd. (%): C 30.85; H 4.44; N 25.69; Cl 39.02. Found (%): C 30.81; H 4.39; N 25.74; Cl 39.06.

What is claimed is:

1. A compound of the formula (I):

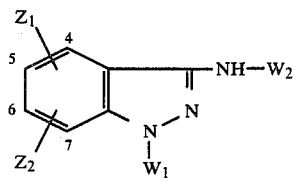

wherein
W$_1$ and W$_2$ each independently is a hydrogen atom or a

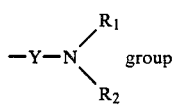

wherein Y is a n-C$_{1-6}$ alkylene group or a n-C$_{1-6}$ alkylene group having a C$_{1-6}$ alkyl group substituent; and R$_1$ and R$_2$ each independently is a hydrogen atom or a C$_{1-6}$ alkyl group, and

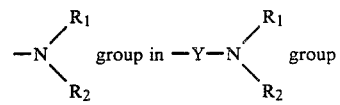

may form a saturated heterocyclic ring selected from the group consisting of morpholino, pyrrolidino, piperidino, homopiperidino and piperazino groups, and the saturated heterocyclic ring except the morpholino group may have at least one C$_{1-4}$ alkyl group, hydroxyl group or halogen atom as a substituent;

Z$_1$ is a hydrogen atom, a chlorine atom, a bromine atom, an iodine atom, a hydroxyl group, an amino group, a C$_1$—alkyl group or a methoxy group;

Z$_2$ is a hydrogen atom or an amino group;

when W$_1$ and W$_2$ are both hydrogen atoms, Z$_1$ is a hydroxyl group or an iodine atom and Z$_2$ is hydrogen atom, or Z$_1$ and Z$_2$ are both amino groups;

when W$_1$ is

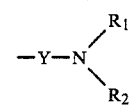

and W$_2$ is a hydrogen atom, Z$_1$ is not a hydroxyl group;

when Z$_1$ and Z$_2$ are both hydrogen atoms, the

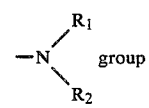

in either W$_1$ or W$_2$ is a morpholino group;

when Z$_1$ is a chlorine atom, a hydroxyl group, an iodine atom, a methyl group or a methoxy group, Z$_2$ is a hydrogen atom;

when Z$_1$ is an amino group, Z$_2$ is a hydrogen atom or an amino group;

when Z$_1$ is a methyl group, a methoxy group or an amino group, Z$_1$ is in the 5-position; when Z$_1$ is an iodine atom, Z$_1$ is in the 5- or 7-position; and when Z$_1$ and Z$_2$ are both amino groups, Z$_1$ and Z$_2$ are in the 5- and 7-positions;

and the physiologically acceptable acid addition salt thereof.

2. The compound of claim 1 of the formula (II):

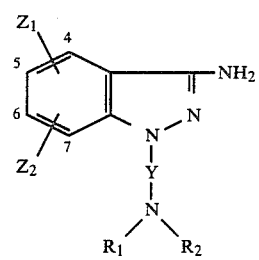

wherein
Y is a n-C$_{1-6}$ alkylene group or a propylene group having a C$_{1-4}$ alkyl group as a substituent; and R$_1$ and R$_2$ each independently is a C$_{1-6}$ alkyl group, and the

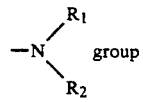 group may form a saturated heterocyclic ring selected from the group consisting of morpholino, pyrrolidino, piperidino, homopiperidino and piperazino groups, and the saturated heterocyclic ring except the morpholino group may have at least one $C_{1-4}$ alkyl group, hydroxyl group or chlorine atom as a substituent;

$Z_1$ is a chlorine atom, a bromine atom, an iodine atom, a hydroxyl group, an amino group, a $C_{1-3}$ alkyl group or a methoxy group;

$Z_2$ is a hydrogen atom or an amino group;

when $Z_1$ is a chlorine atom, a hydroxyl group, an iodine atom, a methyl group or a methoxy group, $Z_2$ is a hydrogen atom;

when $Z_1$ is an amino group, $Z_2$ is a hydrogen atom or an amino group;

when $Z_1$ is a methyl group, a methoxy group or an amino group, $Z_1$ is in the 5-position; when $Z_1$ is an iodine atom, $Z_1$ is in the 5- or 7-position; and when $Z_1$ and $Z_2$ are both amino groups, $Z_1$ and $Z_2$ are in the 5- and 7-positions.

3. The compound of claim 2, wherein Y is a n-propylene group, a n-hexylene group, a 3-methylpropylene group or a 3-(2-methylpropyl)propylene group.

4. The compound of claim 3, wherein $R_1$ and $R_2$ are both $C_{1-4}$ alkyl groups.

5. The compound of claim 3, wherein

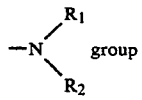 group is a piperidino group.

6. The compound of claim 2, wherein Y is a n-propylene group; and

is a 2-methylpiperidino group, a 2,6-dimethylpiperidino group, a 4-hydroxypiperidino group, a 4-chloropiperidino group, a homopiperidino group, a 4-methylpiperazino group, a pyrrolidino group or a morpholino group.

7. The compound of claims 4, 5 or 6, wherein $Z_1$ is a chlorine atom in the 5-position, and $Z_2$ is a hydrogen atom.

8. The compound of claims 4, 5 or 6, wherein $Z_1$ is a hydroxyl group in the 5-position, and $Z_2$ is a hydrogen atom.

9. The compound of claim 2, wherein Y is a n-propylene group; $R_1$ and $R_2$ are both ethyl groups; $Z_1$ is a chlorine atom in either 4-, 6- or 7-position, an amino group in the 5-position, a methoxy groups in the 5-position, a methyl group in the 5-position or an iodine atom in either 5- or 7-position; and $Z_2$ is a hydrogen atom.

10. The compound of claim 2, wherein Y is a n-propylene group; $R_1$ and $R_2$ are both ethyl groups; $Z_1$ is a hydroxyl group in either 4-, 6- or 7-position; and $Z_2$ is a hydrogen atom.

11. The compound of claim 2, wherein Y is a n-propylene group; $R_1$ and $R_2$ are both ethyl groups; $Z_1$ is an amino group in the 5-position; and $Z_2$ is an amino group in the 7-position.

12. The compound of claim 1 of the formula (III):

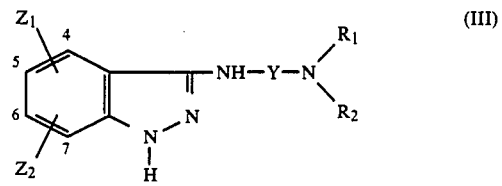 (III)

wherein Y, $R_1$, $R_2$, $Z_1$ and $Z_2$ are the same as defined in the formula (II).

13. The compound of claim 12, wherein Y is a n-propylene group, a n-hexylene group, a 3-methylpropylene group or a 3-(2-methylpropyl)propylene group.

14. The compound of claim 13, wherein $R_1$ and $R_2$ are both $C_{1-4}$ alkyl groups.

15. The compound of claim 13, wherein

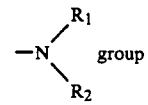 group is a piperidino group.

16. The compound of claim 12, where Y is a n-propylene group; and

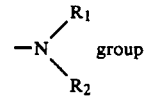 group is a 2-methylpiperidino group, a 2,6-dimethylpiperidino group, a 4-hydroxypiperidino group, a 4-chloropiperidino group, a homopiperidino group, a 4-methylpiperazino group, a pyrrolidino group or a morpholino group.

17. The compound of claims 14, 15 and 16, wherein $Z_1$ is a chlorine atom in the 5-positron, and $Z_2$ is a hydrogen atom.

18. The compound of claims 14, 15 and 16, wherein $Z_1$ is a hydroxyl group in the 5-position, and $Z_2$ is a hydrogen atom.

19. The compound of claim 12, wherein Y is a n-propylene group; $R_1$ and $R_2$ are both ethyl groups; $Z_1$ is a chlorine atom in either 4-, 6- or 7-position, an amino group in the 5-position, a methoxy group in the 5-position, a methyl group in the 5-position or an iodine atom in either 5- or 7-position; and $Z_2$ is a hydrogen atom.

20. The compound of claim 12, wherein Y is a n-propylene group; $R_1$ and $R_2$ are both ethyl groups; $Z_1$ is a hydroxyl group in either 4-, 6- or 7-position; and $Z_2$ is a hydrogen atom.

21. The compound of claim 12, wherein Y is a n-propylene group; $R_1$ and $R_2$ are both ethyl groups; $Z_1$ is an amino group in the 5-position; and $Z_2$ is an amino group in the 7-position.

22. The compound of claim 1 of the formula (IV):

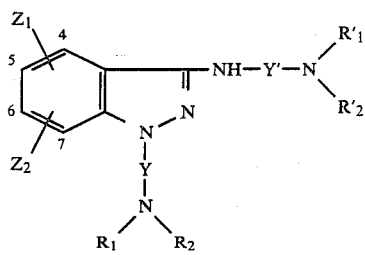 (IV)

wherein Y, $R_1$, $R_2$, $Z_1$ and $Z_2$ are the same as defined in the formula (II), and Y', $R'_1$ and $R'_2$ represent the same meaning as Y, $R_1$ and $R_2$, respectively.

23. The compound of claim 22, wherein Y and Y' each independently is an ethylene group, a n-propylene group, a n-hexylene group, a 3-methylpropylene group or a 3-(2-methylpropyl)propylene group; and

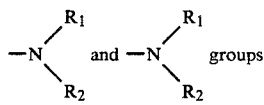
groups
each independently is a dimethylamino group, a diethylamino group, a di-n-propylamino group, a di-n-butylamino group, a pyrrolidino group, a piperidino group, a homopiperidino group, a 2-methylpiperidino group, a 4-methylpiperazino group or a morpholino group.

24. The compound of claim 22, wherein Y is a n-propylene group;

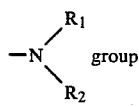

is a diethylamino group or a piperidino group; Y' is a n-propylene group, a n-hexylene group or a 3-methylpropylene group; and

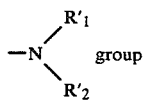

is a dimethylamino group, a diethylamino group, a di-n-propylamino group, a di-n-butylamino group or a piperidino group.

25. The compound of claim 22, wherein Y is a 3-methylpropyl group;

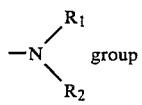

is a dimethylamino group or a piperidino group; Y' a n-propylene group, a 3-methylpropylene group, or a 3-(2-methylpropyl)propylene group; and

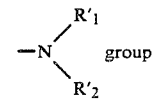

group(is a dimethylamino group, a diethylamino group or a piperidino group.

26. The compound of claim 22, wherein Y is a n-propylene group;

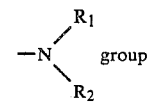

is a pyrrolidino group; Y' is a n-propylene group; and

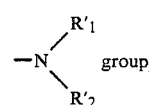

is a homopiperidino group, a 2-methylpiperidino group or a 4-methylpiperazino group.

27. The compound of claim 22, wherein Y is a n-propylene group;

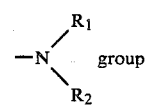

is a morpholino group; Y' is a n-propylene group; and

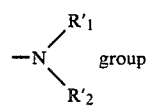

is a diethylamino group, a 2,6-dimethylpiperidino group, a 4-chloropiperidino group or a 4-hydroxypiperidino group.

28. The compound of claims 24, 25, 26 and 27, wherein $Z_1$ is a chlorine atom in the 5-position, and $Z_2$ is a hydrogen atom.

29. The compound of claims 24, 25, 26 and 27, wherein $Z_1$ is a hydroxyl group in the 5-position, and $Z_2$ is a hydrogen atom.

30. The compound of claim 22, wherein Y and Y' are both n-propylene groups;

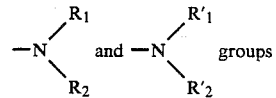

are both diethylamino groups; $Z_1$ is a chlorine atom in either 4-, 6- or 7-position, a hydroxyl group in either 6- or 7-position, an amino group in the 5-position, or an iodine atom in either 5- or 7-position; and $Z_2$ is a hydrogen atom.

31. The compound of claim 22, wherein Y and Y' are both n-propylene groups;

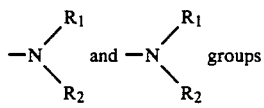 are both diethylamino groups; $Z_1$ is an amino group in the 5-position; and $Z_2$ is an amino group in the 7-position.

32. The compound of claim 1 of the formula (V):

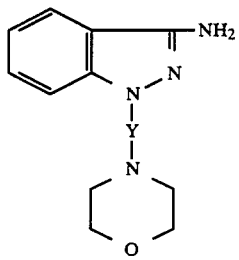

(V)

wherein Y is a n-$C_{1-6}$ alkylene group or a propylene group having a $C_{1-4}$ alkyl group as a substituent.

33. The compound of claim 32, wherein Y is an ethylene group, a n-propylene group or a 3-methylpropylene group.

34. The compound of claim 1 of the formula (VI):

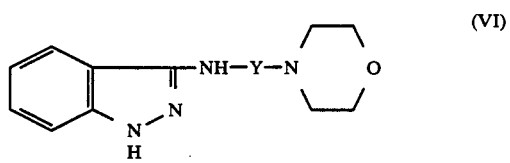

(VI)

wherein Y is the same as defined in the formula (V).

35. The compound of claim 34, wherein Y is an ethylene group, a n-propylene group or a 3-methylpropylene group.

36. The compound of claim 1 of the formula (VII):

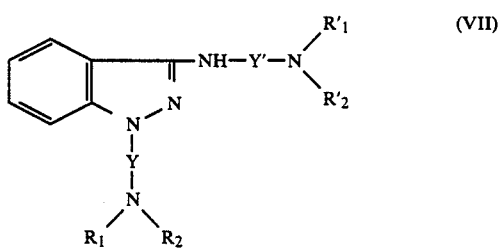

(VII)

wherein Y and Y' each independently is a n-$C_{1-6}$ alkylene group or a n-propylene group having a $C_{1-4}$ alkyl group as a substituent and either

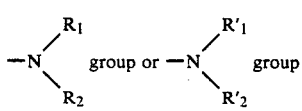

is a morpholino group, and the remaining

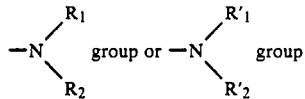

is a di-$C_{1-6}$ alkylamino group or a saturated heterocyclic ring selected from the group consisting of morpholino, pyrrolidino, piperidino, homopiperidino and piperazino, and the saturated heterocyclic ring except the morpholino group, may have at least one $C_{1-4}$ alkyl group, hydroxyl group or halogen atom as a substituent.

37. The compound of claim 36, wherein Y is an ethylene group, a n-propylene group, a hexylene group or a 3-methylpropylene group, a 3-(2-methylpropyl)propylene group.

38. The compound of claim 37, wherein the remaining

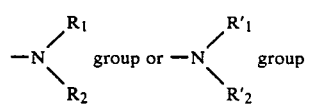

is a di-$C_{1-4}$ alkylamino group.

39. The compound of claim 36, wherein Y and Y' are both n-propylen groups;

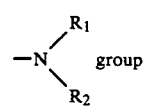

is a morpholino group; and

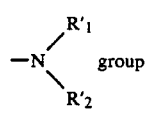

is a diethylamino group, a 2,6-dimethylpiperidino group, a 4-chloropiperidino group or a 4-hydroxypiperidino group.

40. The compound of claim 36, wherein Y and Y' are both n-propylene groups;

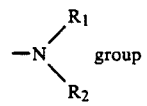

is a di-n-butylamino group or a piperidino group; and

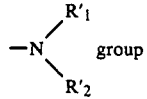

is a morpholino group.

41. The compound of claim 1, wherein $W_1$ and $W_2$ are both hydrogen atoms; $Z_1$ is an iodine atom in the 5- or 7-position or a hydroxyl group; and $Z_2$ is a hydrogen atom.

42. The compound of claim 1, wherein $W_1$ and $W_2$ are both hydrogen atoms; $Z_1$ is an amino group in the 5-position; and $Z_2$ is an amino group in the 7-position.

* * * * *